US008558059B2

(12) United States Patent
Heard

(10) Patent No.: US 8,558,059 B2
(45) Date of Patent: *Oct. 15, 2013

(54) GENES FOR CONFERRING TO PLANTS INCREASED TOLERANCE TO ENVIRONMENTAL STRESSES

(75) Inventor: Jacqueline E. Heard, Stonington, CT (US)

(73) Assignee: Mendel Biotechnology, Inc., Hayward, CA (US)

( * ) Notice: Subject to any disclaimer, the term of this patent is extended or adjusted under 35 U.S.C. 154(b) by 1284 days.

This patent is subject to a terminal disclaimer.

(21) Appl. No.: 11/069,255

(22) Filed: Feb. 28, 2005

(65) Prior Publication Data

US 2005/0172364 A1    Aug. 4, 2005

Related U.S. Application Data

(60) Continuation of application No. 10/112,887, filed on Mar. 18, 2002, now abandoned, and a continuation-in-part of application No. 10/412,699, filed on Apr. 10, 2003, now Pat. No. 7,345,217, which is a continuation-in-part of application No. 09/713,994, filed on Nov. 16, 2000, now abandoned, application No. 11/069,255, which is a continuation-in-part of application No. 10/675,852, filed on Sep. 30, 2003, now abandoned, which is a continuation-in-part of application No. 09/713,994, filed on Nov. 16, 2000, now abandoned, application No. 11/069,255, which is a continuation-in-part of application No. 10/286,264, filed on Nov. 1, 2002, now abandoned, which is a division of application No. 09/533,030, filed on Mar. 22, 2000, now abandoned.

(60) Provisional application No. 60/166,228, filed on Nov. 17, 1999, provisional application No. 60/125,814, filed on Mar. 23, 1999.

(51) Int. Cl.
C12N 15/82    (2006.01)

(52) U.S. Cl.
USPC .......................................... 800/290

(58) Field of Classification Search
None
See application file for complete search history.

(56) References Cited

U.S. PATENT DOCUMENTS

| 6,121,513 | A | 9/2000 | Zhang et al. |
| 6,235,975 | B1 * | 5/2001 | Harada et al. ............ 800/306 |
| 6,495,742 | B1 | 12/2002 | Shinozaki et al. |
| 6,664,446 | B2 | 12/2003 | Heard et al. |
| 6,677,504 | B2 | 1/2004 | da Costa e Silva et al. |
| 6,706,866 | B1 | 3/2004 | Thomashow et al. |
| 6,717,034 | B2 | 4/2004 | Jiang et al. |
| 6,835,540 | B2 | 12/2004 | Broun et al. |
| 6,946,586 | B1 | 9/2005 | Fromm et al. |
| 7,109,393 | B2 | 9/2006 | Gutterson et al. |
| 7,135,616 | B2 | 11/2006 | Heard et al. |
| 7,193,129 | B2 | 3/2007 | Reuber et al. |
| 7,196,245 | B2 | 3/2007 | Jiang et al. |
| 7,223,904 | B2 | 5/2007 | Heard et al. |
| 7,238,860 | B2 | 7/2007 | Ratcliffe et al. |
| 7,345,217 | B2 | 3/2008 | Zhang et al. |
| 7,511,190 | B2 | 3/2009 | Creelman et al. |
| 7,598,429 | B2 | 10/2009 | Heard et al. |
| 7,601,893 | B2 | 10/2009 | Reuber et al. |
| 7,635,800 | B2 | 12/2009 | Ratcliffe et al. |
| 7,659,446 | B2 | 2/2010 | Sherman et al. |
| 7,663,025 | B2 | 2/2010 | Heard et al. |
| 7,692,067 | B2 | 4/2010 | Creelman et al. |
| 2002/0023281 | A1 | 2/2002 | Gorlach et al. |
| 2002/0102695 | A1 * | 8/2002 | Silva et al. .............. 435/199 |
| 2003/0041356 | A1 | 2/2003 | Reuber et al. |
| 2003/0061637 | A1 | 3/2003 | Jiang et al. |
| 2003/0093837 | A1 | 5/2003 | Keddie |
| 2003/0101481 | A1 | 5/2003 | Zhang et al. |
| 2003/0121070 | A1 | 6/2003 | Adam et al. |
| 2003/0126638 | A1 | 7/2003 | Allen et al. |
| 2003/0131386 | A1 | 7/2003 | Samaha et al. |
| 2003/0183300 | A1 | 10/2003 | Siebert |
| 2003/0188330 | A1 | 10/2003 | Heard |
| 2003/0217383 | A1 | 11/2003 | Reuber et al. |
| 2003/0226173 | A1 | 12/2003 | Ratcliffe et al. |
| 2004/0009476 | A9 | 1/2004 | Harper et al. |
| 2004/0019927 | A1 | 1/2004 | Sherman et al. |
| 2004/0045049 | A1 | 3/2004 | Zhang et al. |
| 2004/0098764 | A1 | 5/2004 | Heard et al. |
| 2004/0111768 | A1 | 6/2004 | da Costa e Silva et al. |

(Continued)

FOREIGN PATENT DOCUMENTS

AR    PO70102784    9/2008
EP    1230345    8/2002

(Continued)

OTHER PUBLICATIONS

Smolen et al., Genetics, 2002, vol. 161, pp. 1235-1246.*

(Continued)

Primary Examiner — David H Kruse
Assistant Examiner — Russell Boggs
(74) Attorney, Agent, or Firm — Jeffrey M. Libby; Yifan Mao

(57) ABSTRACT

The invention relates to plant transcription factor polypeptides, polynucleotides that encode them, homologs and orthologs from a variety of plant species, and methods of using the polynucleotides and polypeptides to produce transgenic plants having advantageous properties compared to a reference or wild-type plant. These properties include increased tolerance to environmental stresses, including salt stress, drought, osmotic stress, water deficit, cold and heat.

18 Claims, No Drawings

(56) References Cited

U.S. PATENT DOCUMENTS

| | | | |
|---|---|---|---|
| 2004/0128712 | A1 | 7/2004 | Jiang et al. |
| 2005/0022266 | A1 | 1/2005 | Wu |
| 2005/0086718 | A1 | 4/2005 | Heard |
| 2005/0097638 | A1 | 5/2005 | Jiang et al. |
| 2005/0155117 | A1 | 7/2005 | Century et al. |
| 2006/0008874 | A1 | 1/2006 | Creelman et al. |
| 2006/0015972 | A1 | 1/2006 | Heard et al. |
| 2006/0162018 | A1 | 7/2006 | Gutterson et al. |
| 2007/0022495 | A1 | 1/2007 | Reuber et al. |
| 2007/0101454 | A1 | 5/2007 | Jiang et al. |
| 2007/0184092 | A1* | 8/2007 | Meyer et al. ............... 424/442 |
| 2007/0199107 | A1 | 8/2007 | Ratcliffe |
| 2007/0226839 | A1 | 9/2007 | Gutterson et al. |
| 2008/0040973 | A1 | 2/2008 | Nelson et al. |
| 2008/0104730 | A1 | 5/2008 | Wu |
| 2008/0155706 | A1 | 6/2008 | Riechmann et al. |
| 2008/0163397 | A1 | 7/2008 | Ratcliffe |
| 2008/0172759 | A1 | 7/2008 | da Costa e Silva et al. |
| 2008/0229448 | A1 | 9/2008 | Libby et al. |
| 2008/0301836 | A1 | 12/2008 | Century et al. |
| 2008/0301840 | A1 | 12/2008 | Gutterson et al. |
| 2008/0301841 | A1 | 12/2008 | Ratcliffe et al. |
| 2008/0313756 | A1 | 12/2008 | Zhang et al. |
| 2009/0044297 | A1 | 2/2009 | Andersen |
| 2009/0049566 | A1 | 2/2009 | Zhang et al. |
| 2009/0049573 | A1 | 2/2009 | Dotson |
| 2009/0138981 | A1 | 5/2009 | Repetti et al. |
| 2009/0151015 | A1 | 6/2009 | Adam et al. |
| 2009/0183270 | A1 | 7/2009 | Adams |
| 2009/0192305 | A1 | 7/2009 | Riechmann et al. |
| 2009/0205063 | A1 | 8/2009 | Zhang et al. |
| 2009/0265807 | A1 | 10/2009 | Kumimoto et al. |
| 2009/0265813 | A1 | 10/2009 | Gutterson et al. |
| 2009/0276912 | A1 | 11/2009 | Sherman et al. |
| 2010/0071086 | A1 | 3/2010 | Repetti et al. |
| 2010/0083395 | A1 | 4/2010 | Reuber et al. |
| 2010/0083402 | A1 | 4/2010 | Heard et al. |
| 2010/0107279 | A1 | 4/2010 | Ratcliffe et al. |
| 2010/0162427 | A1 | 6/2010 | Riechmann et al. |
| 2010/0175145 | A1 | 7/2010 | Heard et al. |
| 2010/0186105 | A1 | 7/2010 | Creelman et al. |
| 2010/0186106 | A1 | 7/2010 | Creelman et al. |
| 2010/0192249 | A1 | 7/2010 | Creelman et al. |
| 2010/0223689 | A1 | 9/2010 | Creelman et al. |
| 2010/0281565 | A1 | 11/2010 | Engler et al. |

FOREIGN PATENT DOCUMENTS

| | | |
|---|---|---|
| EP | 1420630 | 2/2003 |
| EP | 1601758 | 9/2004 |
| WO | WO0136598 A1 | 5/2001 |
| WO | WO01/45493 | 6/2001 |
| WO | WO02/16655 | 6/2001 |
| WO | WO 02/057439 | 7/2002 |
| WO | WO-02057439 | 7/2002 |
| WO | WO-02079245 | 10/2002 |
| WO | WO-03/014327 A2 | 2/2003 |
| WO | WO-2004031349 | 4/2004 |
| WO | WO2004076638 | 9/2004 |
| WO | WO2005033319 A2 | 4/2005 |
| WO | WO2008002480 A2 | 1/2008 |

OTHER PUBLICATIONS

Liu et al. The Plant Cell, 1998, vol. 10, pp. 1391-1406.*
Eisen 1998, Genome Research 8: 163-167.*
Edwards et al Jul. 1998, Plant Physiology 117: 1015-1022.*
U.S. Appl. No. 60/434,166, Creelman, R. et al.
Carre, I. et al. (1995) Multiple DNA-protein complexes at a circadian-regulated promoter element. Plant Cell 7: 2039-2051.
Edwards, D. et al. (1997) Transcription factor [*Arabidopsis thaliana*], NCBI acc. No. Y13723/CAA74051.1.
Edwards, D. et al. (1998) Transcription factor [Fragment]. TrEMBL entry O23634.
Edwards, D. et al. (1998) CCAAT-binding transcription factor subunit A. TrEMBL entry O23310.
Lotan, T. et al. (1998) *Arabidopsis* Leafy Cotyledon1 is sufficient to induce embryo development in vegetative cells. Cell 1195-1205.
Kusnetsov, V. et al. (1999) The assembly of the CAAT-box binding complex at a photosynthesis gene promoter is regulated by light, cytokinin, and the stage of the plastids. J. Biol. Chem. 274: 36009-36014.
Bloecker, H. et al. (2000) Transcription facotr NF-Y, CCAAT-binding-like protein. TrEMBL entry Q9LFI3.
Masiero S. et al. (2001) NF-YB1 protein [*Oryza sativa* (japonica cultivar-group)]. NCBI acc. No. CAC37695.
Bezhani, S. et al. (2001) A repressor with similarities to prokaryotic and eukayotic DNA helicases controls the assembly of the CAAT box binding . . . J. Biol. Chem. 276: 23785-23789.
Kwong, R.W. et al. (2003) Leafy Cotyledon1—Like defines a class of regulators essential for embryo development. Plant Cell 15: 5-18.
Lin, X., et al. (1999) Putative CCAAT-box binding transcription factor. TrEMBL entry Q9ZQC3.
Covitz, P.A. et al. (Nov. 11, 1997) 00429 MtRHE *Medicago truncatula* cDNA 5' similar to CCAAT box DNA binding transcription factor, mRNA sequence. NCBI acc. No. AA660543.
Nakamura, Y., (Apr. 20, 1999) "*Arabidopsis thaliana* genomic DNA, chromosome 5, P1 clone: MNJ7, complete sequence" NCBI accession No. AB025628 (GI:1922961, protein_id="AAB70405.1).
Osborne, B.I., et al. (Jan. 21, 1997); "*Arabidopsis thaliana* chromosome 1" NCBI accession No. AC000106 (gi:1785951) (pos. 59348-59974).
Rounsley, S.D., et al., (Oct. 3, 1998) "*Arabidopsis thaliana* clone T7F6" NCBI accession No. AC005770 (pos 56423-57963) GI:20197447, protein_id="AAC79602.2).
Lin, X., et al. (Dec. 29, 1998); "*Arabidopsis thaliana* clone T2N18" NCBI accession No. AC006260 (gi:4071012) (pos 40445-41633).
Lin, X., et al. (Mar. 11, 1999) *Arabidopsis thaliana* clone T10F5, NCBI acc. No. AC007063 (pos. 46630-46727) (GI:4558662).
Gherraby, X., et al., (Nov. 9, 1999) "*Arabidopsis thaliana* heme activated protein (HAP5c) mRNA, complete cds" NCBI accession No. AF193440 (gi:6289056).
Shoemaker, R., et al (Feb. 19, 1999) "Sa26b07.y1 Gm-c1004 Glycine max cDNA clone Genome systems clone ID: Gm-c1004-398 5' similar to TR:O23634 O23634 transcription factor" NCBI accession No. AI442376 (gi:4295745).
Shoemaker, R., et al (Feb. 19, 1999) ("Sa26b07.x1 Gm-c1004 Glycine max cDNA clone genome systems clone ID: Gm-c1004-398 3' similar to TR:O23634 O23634 transcription factor" NCBI accession No. AI442465 (gi:4298466).
Alcala, J., et al. (Mar. 9, 1999) "EST244824 tomato ovary, TAMU *Lycopersicon esculentum* cDNA clone cLED6C8, mRNA sequence"; (*Lycopersicon esculentum*) NCBI accession No. AI486503 (gi:4381874).
Bevan, M., et al. (Jul. 6, 1997); "*Arabidopsis thaliana* DNA chromosome 4, ESSA I contig fragment No. 1" CAB10233.1, NCBI accession No. Z97336 (gi:2244788) (pos. 102664-103149).
Blewitt, M. et al. (Jun. 11, 1999) "BNLGHi12445 Six-day Cotton fiber *Gossypium hirsutum* cDNA 5' similar to CCAAT-binding tranion factor subunit A (CBF-A) (NF-Y Protein . . . " NCBI accession No. AI725612 (gi:504464).
Blewitt, M. et al. (Jun. 11, 1999) "BNLGHi12022 Six-day Cotton fiber *Gossypium hirsutum* cDNA' similar to (Y13723) Transcription factor [*Arabidopsis thaliana*], mRNA . . . " NCBI accession No. AI728916 (gi:5047768).
Blewitt, M. et al. (Jun. 11, 1999) "BNLGHi9010 Six-day Cotton fiber *Gossypium hirsutum* cDNA 5' similar to (X59714) CAAT-box DNA binding protein subunit B (NF-YB) [*Zea Mays*]" NCBI acc, No. AI731250 (gi:5050102).
Blewitt, M. et al. (Jun. 11, 1999) "BNLGHi9078 Six-day Cotton fiber *Gossypium hirsutum* cDNA 5' similar to (X59714) CAAT-box DNA binding protein subunit b (NF-YB) [*Zea.* . " NCBI accession No. AI731275 (gi:5050127).
D'Ascenzo, M., et al. (Jun. 29, 1999); "EST263230 tomato susceptible, Cornell *Lycopersicon esculentum* cDNA cLESl8L2, mRNA sequence"; NCBI accession No. AI782351 (gi:5280392).

(56) References Cited

OTHER PUBLICATIONS

Shoemaker, R., et al. (Jul. 27, 1999); "sb97g11.y1 Gm-c1012 Glycine max cDNA clone Genome Systems clone ID: Gm-c1012-669 5' similar to SW:CBFA__Maize P25209 CCAAT-bind . . . " NCBI accession No. AI900024 (gi:5605926).

Shoemaker, R., et al. (Aug. 23, 1999); "sc74b05.y1 Gm-c1018 Glycine max cDNA clone Genome Systems clone ID: Gm-c1018-586 5' similar to SW:CBFA__Maize P25209 CCAAT-bi . . . "; NCBI accession No. AI965590 (gi:5760227).

Shoemaker, R. et al. (Aug. 23, 1999) "sc51h01.y1 Gm-c1015 Glycine max cDNA clone Genome Systems Clone ID: Gm-c1015-1130 5' similar to TR:023633 023633 Transcription factor" NCBI accession No. AI966550 (gi:5761187).

Bloecker, H., et al., (Nov. 15, 1999) "*Arabidopsis thaliana* DNA chromosome 3, BAC clone F4P12" NCBI accession No. AL132966 (pos. 15052-16661) (GI:6729485, protein_id="CAB67641.1).

Guo HH, et al. (2004) Protein tolerance to random amino acid change. 101: 9205-9210.

Alcala, J. et al. (Sep. 15, 1999) "EST281308 tomato callus, TAMU *Lycopersicon esculentum* cDNA clone cLEC39F2 similar to CAAT-box DNA binding protein subunit B (NF . . . " NCBI accession No. AW035570 (gi:5894326).

Li, X.Y., et al. (Apr. 23, 1993) "CAAT-binding transcription factor subunit A (CBF-A) (NF-Y protein chain B) (NF-YB) (CAAT-box DNA binding protein subunit B)" (*Zea mays*) NCBI accession No. P25209 (gi:115840).

Shoemaker, R. et al. (Oct. 27, 1999) "se03b02.y1 Gm-c1013 Glycine max cDNA clone Genome Systems clone ID: Gm-c1013-2404 5' similar SW:CBFA__Maize P25209 CCAAT-binding transc . . . ") NCBI accession No. AQ132359 (gi:6133966).

Shoemaker, R., et al. (Nov. 30, 1999) "se93e11.y1 Gm-c1027 Glycine max cDNA clone Genome Systems clone ID: Gm-c1027-357 5' similar to TR:O23310 O23310 CCAAT-binding transcription fac . . . ";NCBI accession No. AW200790 (gi:6481519).

Shoemaker, R.,et al. (Nov. 30, 1999) "sf09g11.y1 Gm-c1027 Glycine max cDNA clone Genome Systems clone ID: Gm-c1027-1821 5' similar to TR:O23310 O23310 CCAAT-binding transcri . . . " NCBI accession No. AW201996 (gi:6482782).

Vodkin, L.,et al. (Feb. 1, 2000) "GM210001A21D7 Gm-r1021 Glycine max cDNA clone Gm-r1021-158 3', mRNA sequence"; (Glycine max) NCBI accession No. AW348165 (gi:6845875).

Shoemaker, R. et al. (Feb. 7, 2000) "sh45e04.y1 Gm-c1017 Glycine max cDNA clone Genome Systems clone ID: Gm-c1017-4663 5' similar to TR:Q9ZQC3 Q9ZQC3 Putativ . . . ; mRNA sequence" NCBI accession No. AW395227 (gi:6913697).

Shoemaker, R. et al. (Feb. 7, 2000) "sg83f04.y1 Gm-c1026 Glycine max cDNA clone Genome Systems clone ID: Gm-c1026-344 5' similar to TR:023634 023634 transcription factor; mRNA se . . . " NCBI accession No. AW397727 (gi:6916197).

Shoemaker, R. et al. (Feb. 11, 2000) "si03a01.y1 Gm-c1029 Glycine max cDNA clone Genome Systems clone ID: Gm-c1029-97 5' similar to TR:081130 081130 CCAAT-box binding factor HAP3 . . . " NCBI accession No. AW432980 (gi:6964287).

Shoemaker, R. et al. (Feb. 24, 2000) sh23f03.y1 Gm-c1016 Glycine max cDNA clone Genome Systems clone ID: Gm-c1016-5622 5'similar to TR:Q9ZQC3 Q9ZQC3 Putative CCAAT-binding tr . . . NCBI accession No. AW459387 (gi:7029546).

Shoemaker, R., et al. (Mar. 13, 2000); "sj63c01.y1 Gm-c1033 Glycine max cDNA clone Genome Systems clone ID: Gm-c1033-1945 5'similar to SW:CBFA__Maize P25209 CCAAT-bin . . . " NCBI accession No. AW570530 (gi:7235201).

Shoemaker, R., et al. (Mar. 22, 2000) sj96g06.y1 Gm-c1023 Glycine max cDNA clone Genome Systems clone ID: Gm-c1023-2483 5'similar to TR:Q9ZQC3 Q9ZQC3 Putative CCAAT-binding . . . NCBI accession No. AW597630 (gi:7285143).

Kaneko, T., Edwards, D. et al. (Dec. 4, 1997) "Transcription factor [fragment]" (orgin-gene: hap3b) TREMBL Accession No. O23634).

Lotan, T. et al. (Nov. 1, 1998); protein: "CCAAT-box binding factor HAP3 homolog" TREMBEL Accession No. O81130

Covitz, P.A. et al. (1998) Expressed Sequence Tags from a Root-Hair-Enriched Medicago truncatula cDNA Library. Plant Physiol. 117 (4), 1325-1332.

Arents and Moudrianakis (Nov. 21, 1995) The histone fold: a ubiquitous architectural motif utilized in DNA compaction and protein dimerization. Proc Natl Acad Sci USA 92, 11170-11174.

Bi, W., et al. (Oct. 17, 1997). DNA binding specificity of the CCAAT-binding factor CBF/NF-Y. J Biol Chem 272, 26562-26572.

Caretti et al. (Dec. 1999) NF-Y associates with H3-H4 tetramers and octamers by multiple mechanisms. Mol Cell Biol 19: 8591-8603.

Carre and Kay (Dec. 1995). Multiple DNA-Protein complexes at a circadian-regulated promoter element. Plant Cell 7, 2039-2051.

Chang and Liu (Jul. 8, 1994). Human thymidine kinase CCAAT-binding protein is NF-Y, whose A subunit expression is serum-dependent in human IMR-90 diploid fibroblasts. J Biol Chem 269, 17898.

Coustry et al. (Jun. 14, 996). The transcriptional activity of the CCAAT-binding factor CBF is mediated by two distinct activation domains, one in the CBF-B subunit and the other in . . . J Biol Chem 271, 14485-14491.

Currie (Dec. 5, 1997). Functional interaction between the DNA binding subunit trimerization domain of NF-Y and the high mobility group protein HMG-I(Y). J Biol Chem 272, 30880-30888.

Dang V.D., et al. (Apr. 1996). The CCAAT box-binding factor stimulates ammonium assimilation in *Saccharomyces cerevisiae*, defining a new cross-pathway regulation between nitrogen and . . . J Bacteriol 178, 1842-1849.

De Silvio A et al. (Jul. 1, 1999) Dissection of the NF-Y transcriptional activation potential. Nucleic Acids Res 27: 2578-2584.

Faniello MC, et al. (Mar. 19, 1999) The B subunit of the CAAT-binding factor NFY binds the central segment of the Co-activator p300. J Biol Chem 274: 7623-7626.

Forsburg and Guarente (Feb. 1988). Mutational analysis of upstream activation sequence 2 of the CYC1 gene of *Saccharomyces cerevisiae*: a HAP2-HAP3-responsive site. Mol Cell Biol 8, 647-654.

Gancedo, J.M. (Jun. 1998). Yeast carbon catabolite repression. Microbiol Mol Biol Rev 62, 334-361.

Kehoe, D. et al. (Aug. 1994). Two 10-bp regions are critical for phytochrome regulation of a Lemna gibba Lhcb gene promoter. Plant Cell 6, 1123-1134.

Kater, et al. (Feb. 1998). Multiple AGAMOUS Homologs from Cucumber and Petunia Differ in their Ability to Induce Reproductive Organ Fate. Plant Cell 10:171-182.

Kim and Sheffery (Aug. 1990). Physical characterization of the purified CCAAT transcription factor, alpha-CP1. J Biol Chem 265, 13362-13369.

Gusmaroli et al. (2001) Regulation of the CCAAT-Binding NF-Y subunits in *Arabidopsis thaliana*. Gene 264: 173-185.

Lazar et al. (Mar. 1988) Transforming Growth Factor alpha: Mutation of Aspartic Acid 47 and Leucine 48 Results in Different Biological Activities. Mol. Cell Biol. 8: 1247-1252.

Lee J H. et al. (Oct. 1995) Derepression of the activity of genetically engineered heat shock factor causes constitutive synthesis of heat shock proteins and increased themotolerance in transgenic . . . Plant J 8:603-612.

Li, Q., et al. (Nov. 2, 1998). Xenopus NF-Y pre-sets chromatin to potentiate p300 and acetylation-responsive transcription from the Xenopus hsp70 promoter in vivo. EMBO J 17, 6300-6315.

Luger, et al. (Sep. 19, 1997). Crystal structure of the nucleosome core particle at 2.8 A resolution. Nature 389, 251-260.

McNabb, D.S., et al. (Dec. 1997). The *Saccharomyces cerevisiae* Hap5p homolog from fission yeast reveals two conserved domains that are essential for assembly of heterotetrameric . . . Mol Cell Biol 17, 7008-7018.

Meinke, D. (Dec. 4, 1992). A homeotic mutant of *Arabidopsis thaliana* with leafy cotyledons. Science 258, 1647-1650.

Meinke, D.W., et al. (Aug. 1994). Leafy Cotyledon Mutants of *Arabidopsis*. Plant Cell 6, 1049-1064.

Mantovani, R. (Oct. 18, 1999). The molecular biology of the CCAAT-binding factor NF-Y. Gene 239, 15-27.

(56) References Cited

OTHER PUBLICATIONS

Nakamura, Y., et al. (Dec. 31, 1997). Structural analysis of *Arabidopsis thaliana* chromosome 5. III. Sequence features of the regions of 1,191,918 bp covered by seventeen physically assigned P1 . . . DNA Res. 4(6): 401-414.

Myers, R.M., et al. (May 2, 1986). Fine structure genetic analysis of a beta-globin promoter. Science 232, 613-613.

Nakshatri, H., et al. (Nov. 15, 1996). Subunit association and DNA binding activity of the heterotrimeric transcription factor NF-Y is regulated by cellular redox. J Biol Chem 271, 28784-28791.

Nandi et al. (Feb. 24, 2000). A conserved function for *Arabidopsis* SUPERMAN in regulating floral-whorl cell proliferation in rice, a monocotyledonous plant. Curr. Biol. 10:215-218.

Parcy, F., et al. (Aug. 1997). The bscisic Acid-Insensitive3, FUSCA3, and Leady Cotyledon1 loci act in concert to control multiple aspects of *Arabidopsis* seed development. Plant Cell 9, 1265-1277.

Peng et al. (Dec. 1, 1997). The *Arabidopsis* GAI gene defines a signaling pathway that negatively regulates gibberellin responses. Genes Dev. 11: 3194-3205.

Pinkham, J.L., and Guarente, L. (Dec. 1985). Cloning and molecular analysis of the HAP2 locus: a global regulator of respiratory genes in *Saccharomyces cerevisiae*. Mol Cell Biol 5, 3410-3416.

Sabeheat, et al. (Jun. 1998). Expression of small heat-shock proteins at low temperatures. A possible role in protecting against chilling injuries. Plant Physiol 117, 651-658.

Sinha S. et al. (Feb. 28, 1995) Recombiant rat CBF-C, the third subunit of CBF/NFY, allows formation of protein-DNA complex with CBF-A and CBF-B and with yeast HAP2 and HAP3. Proc Natl Acad Sci U S A 92: 1624-1628.

Sinha S. et al. (Jan. 1996). Three classes of mutations in the A subunit of the CCAAT-binding factor CBF delineate functional domains involved in the three-step assembly of the CBF-DNA complex. Mol Cell Biol 16, 328-337.

Tasanen, K. et al. (Jun. 5, 1992). Promoter of the gene for the multifuncational protein disulfide isomerase polypeptide. Functional significance of the six CCAT boxes and . . . J Biol Chem 267, 11513-11519.

Thomas, H., and Howarth, C.J. (Feb. 2000). Five ways to stay green. J. Exp Bot 51 Spec No. 329-337.

Wendler W.M., et al. (Mar. 28, 1997). Identification of pirin, a novel highly conserved nuclear protein. J Biol Chem 272, 8482-8489.

West, M et al. (Dec. 1994). Leafy Cotyledon1 is an essential regulator of late embryogenesis and cotyledon identity in *Arabidopsis*. Plant Cell 6, 1731-1745.

Xing, Y et al. (Dec. 1993). Mutations in yeast HAP2/HAP3 define a hybrid CCAT box binding domain. EMBO J 12, 4647-4655.

Zhou, Y., and Lee, A.S. (Mar. 4, 1998). Mechanism for the suppression of the mammalian stress response by genistein, an anticancer phytoestrogen from soy. J Natl Cancer Inst 90, 381-388.

Prändl R. et al., (May 1998) HSF3, a new heat shock factor from *Arabidopsis thaliana*, derepresses the heat shock response and confers thermotolerance when overexpressed in . . . Molec. Gen. Genetics, 258:269-278.

Peng et al. (Jul. 15, 1999). 'Green revolution' genes encode mutant gibberellin response modulators, Nature 400:256-261.

Weigel and Nilsson (Oct. 12, 1995). A developmental switch sufficient for flower initiation in diverse plants. Nature 377:482-500.

Hollung et al. (Jun. 1997) Developmental stress and ABA modulation and mRNA levels for bZIP transcription factors and Vp1 in barley embryos and embryo-derived suspension cultures, Plant Molec Biol 35:(5) pp. 561-571.

Coupland (Oct. 1995). Flower development. Leafy blooms in aspen. Nature 377:482-483.

Forsburg and Guarente (Aug. 1989). Identification and characterization of HAP4: a third component of the CCAT-bound HAP2/HAP3 heteromer. Genes Dev 3, 1166-1178.

Hill et al. (Mar. 1998). Functional Analysis of Conserved Histidines in ADP Glucose Pyrophosphorylase from *Escherichia coli*. Biochem. Biophys. Res. Comm. 244:573-577.

Mandel et al. (Oct. 1992). Manipulation of flower structure in transgenic tobacco, Cell 71-133-143.

Maity, S.N., and de Crombrugghe, B. (May 1998). Role of the CCAAT-binding protein CBF/NF-Y in transcription. Trends Biochem Sci 23, 174-178.

Bucher and Trifonov (Jun. 1988). CCAAT box revisited: bidirectionality, location and context. J Biomol Struct Dyn 5, 1231-1236.

Bucher, P. (Apr. 20, 1990). Weight matrix descriptions of four eukaryotic RNA polymerase II promoter elements derived from 502 unrelated promoter sequences. J Mol Biol 212, 563-578.

Gelinas, R., et al. (Jan. 1985). Sequences of G gamma, A gamma, and beta genes of the Greek (A gamma) HPFH mutant: evidence for a distal CCAAT box mutation in the A gamma gene. Prog Clin Biol Res 191, 125-139.

Ito, T. et al. (Oct. 1995). A far-upstream sequence of the wheat histone H3 promoter functions differently in rice and tobacco cultured cells. Plant Cell Physiol 36, 1281-1289.

Mazon, M.J., et al. (Oct. 1982). Phosphorylation and inactivation of yeast fructose-bisphosphatase in vivo by glucose and by protein ionophores. A possible role for cAMP. Eur J Biochem 127, 605-608.

Olesen and Guarente (Oct. 1990). The HAP2 subunit of yeast CCAAT transcriptional activator contains adjacent domains for subunit association and DNA recognition: model for the . . . Genes Dev 4, 1714-1729.

Rieping, M. and Schoffel, F. (Jan. 1992). Synergistic effect of upstream sequences, CCAAT box elements, and HSE sequences for enhanced expression of chimaeric heat shock genes in transgenic . . . Mol Gen Genet 231, 226-232.

Bevan et al., Edwards, D., et al. (1998) CCAAT-binding transcription factor subunit A(CBF-A), TrEMBL Sequence O23310.

Lin et al. (1999) Putative CCAAT-box binding transcription factor, TrEMBL Sequence Q97ZQC3.

Lotan et al. (1998) *Arabidopsis* Leadfy Cotyledon1 is Sufficient to Induce Embryo Development in Vegatative Cells. Cell: 1195-1205.

Whetten et al (1999) Pine Triplex shoot tip library *Pinus taeda* clone ST32F09, NCBI AW04337.

Ryu et al. (1999) Flower bud cDNA *Brassica rapa* subsp. pekinensis cDNA clone RF0417, NCBI sequence AT002114.

Shoemaker et al. (1999) sa89f03.y1 Gmc1004 Glycine max cDNA clone Genome Systems Clone ID: Gm-c1004-6486, NCBI Sequence AI495007.

Li, X-Y et al. (1992) Evolutionary variation of the CCAAT-binding transcription factor NF-Y. Nucl. Acids Res. 20: 1087-1091.

Edwards, D. et al. (1997) Transcription factor [*Arabidopsis thaliana*]. NCBI acc. No. Y13723/CAA74051.1.

Edwards, D. et al. (1998) Multiple genes encoding the conserved CCAAT-box transcription factor complex are expressed in *Arabidopsis*. Plant Physiol. 117: 1015-1022.

Li, X-Y et al. (1999) CAAT-box DNA bind . . . [gi:22380]. NCBI acc. No. CAA42234.

Li, X-Y et al. (1999) transcriptiom fac . . . [gi:7443522]. NCBI acc. No. S22820.

Kusnetsov, V. et al. (1999) The assembly of the CAAT-box binding complex at a photosynthesis gene promoter is regulated by light, cytokinin, and the stage . . . J. Biol. Chem. 274:36009-36014.

Rounsley S.D. et al. (2000) Putative CCAAT-binding transcription factor subunit. TrEMBL entry Q9SLG0.

Bloecker, H. et al. (2000) Transcription factor NF-Y, CCAAT-binding-like protein. TrEMBL entry G9LFI3.

Kaneko T. et al. (2001) Similarity to CCAAT-box-binding transcription factor. TrEMBL entry Q9FGJ3.

Masiero S. et al. (2001) NF-YB1 protein [*Oryza sativa* (japonica cultivar)]. NCBI acc. No. CAC37695.

Shinn P. et al. (2001) At2g37060/T2N18.18 [*Arabidopsis thailiana*]. NCBI acc. No. AAL49943.

Bezhani, S. et al. (2001) A repressor with similarites to prokaryotic and eukayotic DNA helicases controls the assembly of the CAAT box binding complex . . . J. Biol. Chem. 276: 23785-23789.

Gusmaroli, G. et al. (2002) Regulation of the *Arabidopsis thaliana* CCAAT-binding nuclear factor Y subunits. Gene 283: 41-48.

Kwong, R.W. et al. (2003) Leafy Cotlyledon1-Like defines a class of regulators essential for embryo development. Plant Cell. 15: 5-18.

(56) References Cited

OTHER PUBLICATIONS

Lee, H. et al. (2003) *Arabidopsis* Leafy Cotyledon1 represents a functionally specialized subunit of the CCAAT binding transcription factor. Proc. Natl. Acad. Sci. 100: 2152-2156.

Smolen G.A. et al. (2002) Dominant alleles of the basic helix-loop-helix transcription factor ATR2 activate stress-responsive genes in *Arabidopsis*. Genetics 161: 1235-1246.

Liu Q. et al. 1998. Two transcription factors, DREB1 and DREB2, with an EREBP/AP2 DNA binding domain sperate two cellular signal transduction pathways in drought- and . . . Plant Cell 10:1391-1406.

Fourgoux-Nicol et al. 1999. Isolation of rapeseed genes expressed early and specifically during development of the male gametophyte. Plant Mol. Biol. 40: 857-872.

Kasuga et al. 1999. Improving plant drought, salt, and freezing tolerance by gene transfer of a single stress-inducible transcription factor. Nature Biotechnol. 17: 287-291.

Ohme-Takagi and Shinshi. 1995. Ethylene-Inducible DNA Binding Proteins that Interact with an Ethylene-Responsive Element. Plant Cell 7: 173-182.

Büttner and Singh. 1997. *Arabidopsis thaliana* ethylene-responsive element binding protein (AtEBP), an ehtylene-inducible, GCC box DNA-binding protein . . . PNAS 1997; 94:5961-5966.

Winicov, 1998. New molecular approaches to improving salt tolerance in crop plants. Annals Bot. 82: 705-710.

Urao et al. (1993) An *Arabidopsis* myb Homolog is Induced by Dehydration Stress and its Gene Product Binds to the Conserved MYB Recognition Sequence. Plant Cell 5: 1529-1539.

Edwards et al. (1997) *Arabidopsis thaliana* mRNA for Hap3b transcription factor. NCBI accession No. Y13724.

Benoist (1992) *Z. mays* mRNA for CAAT-box DNA binding protein subunit B (NF-YB). NCBI accession No. X59714.

Winicov and Basatola (1999) Transgenic Overexpression of the Transcription Factor Alfin 1 Enhances Expression of the Endogenous MsPRP2 Gene in . . . Plant Physiol. 120: 473-480.

Riechmann et al. 2000. *Arabidopsis* transcription factors: genome-wide comparative analysis among eukaryotes. Science 290: 2105-10.

Albani and Robert (1995) Cloning and characterization of a *Brassica napus* gene encoding a homologue of the B subunit of a heteromeric CCAAT-binding factor. Gene 167: 209-213.

European Partial Search report mailed Apr. 27 2007, for EP application 04714657 filed Feb. 25, 2004, nine pages.

European Partial Search Report mailed Apr. 27, 2007, for EP Application No. 04714657, filed Feb. 25, 2004, nine pages.

Shinn, et al. (Dec. 1, 2001) Database SPTREMBL [Online] XP002962732 Database accession No. (Q94F45).

Kaneko, T., et al. (Apr. 9, 1999) EMBL SEQ LIB EBI, Hinxton;"Structural analysis of *Arabidopsis thaliana* chromosome 5. XI.; P1 clone : MBA10" WWW.EBI.AC.UK acc. No. AB025619.

Rossini et al. 'The maize golden2 gene defines a novel class of transcriptional regulators in plants' The Plant Cell vol. 13, May 2001, pp. 1231-1244, XP002962733.

Rounsley et al. Aug. 4, 1997 (EMBL) *Arabidopsis thaliana* chromosome II BAC T13E15 genomic sequence, complete sequence XP002303794 Acc. No. AC002388, Pos. 557340-58040.

Kaneko et al. Mar. 1, 2001 (TREMBL) Transcription Factor Hap5a-like (At5g50480), *Arabidopsis thaliana* XP002302644 acc. No. Q9FGP7.

Kaneko et al. Apr. 19, 1999 (EMBL) "Structural analysis of *Arabidopsis thaliana* chromosome 5. XI.; P1 clone : MBA10" DNA Res. 6: 183-195.

Rounsley, et al. (EMBL) Sep. 12, 1997, "*Arabidopsis thaliana* mRNA for Hap3a transcription factor" accession No. Y 13723 XP-02315220.

U.S. Appl. No. 12/526,042, filed Feb. 7, 2008, Repetti, Petet P. et al.
U.S. Appl. No. 12/721,304, Creelman, Robert et al.
U.S. Appl. No. 12/988,789, filed Oct. 20, 2010, Chen, Jianxin, et al.
U.S. Appl. No. 12/689,010, filed Jan. 18, 2010, Powell, Ann L.T. et al.
U.S. Appl. No. 12/732,911, Armstrong, Joshua I. et al.
U.S. Appl. No. 12/917,303, filed Nov. 1, 2010, Jiang, C-Z., et al.
U.S. Appl. No. 12/922,834, filed Sep. 15, 2010, Khanna, Rajnish, et al.
U.S. Appl. No. 12/902,887, Armstrong, Joshua, et al.
U.S. Appl. No. 09/532,591, Samaha, R. et al.
U.S. Appl. No. 09/533,648, Riechmann, Jose Luis et al.
U.S. Appl. No. 10/290,627, Riechmann, Jose Luis et al.
U.S. Appl. No. 09/713,994, Keddie, James et al.
U.S. Appl. No. 09/837,944, Creelman, Robert et al.
U.S. Appl. No. 09/594,214, Jones, J. et al.
U.S. Appl. No. 10/456,882, Riechmann, Jose Luis et al.
U.S. Appl. No. 10/171,468, Creelman, Robert et al.
U.S. Appl. No. 09/394,519, Zhang, J. et al.
U.S. Appl. No. 09/627,348, Thomashow, Michael et al.
U.S. Appl. No. 09/489,376, Heard, J. et al.
U.S. Appl. No. 09/489,230, Broun, P. et al.
U.S. Appl. No. 09/506,720, Keddie, James et al.
U.S. Appl. No. 09/533,030, Keddie, James et al.
U.S. Appl. No. 09/533,392, Jiang, C-Z. et al.

\* cited by examiner

US 8,558,059 B2

GENES FOR CONFERRING TO PLANTS INCREASED TOLERANCE TO ENVIRONMENTAL STRESSES

The present application is a continuation of prior U.S. patent application Ser. No. 10/112,887, filed Mar. 18, 2002 (pending), incorporated herein by reference in its entirety; and the present application is a continuation-in-part of prior U.S. patent application Ser. No. 10/412,699, filed Apr. 10, 2003 (pending), which is a continuation-in-part of prior U.S. patent application Ser. No. 09/713,994, filed Nov. 16, 2000 (abandoned), which claims the benefit of prior U.S. Provisional Application No. 60/166,228, filed Nov. 17, 1999 (expired); and, the present application is a continuation-in-part of prior U.S. patent application Ser. No. 10/675,852, filed Sep. 30, 2003 (pending), which is a continuation-in-part of prior U.S. patent application Ser. No. 09/713,994, filed Nov. 16, 2000 (abandoned), which claims the benefit of prior U.S. Provisional Application No. 60/166,228, filed Nov. 17, 1999 (expired); and, the present application is a continuation-in-part of prior U.S. patent application Ser. No. 10/286,264, filed Nov. 1, 2002 (pending), which is a division of prior U.S. patent application Ser. No. 09/533,030, filed Mar. 22, 2000 (abandoned), which claims the benefit of prior U.S. Provisional Patent Application No. 60/125,814, filed Mar. 23, 1999 (expired); from all of which non-provisional applications priority is claimed under 35 U.S.C. §120; and the benefit of which provisional applications are claimed under 35 U.S.C. §119(e).

The claimed invention, in the field of functional genomics and the characterization of plant genes for the improvement of plants, was made by or on behalf of Mendel Biotechnology, Inc. and Monsanto Corporation as a result of activities undertaken within the scope of a joint research agreement, said agreement having been executed on Oct. 31, 1997, and in effect on or before the date the claimed invention was made.

JOINT RESEARCH AGREEMENT

The claimed invention, in the field of functional genomics and the characterization of plant genes for the improvement of plants, was made by or on behalf of Mendel Biotechnology, Inc. and Monsanto Company as a result of activities undertaken within the scope of a joint research agreement in effect on or before the date the claimed invention was made.

FIELD OF THE INVENTION AND INTRODUCTION

This invention relates to the field of plant biology. More particularly, the present invention pertains to compositions and methods for phenotypically modifying a plant.

A plant's traits, such as its biochemical, developmental, or phenotypic characteristics, can be controlled through a number of cellular processes. One important way to manipulate that control is through transcription factors—proteins that influence the expression of a particular gene or sets of genes. Transgenic plants that comprise cells having altered levels of at least one selected transcription factor, for example, possess advantageous or desirable traits. Strategies for manipulating traits by altering a plant cell's transcription factor content can therefore result in plants and crops with commercially valuable properties. Applicants have identified polynulceotides encoding transcription factors, developed numerous transgenic plants using these polynucleotides, and have analyzed the plants for a variety of important traits. In so doing, applicants have identified important polynucleotide and polypeptide sequences for producing commercially valuable plants and crops as well as the methods for making them and using them. Other aspects and embodiments of the invention are described below and can be derived from the teachings of this disclosure as a whole.

BACKGROUND OF THE INVENTION

Transcription factors can modulate gene expression, either increasing or decreasing (inducing or repressing) the rate of transcription. This modulation results in differential levels of gene expression at various developmental stages, in different tissues and cell types, and in response to different exogenous (e.g., environmental) and endogenous stimuli throughout the life cycle of the organism.

Because transcription factors are key controlling elements of biological pathways, altering the expression levels of one or more transcription factors can change entire biological pathways in an organism. For example, manipulation of the levels of selected transcription factors may result in increased expression of economically useful proteins or metabolic chemicals in plants or to improve other agriculturally relevant characteristics. Conversely, blocked or reduced expression of a transcription factor may reduce biosynthesis of unwanted compounds or remove an undesirable trait. Therefore, manipulating transcription factor levels in a plant offers tremendous potential in agricultural biotechnology for modifying a plant's traits.

The present invention provides novel transcription factors useful for modifying a plant's phenotype in desirable ways.

SUMMARY OF THE INVENTION

In a first aspect, the invention relates to a recombinant polynucleotide comprising a nucleotide sequence selected from the group consisting of: (a) a nucleotide sequence encoding a polypeptide comprising a polypeptide sequence selected from those of the Sequence Listing, SEQ ID NOs:2 and 4, or a complementary nucleotide sequence thereof; (b) a nucleotide sequence encoding a polypeptide comprising a variant of a polypeptide of (a) having one or more, or between 1 and about 5, or between 1 and about 10, or between 1 and about 30, conservative amino acid substitutions; (c) a nucleotide sequence comprising a sequence selected from those of SEQ ID NOs:1 and 3, or a complementary nucleotide sequence thereof; (d) a nucleotide sequence comprising silent substitutions in a nucleotide sequence of (c); (e) a nucleotide sequence which hybridizes under stringent conditions over substantially the entire length of a nucleotide sequence of one or more of: (a), (b), (c), or (d); (f) a nucleotide sequence comprising at least 10 or 15, or at least about 20, or at least about 30 consecutive nucleotides of a sequence of any of (a)-(e), or at least 10 or 15, or at least about 20, or at least about 30 consecutive nucleotides outside of a region encoding a conserved domain of any of (a)-(e); (g) a nucleotide sequence comprising a subsequence or fragment of any of (a)-(f), which subsequence or fragment encodes a polypeptide having a biological activity that modifies a plant's characteristic, functions as a transcription factor, or alters the level of transcription of a gene or transgene in a cell; (h) a nucleotide sequence having at least 31% sequence identity to a nucleotide sequence of any of (a)-(g); (i) a nucleotide sequence having at least 60%, or at least 70%, or at least 80%, or at least 90%, or at least 95% sequence identity to a nucleotide sequence of any of (a)-(g) or a 10 or 15 nucleotide, or at least about 20, or at least about 30 nucleotide region of a sequence of (a)-(g) that is outside of a region encoding a conserved domain; (j) a nucleotide sequence that encodes a polypeptide having at least 31% sequence identity to a polypeptide listed in the Sequence Listing or in Tables 6 and 7; (k) a nucleotide sequence which encodes a polypeptide having at least 60%, or at least 70%, or at least 80%, or at least 90%, or at least 95% sequence identity to a polypeptide listed in the Sequence Listing or in Tables 6 and 7; and (1) a nucleotide sequence that encodes a conserved domain of a polypeptide having at least 85%, or at least 90%, or at least 95%, or at least 98% sequence identity to a conserved domain of a polypeptide listed in the Sequence Listing or in Tables 6 and 7. The recombinant polynucleotide may further comprise a constitutive, inducible, or tissue-specific promoter operably linked to the nucleotide sequence. The invention also relates to compositions comprising at least two of the above-described polynucleotides.

In a second aspect, the invention comprises an isolated or recombinant polypeptide comprising a subsequence of at least about 10, or at least about 15, or at least about 20, or at least about 30 contiguous amino acids encoded by the recombinant or isolated polynucleotide described above, or comprising a subsequence of at least about 8, or at least about 12, or at least about 15, or at least about 20, or at least about 30 contiguous amino acids outside a conserved domain.

In a third aspect, the invention comprises an isolated or recombinant polynucleotide which encodes a polypeptide which is a paralog of the isolated polypeptide described in paragraph 6 above. In one aspect, the invention is an paralog which, when expressed in *Arabidopsis*, modifies a trait of the *Arabidopsis* plant.

In a fourth aspect, the invention comprises an isolated or recombinant polynucleotide which encodes a polypeptide which is an ortholog of the isolated polypeptide described in paragraph 6 above. In one aspect, the invention is an ortholog which, when expressed in *Arabidopsis*, modifies a trait of the *Arabidopsis* plant.

In a fifth aspect, the invention comprises an isolated or recombinant polynucleotide which encodes a polypeptide which is a paralog of the isolated polypeptide described in paragraph 6 above. In one aspect, the invention is an paralog which, when expressed in *Arabidopsis*, modifies a trait of the *Arabidopsis* plant.

In another aspect, the invention comprises an isolated polypeptide which is an ortholog of the isolated polypeptide described in paragraph 6 above. In one aspect, the invention is an ortholog which, when expressed in *Arabidopsis*, modifies a trait of the *Arabidopsis* plant.

In yet another aspect, the invention comprises an isolated synthetic polypeptide which is a homolog of the isolated polypeptide described in paragraph 6 above. In one aspect, the invention is a synthetic polypeptide which, when expressed in *Arabidopsis*, modifies a trait of the *Arabidopsis* plant.

In another aspect, the invention is a transgenic plant comprising one or more of the above-described recombinant polynucleotides. In yet another aspect, the invention is a plant with altered expression levels of a polynucleotide described above or a plant with altered expression or activity levels of an above-described polypeptide. Further, the invention is a plant lacking a nucleotide sequence encoding a polypeptide described above or substantially lacking a polypeptide described above. The plant may be any plant, including, but not limited to, *Arabidopsis*, mustard, soybean, wheat, corn, potato, cotton, rice, oilseed rape, sunflower, alfalfa, sugarcane, turf, banana, blackberry, blueberry, strawberry, raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, watermelon, rosaceous fruits, vegetable brassicas, and mint or other labiates. In yet another aspect, the inventions is an isolated plant material of a plant, including, but not limited to, plant tissue, fruit, seed, plant cell, embryo, protoplast, pollen, and the like. In yet another aspect, the invention is a transgenic plant tissue culture of regenerable cells, including, but not limited to, embryos, meristematic cells, microspores, protoplast, pollen, and the like.

In a further aspect the invention provides a method of using the polynucleotide composition to breed progeny from a parent plant including crossing plants, producing seeds from transgenic plants, and methods of breeding using transgenic plants.

In a further aspect, the invention provides a progeny plant derived from a parental plant wherein said progeny plant exhibits at least three fold greater messenger RNA levels than said parental plant, wherein the messenger RNA encodes a DNA-binding protein which is capable of binding to a DNA regulatory sequence and inducing expression of a plant trait gene, wherein the progeny plant is characterized by a change in the plant trait compared to said parental plant. In yet a further aspect, the progeny plant exhibits at least ten fold greater messenger RNA levels compared to said parental plant. In yet a further aspect, the progeny plant exhibits at least fifty fold greater messenger RNA levels compared to said parental plant.

In a further aspect, the invention relates to a cloning or expression vector comprising the isolated or recombinant polynucleotide described above or cells comprising the cloning or expression vector.

In yet a further aspect, the invention relates to a composition produced by incubating a polynucleotide of the invention with a nuclease, a restriction enzyme, a polymerase; a polymerase and a primer; a cloning vector, or with a cell.

Furthermore, the invention relates to a method for producing a plant having a modified trait. The method comprises altering the expression of an isolated or recombinant polynucleotide of the invention or altering the expression or activity of a polypeptide of the invention in a plant to produce a modified plant, and selecting the modified plant for a modified trait. In one aspect, the plant is a monocot plant. In another aspect, the plant is a dicot plant. In another aspect the recombinant polynucleotide is from a dicot plant and the plant is a monocot plant. In yet another aspect the recombinant polynucleotide is from a monocot plant and the plant is a dicot plant. In yet another aspect the recombinant polynucleotide is from a monocot plant and the plant is a monocot plant. In yet another aspect the recombinant polynucleotide is from a dicot plant and the plant is a dicot plant.

In another aspect, the invention relates to a method of identifying a factor that is modulated by or interacts with a polypeptide encoded by a polynucleotide of the invention. The method comprises expressing a polypeptide encoded by the polynucleotide in a plant; and identifying at least one factor that is modulated by or interacts with the polypeptide. In one embodiment the method for identifying modulating or interacting factors is by detecting binding by the polypeptide to a promoter sequence, or by detecting interactions between an additional protein and the polypeptide in a yeast two hybrid system, or by detecting expression of a factor by hybridization to a microarray, subtractive hybridization, or differential display.

In yet another aspect, the invention is a method of identifying a molecule that modulates activity or expression of a polynucleotide or polypeptide of interest. The method comprises placing the molecule in contact with a plant comprising the polynucleotide or polypeptide encoded by the polynucleotide of the invention and monitoring one or more of the expression level of the polynucleotide in the plant, the expression level of the polypeptide in the plant, and modulation of an activity of the polypeptide in the plant. In a further aspect, the invention is a method of using a molecule that modulates activity or expression of a polynucleotide or polypeptide of interest. The polynucleotide may be selected from the group comprising SEQ ID NOs:1 and 3, a variant or ortholog thereof. In the alternative, the polypeptide may be selected from the group comprising SEQ ID NOs:2 and 4, a variant or ortholog thereof. The method comprises placing the molecule in contact with a plant comprising the polynucleotide or polypeptide encoded by the polynucleotide of the invention and monitoring one or more of the expression level of the polynucleotide in the plant, the expression level of the polypeptide in the plant, and modulation of an activity of the polypeptide in the plant.

In yet another aspect, the invention relates to an integrated system, computer or computer readable medium comprising one or more character strings corresponding to a polynucleotide of the invention, or to a polypeptide encoded by the polynucleotide. The integrated system, computer or computer readable medium may comprise a link between one or more sequence strings to a modified plant trait.

In yet another aspect, the invention is a method for identifying a sequence similar or homologous to one or more polynucleotides of the invention, or one or more polypeptides encoded by the polynucleotides. The method comprises providing a sequence database, and querying the sequence database with one or more target sequences corresponding to the one or more polynucleotides or to the one or more polypeptides to identify one or more sequence members of the database that display sequence similarity or homology to one or more of the one or more target sequences.

The method may further comprise of linking the one or more of the polynucleotides of the invention, or encoded polypeptides, to a modified plant phenotype.

BRIEF DESCRIPTION OF THE SEQUENCE LISTING AND TABLES

The Sequence Listing provides exemplary polynucleotide and polypeptide sequences of the invention. The traits associated with the use of the sequences are included in the "Examples" section of the invention disclosure.

Tables 1 through 5 are shown and described in the invention disclosure.

Table 6 lists a summary of orthologous and homologous sequences of the polynucleotide sequences and polypeptide sequences of the invention (SEQ ID NOs:1-4) identified using BLAST (TBLASTX program). The first column shows the polynucleotide sequence identifier (SEQ ID NO), the second column shows the transcription factor cDNA identifier (Gene ID), the third column shows the orthologous or homologous polynucleotide GenBank Accession Number (Test Sequence ID), the fourth column shows the orthologous or homologous polynucleotide sequence identifier (Test Sequence SEQ ID NO), the fifth column shows the calculated probability value that the sequence identity is due to chance (Smallest Sum Probability), and the sixth column shows the orthologous or homologous GenBank annotation (Test Sequence GenBank Annotation).

Table 7 lists orthologous and homologous sequences of the polynucleotide sequences and polypeptide sequences of the invention (SEQ ID NOs:1-4) identified using BLAST (TBLASTX program). The first column shows the polynucleotide sequence identifier (SEQ ID NO), the second column shows the transcription factor cDNA identifier (Gene ID), the third column shows the orthologous or homologous polynucleotide GenBank Accession Number (Test Sequence ID), the fourth column shows the orthologous or homologous polynucleotide sequence GenBank annotation (Test Sequence GenBank Annotation) identifier (Test Sequence SEQ ID NO), the fifth column shows the reading frame of the Test sequence which encodes the orthologous or homologous sequence (Reading Frame), the sixth column shows the calculated score value of the aligned sequences (High Score), the seventh column shows the calculated probability value that the sequence identity is due to chance (Smallest Sum Probability), and the eighth column shows the number of regions of the orthologous or homologous Test Sequences which aligned with the sequence encoded by the transcription factor cDNA sequence GenBank annotation (N).

DETAILED DESCRIPTION OF EXEMPLARY EMBODIMENTS

In an important aspect, the present invention relates to polynucleotides and polypeptides, e.g. for modifying phenotypes of plants. Throughout this disclosure, various information sources are referred to and/or are specifically incorporated. The information sources include scientific journal articles, patent documents, textbooks, and world wide web browser-inactive page addresses, for example. While the reference to these information sources clearly indicates that they can be used by one of skill in the art, applicants specifically incorporate each and every one of the information sources cited herein, in their entirety, whether or not a specific mention of "incorporation by reference" is noted. The contents and teachings of each and every one of the information sources can be relied on and used to make and use embodiments of the invention.

It must be noted that as used herein and in the appended claims, the singular forms "a," "an," and "the" include plural reference unless the context clearly dictates otherwise. Thus, for example, a reference to "a plant" includes a plurality of such plants, and a reference to "a stress" is a reference to one or more stresses and equivalents thereof known to those skilled in the art, and so forth.

The polynucleotides of the invention encode plant transcription factors. As one of ordinary skill in the art recognizes, transcription factors can be identified by the presence of a region or domain of structural similarity or identity to a specific consensus sequence or the presence of a specific consensus DNA-binding site or DNA-binding site motif (see, for example, Riechmann et al., *Science* 290: 2105-2110 (2000)). The plant transcription factors may belong to one of the following transcription factor families: the AP2 (APETALA2) domain transcription factor family (Riechmann and Meyerowitz (1998) *Biol. Chem.* 379: 633-646); the MYB transcription factor family (Martin and Paz-Ares, (1997) *Trends Genet.* 13: 67-73); the MADS domain transcription factor family (Riechmann and Meyerowitz (1997) *Biol. Chem.* 378: 1079-1101); the WRKY protein family (Ishiguro and Nakamura (1994) *Mol. Gen. Genet.* 244: 563-571); the ankyrin-repeat protein family (Zhang et al. (1992) *Plant Cell* 4: 1575-1588); the zinc finger protein (Z) family (Klug and Schwabe (1995) *FASEB J.* 9: 597-604); the homeobox (HB) protein family (Duboule (1994) *Guidebook to the Homeobox Genes*, Oxford University Press); the CAAT-element binding proteins (Forsburg and Guarente (1989) *Genes Dev.* 3: 1166-1178); the squamosa promoter binding proteins (SPB) (Klein et al. (1996) *Mol. Gen. Genet.*

1996 250: 7-16); the NAM protein family (Souer et al. (1996) *Cell* 85: 159-170); the IAA/AUX proteins (Rouse et al. (1998) *Science* 279: 1371-1373); the HLH/MYC protein family (Littlewood et al. (1994) *Prot. Profile* 1: 639-709); the DNA-binding protein (DBP) family (Tucker et al. (1994) *EMBO J.* 13: 2994-3002); the bZIP family of transcription factors (Foster et al. (1994) *FASEB J* 8: 192-200); the Box P-binding protein (the BPF-1) family (da Costa e Silva et al. (1993) *Plant J.* 4: 125-135); the high mobility group (HMG) family (Bustin and Reeves (1996) *Prog. Nucl. Acids Res. Mol. Biol.* 54: 35-100); the scarecrow (SCR) family (Di Laurenzio et al. (1996) *Cell* 86: 423-433); the GF14 family (Wu et al. (1997) *Plant Physiol.* 114: 1421-1431); the polycomb (PCOMB) family (Kennison (1995) *Annu. Rev. Genet.* 29: 289-303); the teosinte branched (TEO) family (Luo et al. (1996) *Nature* 383: 794-799); the AB13 family (Giraudat et al. (1992) *Plant Cell* 4: 1251-1261); the triple helix (TH) family (Dehesh et al. (1990) *Science* 250: 1397-1399); the EIL family (Chao et al. (1997) *Cell* 89: 1133-44); the AT-HOOK family (Reeves and Nissen (1990) *Journal of Biological Chemistry* 265: 8573-8582); the SIFA family (Zhou et al. (1995) *Nucleic Acids Res.* 23: 1165-1169); the bZIPT2 family (Lu and Ferl (1995) *Plant Physiol.* 109: 723); the YABBY family (Bowman et al. (1999) *Development* 126: 2387-96); the PAZ family (Bohmert et al. (1998) *EMBO J.* 17: 170-80); miscellaneous (MISC) transcription factors including the DPBF family (Kim et al. (1997) *Plant J.* 11: 1237-1251) and the SPF1 family (Ishiguro and Nakamura (1994) *Mol. Gen. Genet.* 244: 563-571); the golden (GLD) family (Hall et al. (1998) *Plant Cell* 10: 925-936); the TUBBY family (Boggin et al, (1999) *Science* 286: 2119-2125); the heat shock family (Wu C (1995) *Annu Rev Cell Dev Biol* 11: 441-469); the ENBP family (Christiansen et al (1996) *Plant Mol Biol* 32: 809-821); the RING-zinc family (Jensen et al. (1998) *FEBS letters* 436: 283-287); the PDBP family (Janik et al *Virology.* (1989) 168: 320-329); the PCF family (Cubas P, et al. *Plant J.* (1999) 18: 215-22); the SRS(SHI-related) family (Fridborg et al *Plant Cell* (1999) 11: 1019-1032); the CPP (cysteine-rich polycomb-like) family (Cvitanich et al *Proc. Natl. Acad. Sci. USA*. (2000) 97: 8163-8168); the ARF (auxin response factor) family (Ulmasov, et al. (1999) *Proc. Natl. Acad. Sci. USA* 96: 5844-5849); the SWI/SNF family (Collingwood et al *J. Mol. End.* 23: 255-275); the ACBF family (Seguin et al *Plant Mol. Biol.* (1997) 35: 281-291); PCGL (CG-1 like) family (*Plant Mol. Biol.* (1994) 25: 921-924); the ARID family (Vazquez et al *Development.* (1999) 126: 733-42); the Jumonji family (Balciunas et al *Trends Biochem Sci*. (2000) 25: 274-276); the bZIP-NIN family (Schauser et al *Nature*. (1999) 402: 191-195); the E2F family Kaelin et al (1992) *Cell* 70: 351-364); and the GRF-like family (Knaap et al (2000) *Plant Physiol.* 122: 695-704. As indicated by any part of the list above and as known in the art, transcription factors have been sometimes categorized by class, family, and sub-family according to their structural content and consensus DNA-binding site motif, for example. Many of the classes and many of the families and sub-families are listed here. However, the inclusion of one sub-family and not another, or the inclusion of one family and not another, does not mean that the invention does not encompass polynucleotides or polypeptides of a certain family or sub-family. The list provided here is merely an example of the types of transcription factors and the knowledge available concerning the consensus sequences and consensus DNA-binding site motifs that help define them as known to those of skill in the art (each of the references noted above are specifically incorporated herein by reference). A transcription factor may include, but is not limited to, any polypeptide that can activate or repress transcription of a single gene or a number of genes. This polypeptide group includes, but is not limited to, DNA-binding proteins, DNA-binding protein binding proteins, protein kinases, protein phosphatases, GTP-binding proteins, and receptors, and the like.

In addition to methods for modifying a plant phenotype by employing one or more polynucleotides and polypeptides of the invention described herein, the polynucleotides and polypeptides of the invention have a variety of additional uses. These uses include their use in the recombinant production (i.e, expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like; as substrates for cloning e.g., including digestion or ligation reactions; and for identifying exogenous or endogenous modulators of the transcription factors.

A "polynucleotide" is a nucleic acid sequence comprising a plurality of polymerized nucleotides, e.g., at least about 15 consecutive polymerized nucleotide, optionally at least about 30 consecutive nucleotides, at least about 50 consecutive nucleotides. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single stranded or double stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

A "synthetic polynucleotide" is a polynucleotide not fund in nature and encodes a polypeptide not found in nature. The encoded polypeptide comprises at least four consecutive amino acid residues of a polypeptide found in nature.

An "isolated polynucleotide" is a polynucleotide whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

A "polypeptide" is an amino acid sequence comprising a plurality of consecutive polymerized amino acid residues e.g., at least about 15 consecutive polymerized amino acid residues, optionally at least about 30 consecutive polymerized amino acid residues, at least about 50 consecutive polymerized amino acid residues. In many instances, a polypeptide comprises a polymerized amino acid residue sequence which is a transcription factor or a domain or portion or fragment thereof. Additionally, the polypeptide may comprise a localization domain, 2) an activation domain, 3) a repression domain, 4) an oligomerization domain or 5) a DNA-binding domain, or the like. The polypeptide optionally comprises modified amino acid residues, naturally occurring amino acid residues not encoded by a codon, non-naturally occurring amino acid residues.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild type plant. Alternatively, or additionally, the isolated polypeptide is separated from other cellular components with which it is typically associated, e.g., by any of the various protein purification methods herein.

A "synthetic polypeptide" is a polypeptide not fund in nature and has activity of a polypeptide found in nature. The polypeptide comprises at least four consecutive amino acid residues of a polypeptide found in nature.

"Altered" nucleic acid sequences encoding polypeptide include those sequences with deletions, insertions, or substitutions of different nucleotides, resulting in a polynucleotide encoding a polypeptide with at least one functional characteristic of the polypeptide. Included within this definition are polymorphisms which may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide. The encoded polypeptide protein may also be "altered", and may contain deletions, insertions, or substitutions of amino acid residues which produce a silent change and result in a functionally equivalent polypeptide. Deliberate amino acid substitutions may be made on the basis of similarity in residue side chain chemistry, including, but not limited to, polarity, charge, solubility, hydrophobicity, hydrophilicity, and/or the amphipathic nature of the residues, as long as the biological activity of polypeptide is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. Alignments between different polypeptide sequences may be used to calculate "percentage sequence similarity".

The term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae. (See for example, Daly et al. 2001 Plant Physiology 127: 1328-1333; and also Tudge, C., The Variety of Life, Oxford University Press, New York, 2000, pp. 547-606.)

A "transgenic plant" refers to a plant that contains genetic material not found in a wild type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to appropriate inducible or constitutive regulatory sequences that allow for the expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Ectopic expression or altered expression" in reference to a polynucleotide indicates that the pattern of expression in, e.g., a transgenic plant or plant tissue, is different from the expression pattern in a wild type plant or a reference plant of the same species. The pattern of expression may also be compared with a reference expression pattern in a wild type plant of the same species. For example, the polynucleotide or polypeptide is expressed in a cell or tissue type other than a cell or tissue type in which the sequence is expressed in the wild type plant, or by expression at a time other than at the time the sequence is expressed in the wild type plant, or by a response to different inducible agents, such as hormones or environmental signals, or at different expression levels (either higher or lower) compared with those found in a wild type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

A "fragment" or "domain," with respect to a polypeptide, refers to a subsequence of the polypeptide. In some cases, the fragment or domain, is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions. Fragments can vary in size from as few as 6 amino acids to the full length of the intact polypeptide, but are preferably at least about 30 amino acids in length and more preferably at least about 60 amino acids in length. In reference to a polynucleotide sequence, "a fragment" refers to any subsequence of a polynucleotide, typically, of at least about 15 consecutive nucleotides, preferably at least about 30 nucleotides, more preferably at least about 50 nucleotides, of any of the sequences provided herein.

A "conserved domain", with respect to a polypeptide, refers to a domain within a transcription factor family which exhibits a higher degree of sequence homology, such as at least 65% sequence identity including conservative substitutions, and preferably at least 80% sequence identity, and more preferably at least 85%, or at least about 86%, or at least about 87%, or at least about 88%, or at least about 90%, or at least about 95%, or at least about 98% amino acid residue sequence identity of a polypeptide of consecutive amino acid residues. A fragment or domain can be referred to as outside a consensus sequence or outside a consensus DNA-binding site that is known to exist or that exists for a particular transcription factor class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. The conserved domains for each of polypeptides of SEQ ID NOs:2 and 4 are listed in Table 4 as described in Example VII. A comparison of the regions of the polypeptides in SEQ ID NOs:2 and 4 allows one of skill in the art to identify conserved domain(s) for any of the polypeptides listed or referred to in this disclosure, including those in Tables 6 and 7.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by the observation of the expression level of a gene or genes, e.g., by employing Northern analysis, RT-PCR, microarray gene expression assays, or reporter gene expression systems, or by agricultural observations such as stress tolerance, yield, or pathogen tolerance. Any technique can be used to measure the amount of, comparative level of, or difference in any selected chemical compound or macromolecule in the transgenic plants, however.

"Trait modification" refers to a detectable difference in a characteristic in a plant ectopically expressing a polynucleotide or polypeptide of the present invention relative to a plant not doing so, such as a wild type plant. In some cases, the trait modification can be evaluated quantitatively. For example, the trait modification can entail at least about a 2% increase or decrease in an observed trait (difference), at least a 5% difference, at least about a 10% difference, at least about a 20% difference, at least about a 30%, at least about a 50%, at least about a 70%, or at least about a 100%, or an even greater difference compared with a wild type plant. It is known that there can be a natural variation in the modified trait. Therefore, the trait modification observed entails a change of the normal distribution of the trait in the plants compared with the distribution observed in wild type plant.

Trait modifications of particular interest include those to seed (such as embryo or endosperm), fruit, root, flower, leaf, stem, shoot, seedling or the like, including: enhanced tolerance to environmental conditions including freezing, chilling, heat, drought, water saturation, radiation and ozone; improved tolerance to microbial, fungal or viral diseases; improved tolerance to pest infestations, including nematodes, mollicutes, parasitic higher plants or the like; decreased herbicide sensitivity; improved tolerance of heavy metals or enhanced ability to take up heavy metals; improved growth under poor photoconditions (e.g., low light and/or short day length), or changes in expression levels of genes of interest. Other phenotype that can be modified relate to the production of plant metabolites, such as variations in the production of taxol, tocopherol, tocotrienol, sterols, phytosterols, vitamins, wax monomers, anti-oxidants, amino acids, lignins, cellulose, tannins, prenyllipids (such as chlorophylls and carotenoids), glucosinolates, and terpenoids, enhanced or compositionally altered protein or oil production (especially in seeds), or modified sugar (insoluble or soluble) and/or starch composition. Physical plant characteristics that can be modified include cell development (such as the number of trichomes), fruit and seed size and number, yields of plant parts such as stems, leaves and roots, the stability of the seeds during storage, characteristics of the seed pod (e.g., susceptibility to shattering), root hair length and quantity, internode distances, or the quality of seed coat. Plant growth characteristics that can be modified include growth rate, germination rate of seeds, vigor of plants and seedlings, leaf and flower senescence, male sterility, apomixis, flowering time, flower abscission, rate of nitrogen uptake, biomass or transpiration characteristics, as well as plant architecture characteristics such as apical dominance, branching patterns, number of organs, organ identity, organ shape or size.

Examples of plant trait modifications and how to measure and determine those plant traits or characteristics are provided in the invention disclosure and the "Examples" section, Table 5. The disclosures are intended to illustrate but not limit which plant trait or characteristic may be modified by the invention.

Polypeptides and Polynucleotides of the Invention

The present invention provides, among other things, transcription factors (TFs), and transcription factor homologue polypeptides, and isolated or recombinant polynucleotides encoding the polypeptides, or novel variant polypeptides or polynucleotides encoding novel variants of transcription factors derived from the specific sequences provided here. These polypeptides and polynucleotides may be employed to modify a plant's characteristic.

Exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known transcription factors. In addition, further exemplary polynucleotides encoding the polypeptides of the invention were identified in the plant GenBank database using publicly available sequence analysis programs and parameters. Sequences initially identified were then further characterized to identify sequences comprising specified sequence strings corresponding to sequence motifs present in families of known transcription factors. Polynucleotide sequences meeting such criteria were confirmed as transcription factors.

Additional polynucleotides of the invention were identified by screening *Arabidopsis thaliana* and/or other plant cDNA libraries with probes corresponding to known transcription factors under low stringency hybridization conditions. Additional sequences, including full length coding sequences were subsequently recovered by the rapid amplification of cDNA ends (RACE) procedure, using a commercially available kit according to the manufacturer's instructions. Where necessary, multiple rounds of RACE are performed to isolate 5' and 3' ends. The full length cDNA was then recovered by a routine end-to-end polymerase chain reaction (PCR) using primers specific to the isolated 5' and 3' ends. Exemplary sequences are provided in the Sequence Listing.

The polynucleotides of the invention can be or were ectopically expressed in overexpressor or knockout plants and the changes in the characteristic(s) or trait(s) of the plants observed. Therefore, the polynucleotides and polypeptides can be employed to improve the characteristics of plants.

Producing Polypeptides

The polynucleotides of the invention include sequences that encode transcription factors and transcription factor homologue polypeptides and sequences complementary thereto, as well as unique fragments of coding sequence, or sequence complementary thereto. Such polynucleotides can be, e.g., DNA or RNA, e.g., mRNA, cRNA, synthetic RNA, genomic DNA, cDNA synthetic DNA, oligonucleotides, etc. The polynucleotides are either double-stranded or single-stranded, and include either, or both sense (i.e., coding) sequences and antisense (i.e., non-coding, complementary) sequences. The polynucleotides include the coding sequence of a transcription factor, or transcription factor homologue polypeptide, in isolation, in combination with additional coding sequences (e.g., a purification tag, a localization signal, as a fusion-protein, as a pre-protein, or the like), in combination with non-coding sequences (e.g., introns or inteins, regulatory elements such as promoters, enhancers, terminators, and the like), and/or in a vector or host environment in which the polynucleotide encoding a transcription factor or transcription factor homologue polypeptide is an endogenous or exogenous gene.

A variety of methods exist for producing the polynucleotides of the invention. Procedures for identifying and isolating DNA clones are well known to those of skill in the art, and are described in, e.g., Berger and Kimmel, *Guide to Molecular Cloning Techniques, Methods in Enzymology* volume 152 Academic Press, Inc., San Diego, Calif. ("Berger"); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2000) ("Ausubel").

Alternatively, polynucleotides of the invention, can be produced by a variety of in vitro amplification methods adapted to the present invention by appropriate selection of specific or degenerate primers. Examples of protocols sufficient to direct persons of skill through in vitro amplification methods, including the polymerase chain reaction (PCR) the ligase chain reaction (LCR), Qbeta-replicase amplification and other RNA polymerase mediated techniques (e.g., NASBA), e.g., for the production of the homologous nucleic acids of the invention are found in Berger, Sambrook, and Ausubel (all supra), as well as Mullis et al., (1987) *PCR Protocols A Guide to Methods and Applications* (Innis et al. eds) Academic Press Inc. San Diego, Calif. (1990) (Innis). Improved methods for cloning in vitro amplified nucleic acids are described in Wallace et al., U.S. Pat. No. 5,426,039. Improved methods for amplifying large nucleic acids by PCR are summarized in Cheng et al. (1994) *Nature* 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

Alternatively, polynucleotides and oligonucleotides of the invention can be assembled from fragments produced by solid-phase synthesis methods. Typically, fragments of up to approximately 100 bases are individually synthesized and then enzymatically or chemically ligated to produce a desired sequence, e.g., a polynucletotide encoding all or part of a transcription factor. For example, chemical synthesis using the phosphoramidite method is described, e.g., by Beaucage et al. (1981) *Tetrahedron Letters* 22: 1859-69; and Matthes et al. (1984) *EMBO J.* 3: 801-5. According to such methods, oligonucleotides are synthesized, purified, annealed to their complementary strand, ligated and then optionally cloned into suitable vectors. And if so desired, the polynucleotides and polypeptides of the invention can be custom ordered from any of a number of commercial suppliers.

Homologous Sequences

Sequences homologous, i.e., that share significant sequence identity or similarity, to those provided in the Sequence Listing, derived from *Arabidopsis thaliana* or from other plants of choice are also an aspect of the invention. Homologous sequences can be derived from any plant including monocots and dicots and in particular agriculturally important plant species, including but not limited to, crops such as soybean, wheat, corn, potato, cotton, rice, oilseed rape (including canola), sunflower, alfalfa, sugarcane and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, watermelon, rosaceous fruits (such as apple, peach, pear, cherry and plum) and vegetable brassicas (such as broccoli, cabbage, cauliflower, brussel sprouts and kohlrabi). Other crops, fruits and vegetables whose phenotype can be changed include barley, rye, millet, sorghum, currant, avocado, citrus fruits such as oranges, lemons, grapefruit and tangerines, artichoke, cherries, nuts such as the walnut and peanut, endive, leek, roots, such as arrowroot, beet, cassaya, turnip, radish, yam, and sweet potato, and beans. The homologous sequences may also be derived from woody species, such pine, poplar and eucalyptus, or mint or other labiates.

Transcription factors that are homologous to the listed sequences will typically share at least about 30% amino acid sequence identity, or at least about 30% amino acid sequence identity outside of a known consensus sequence or consensus DNA-binding site. More closely related transcription factors can share at least about 50%, about 60%, about 65%, about 70%, about 75% or about 80% or about 90% or about 95% or about 98% or more sequence identity with the listed sequences, or with the listed sequences but excluding or outside a known consensus sequence or consensus DNA-binding site, or with the listed sequences excluding one or all conserved domain. Factors that are most closely related to the listed sequences share, e.g., at least about 85%, about 90% or about 95% or more % sequence identity to the listed sequences, or to the listed sequences but excluding or outside a known consensus sequence or consensus DNA-binding site or outside one or all conserved domain. At the nucleotide level, the sequences will typically share at least about 40% nucleotide sequence identity, preferably at least about 50%, about 60%, about 70% or about 80% sequence identity, and more preferably about 85%, about 90%, about 95% or about 97% or more sequence identity to one or more of the listed sequences, or to a listed sequence but excluding or outside a known consensus sequence or consensus DNA-binding site, or outside one or all conserved domain. The degeneracy of the genetic code enables major variations in the nucleotide sequence of a polynucleotide while maintaining the amino acid sequence of the encoded protein. Conserved domains within a transcription factor family may exhibit a higher degree of sequence homology, such as at least 65% sequence identity including conservative substitutions, and preferably at least 80% sequence identity, and more preferably at least 85%, or at least about 86%, or at least about 87%, or at least about 88%, or at least about 90%, or at least about 95%, or at least about 98% sequence identity. Transcription factors that are homologous to the listed sequences should share at least 30%, or at least about 60%, or at least about 75%, or at least about 80%, or at least about 90%, or at least about 95% amino acid sequence identity over the entire length of the polypeptide or the homolog. In addition, transcription factors that are homologous to the listed sequences should share at least 30%, or at least about 60%, or at least about 75%, or at least about 80%, or at least about 90%, or at least about 95% amino acid sequence similarity over the entire length of the polypeptide or the homolog.

Identifying Orthologs and Paralogs

Several different methods are known by those of skill in the art for identifying and defining these functionally homologous sequences. Three general methods for defining paralogs and orthologs are described; a paralog or ortholog may be identified by only one or more of the methods described below.

Orthologs and paralogs are evolutionarily related genes that have similar sequence and similar functions. Paralogs are related genes within a single species and are most likely a result of gene duplication, whereas orthologs are related genes in different species derived from a common ancestral molecule prior to speciation.

Within a single plant species, gene duplication may causes two copies of a particular gene, giving rise to two or more genes with similar sequence and similar function known as paralogs. A paralog is therefore a similar gene with a similar function within the same species. Paralogs typically cluster together or in the same lade (a group of similar genes) when a gene family phylogeny is analyzed using programs such as CLUSTAL (Thompson et al. (1994) Nucleic Acids Res. 22: 4673-4680; Higgins et al. (1996) Methods Enzymol. 266 383-402). Groups of similar genes can also be identified using by pair-wise BLAST analysis (Feng and Doolittle (1987) J. Mol. Evol. 25: 351-360). For example, a clade of very similar MADS domain transcription factors from *Arabidopsis* all share a common function in flowering time (Ratcliffe et al. (2001) Plant Physiol. 126: 122-132), and a group of very similar AP2 domain transcription factors from *Arabidopsis* are involved in tolerance of plants to freezing (Gilmour et al. (1998) Plant J. 16: 433-442). Analysis of groups of similar genes with similar function that fall within one clade can yield sub-sequences that are particular to the clade. These sub-sequences, known as consensus sequences, can not only be used to define the sequences within each lade, but define the functions of these genes, since genes within each clade typically share the same function. (See also, for example, Mount, D. W. (2001) *Bioinformatics: Sequence and Genome Analysis* Cold Spring Harbor Laboratory Press, Cold Spring Harbor, N.Y. page 543.)

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994) Nucleic Acids Res. 22: 4673-4680; Higgins et al. (1996) Methods Enzymol. 266: 383-402), potential orthologous sequences can placed into the phylogenetic tree and its relationship to genes from the species of interest can be determined. Once the ortholog pair has been identified, the function of the test ortholog can be determined by determining the function of the reference ortholog.

Orthologs can also be identified by pair-wise BLAST analysis by aligning a set of reference sequences against a set of test sequences. Test sequences with the closest match to a particular reference sequence, as determined by the P-value of the BLAST analysis, can be taken and individually aligned against the reference set of sequences. The individual test sequence will either best match the particular reference sequence, in which case it is likely to be an ortholog, or not, in which case it may not be an ortholog.

A further way of identifying an ortholog is by identifying a consensus sequence within the candidate ortholog. Using pair-wise BLAST analysis, or programs such as CLUSTAL alignment program, sets of similar genes, or clades, can be identified. The particular sub-sequences which defining within a particular lade have in common to differentiate themselves can be derived from an alignment of those sequences. Orthologs would have the consensus sequence, or a sequence similar to the consensus sequence. Orthologs might also have a consensus sequence outside a conserved domain, which could be particular to that family of orthologous sequences.

Corresponding orthologs may bridge the monocot/dicot division of the plant kingdom and orthologous pairs of genes can be identified in rice and *Arabidopsis*, corn and *Arabidopsis* and *Antirhinnum* and corn. For example Peng et al showed that a mutant of the *Arabidopsis* gene termed Gibberellin Insensitive (GAI; mutant termed gai) encoded a transcription factor and which conferred a reduction in gibberellin responsiveness in the native plant (Peng et al. 1997 Genes and Development 11: 3194-3205). In addition, Peng et al. subsequently showed that the *Arabidopsis* GAI protein has 62% amino acid residue identity with the wheat Rht-D1a protein and 62% amino acid residue identity with the maize d8. Peng et al. showed that transgenic rice plants containing a mutant GAI allele give reduced response to gibberellin and are dwarfed, mimicking the dwarfed wheat variety from which the mutant Rht-D1a gene was isolated. Peng et al. taught that *Arabidopsis* GAI protein is an ortholog of the wheat Rht-D1a and maize d8 proteins. (Peng et al. 1999 Nature 400: 256-261.)

In addition Fu et al. (2001 Plant Cell 13: 1791-1802), Nandi et al. (2000 Curr. Biol. 10: 215-218), Coupland (1995 Nature 377: 482-483), and Weigel and Nilsson (1995 Nature 377: 482-500) show that an *Arabidopsis* transcription factor expressed in an exogenous plant species elicits the same or very similar phenotypic response. Furthermore, Mandel et al. (1992 Cell 71-133-143) and Suzuki et al. (2001 Plant J. 28: 409-418) showed that a transcription factor expressed in another plant species elicits the same or very similar phenotypic response of the endogenous sequence, as often predicted in earlier studies of *Arabidopsis* transcription factors in *Arabidopsis*.

Identifying Polynucleotides or Nucleic Acids by Hybridization

Polynucleotides homologous to the sequences illustrated in the Sequence Listing can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number), as described in more detail in the references cited above.

An example of stringent hybridization conditions for hybridization of complementary nucleic acids which have more than 100 complementary residues on a filter in a Southern or northern blot is about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Nucleic acid molecules that hybridize under stringent conditions will typically hybridize to a probe based on either the entire cDNA or selected portions, e.g., to a unique subsequence, of the cDNA under wash conditions of 0.2×SSC to 2.0×SSC, 0.1% SDS at 50-65° C. For example, high stringency is about 0.2×SSC, 0.1% SDS at 65° C. Ultra-high stringency will be the same conditions except the wash temperature is raised about 3 or about 5° C., and ultra-ultra-high stringency will be the same conditions except the wash temperature is raised about 6 or about 9° C. For identification of less closely related homologues washes can be performed at a lower temperature, e.g., 50° C. In general, stringency is increased by raising the wash temperature and/or decreasing the concentration of SSC, as known in the art.

As another example, stringent conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a transcription factor known as of the filing date of the application. Conditions can be selected such that a higher signal to noise ratio is observed in the particular assay which is used, e.g., about 15×, 25×, 35×, 50× or more. Accordingly, the subject nucleic acid hybridizes to the unique coding oligonucleotide with at least a 2× higher signal to noise ratio as compared to hybridization of the coding oligonucleotide to a nucleic acid encoding known polypeptide. Again, higher signal to noise ratios can be selected, e.g., about 5×, 10×, 25×, 35×, 50× or more. The particular signal will depend on the label used in the relevant assay, e.g., a fluorescent label, a calorimetric label, a radioactive label, or the like.

Alternatively, transcription factor homolog polypeptides can be obtained by screening an expression library using antibodies specific for one or more transcription factors. With the provision herein of the disclosed transcription factor, and transcription factor homologue nucleic acid sequences, the encoded polypeptide(s) can be expressed and purified in a heterologous expression system (e.g., *E. coli*) and used to raise antibodies (monoclonal or polyclonal) specific for the polypeptide(s) in question. Antibodies can also be raised against synthetic peptides derived from transcription factor, or transcription factor homologue, amino acid sequences. Methods of raising antibodies are well known in the art and are described in Harlow and Lane (1988) *Antibodies: A Laboratory Manual*, Cold Spring Harbor Laboratory, New York. Such antibodies can then be used to screen an expression library produced from the plant from which it is desired to clone additional transcription factor homologues, using the methods described above. The selected cDNAs can be confirmed by sequencing and enzymatic activity.

Sequence Variations

It will readily be appreciated by those of skill in the art, that any of a variety of polynucleotide sequences are capable of encoding the transcription factors and transcription factor homologue polypeptides of the invention. Due to the degeneracy of the genetic code, many different polynucleotides can encode identical and/or substantially similar polypeptides in addition to those sequences illustrated in the Sequence Listing.

For example, Table 1 illustrates, e.g., that the codons AGC, AGT, TCA, TCC, TCG, and TCT all encode the same amino acid: serine. Accordingly, at each position in the sequence where there is a codon encoding serine, any of the above trinucleotide sequences can be used without altering the encoded polypeptide.

TABLE 1

| Amino acid | | | Possible Codons |
|---|---|---|---|
| Alanine | Ala | A | GCA GCC GCG GCU |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC AGT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

Sequence alterations that do not change the amino acid sequence encoded by the polynucleotide are termed "silent" variations. With the exception of the codons ATG and TGG, encoding methionine and tryptophan, respectively, any of the possible codons for the same amino acid can be substituted by a variety of techniques, e.g., site-directed mutagenesis, available in the art. Accordingly, any and all such variations of a sequence selected from the above table are a feature of the invention.

In addition to silent variations, other conservative variations that alter one, or a few amino acids in the encoded polypeptide, can be made without altering the function of the polypeptide, these conservative variants are, likewise, a feature of the invention.

For example, substitutions, deletions and insertions introduced into the sequences provided in the Sequence Listing are also envisioned by the invention. Such sequence modifications can be engineered into a sequence by site-directed mutagenesis (Wu (ed.) *Meth. Enzymol.* (1993) vol. 217, Academic Press) or the other methods noted below. Amino acid substitutions are typically of single residues; insertions usually will be on the order of about from 1 to 10 amino acid residues; and deletions will range about from 1 to 30 residues. In preferred embodiments, deletions or insertions are made in adjacent pairs, e.g., a deletion of two residues or insertion of two residues. Substitutions, deletions, insertions or any combination thereof can be combined to arrive at a sequence. The mutations that are made in the polynucleotide encoding the transcription factor should not place the sequence out of reading frame and should not create complementary regions that could produce secondary mRNA structure. Preferably, the polypeptide encoded by the DNA performs the desired function.

Conservative substitutions are those in which at least one residue in the amino acid sequence has been removed and a different residue inserted in its place. Such substitutions generally are made in accordance with the Table 2 when it is desired to maintain the activity of the protein. Table 2 shows amino acids which can be substituted for an amino acid in a protein and which are typically regarded as conservative substitutions.

TABLE 2

| Residue | Conservative Substitutions |
| --- | --- |
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Similar substitutions are those in which at least one residue in the amino acid sequence has been removed and a different residue inserted in its place. Such substitutions generally are made in accordance with the Table 3 when it is desired to maintain the activity of the protein. Table 3 shows amino acids which can be substituted for an amino acid in a protein and which are typically regarded as structural and functional substitutions. For example, a residue in column 1 of Table 3 may be substituted with residue in column 2; in addition, a residue in column 2 of Table 3 may be substituted with the residue of column 1.

TABLE 3

| Residue | Similar Substitutions |
| --- | --- |
| Ala | Ser; Thr; Gly; Val; Leu; Ile |
| Arg | Lys; His; Gly |

TABLE 3-continued

| Residue | Similar Substitutions |
| --- | --- |
| Asn | Gln; His; Gly; Ser; Thr |
| Asp | Glu, Ser; Thr |
| Gln | Asn; Ala |
| Cys | Ser; Gly |
| Glu | Asp |
| Gly | Pro; Arg |
| His | Asn; Gln; Tyr; Phe; Lys; Arg |
| Ile | Ala; Leu; Val; Gly; Met |
| Leu | Ala; Ile; Val; Gly; Met |
| Lys | Arg; His; Gln; Gly; Pro |
| Met | Leu; Ile; Phe |
| Phe | Met; Leu; Tyr; Trp; His; Val; Ala |
| Ser | Thr; Gly; Asp; Ala; Val; Ile; His |
| Thr | Ser; Val; Ala; Gly |
| Trp | Tyr; Phe; His |
| Tyr | Trp; Phe; His |
| Val | Ala; Ile; Leu; Gly; Thr; Ser; Glu |

Substitutions that are less conservative than those in Table 2 or Table 3 can be selected by picking residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Further Modifying Sequences of the Invention—Mutation/Forced Evolution

In addition to generating silent or conservative substitutions as noted, above, the present invention optionally includes methods of modifying the sequences of the Sequence Listing. In the methods, nucleic acid or protein modification methods are used to alter the given sequences to produce new sequences and/or to chemically or enzymatically modify given sequences to change the properties of the nucleic acids or proteins. These sequences may be synthetic polynuceotides and synthetic polypetides.

Thus, in one embodiment, given nucleic acid sequences are modified, e.g., according to standard mutagenesis or artificial evolution methods to produce modified sequences. For example, Ausubel, supra, provides additional details on mutagenesis methods. Artificial forced evolution methods are described, e.g., by Stemmer (1994) *Nature* 370: 389-391, and Stemmer (1994) *Proc. Natl. Acad. Sci. USA* 91: 10747-10751, and U.S. Pat. Nos. 5,811,238, 5,837,500, and 6,242,568. Many other mutation and evolution methods are also available and expected to be within the skill of the practitioner. A synthetic polypeptide encoded by a synthetic polynucleotide may have as little as 20% amino acid residue sequence identity to the polypeptide encoded by the claimed polynucleotides and still modify a plant's trait or characteristic.

Similarly, chemical or enzymatic alteration of expressed nucleic acids and polypeptides can be performed by standard methods. For example, sequence can be modified by addition of lipids, sugars, peptides, organic or inorganic compounds, by the inclusion of modified nucleotides or amino acids, or the like. For example, protein modification techniques are illustrated in Ausubel, supra. Further details on chemical and enzymatic modifications can be found herein. These modification methods can be used to modify any given sequence, or to modify any sequence produced by the various mutation and artificial evolution modification methods noted herein.

Accordingly, the invention provides for modification of any given nucleic acid by mutation, evolution, chemical or enzymatic modification, or other available methods, as well as for the products produced by practicing such methods, e.g., using the sequences herein as a starting substrate for the various modification approaches.

For example, optimized coding sequence containing codons preferred by a particular prokaryotic or eukaryotic host can be used e.g., to increase the rate of translation or to produce recombinant RNA transcripts having desirable properties, such as a longer half-life, as compared with transcripts produced using a non-optimized sequence. Translation stop codons can also be modified to reflect host preference. For example, preferred stop codons for S. cerevisiae and mammals are TAA and TGA, respectively. The preferred stop codon for monocotyledonous plants is TGA, whereas insects and E. coli prefer to use TAA as the stop codon.

The polynucleotide sequences of the present invention can also be engineered in order to alter a coding sequence for a variety of reasons, including but not limited to, alterations which modify the sequence to facilitate cloning, processing and/or expression of the gene product. For example, alterations are optionally introduced using techniques which are well known in the art, e.g., site-directed mutagenesis, to insert new restriction sites, to alter glycosylation patterns, to change codon preference, to introduce splice sites, etc.

Furthermore, a fragment or domain derived from any of the polypeptides of the invention can be combined with domains derived from other transcription factors or synthetic domains to modify the biological activity of a transcription factor. For instance, a DNA-binding domain derived from a transcription factor of the invention can be combined with the activation domain of another transcription factor or with a synthetic activation domain. A transcription activation domain assists in initiating transcription from a DNA-binding site. Examples include the transcription activation region of VP16 or GAL4 (Moore et al. (1998) *Proc. Natl. Acad. Sci. USA* 95: 376-381; and Aoyama et al. (1995) *Plant Cell* 7: 1773-1785), peptides derived from bacterial sequences (Ma and Ptashne (1987) *Cell* 51; 113-119) and synthetic peptides (Giniger and Ptashne, (1987) *Nature* 330: 670-672).

Expression and Modification of Polypeptides

Typically, polynucleotide sequences of the invention are incorporated into recombinant DNA (or RNA) molecules that direct expression of polypeptides of the invention in appropriate host cells, transgenic plants, in vitro translation systems, or the like. Due to the inherent degeneracy of the genetic code, nucleic acid sequences which encode substantially the same or a functionally equivalent amino acid sequence can be substituted for any listed sequence to provide for cloning and expressing the relevant homologue.

Vectors, Promoters, and Expression Systems

The present invention includes recombinant constructs comprising one or more of the nucleic acid sequences herein. The constructs typically comprise a vector, such as a plasmid, a cosmid, a phage, a virus (e.g., a plant virus), a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts which describe molecular biological techniques useful herein, including the use and production of vectors, promoters and many other relevant topics, include Berger, Sambrook and Ausubel, supra. Any of the identified sequences can be incorporated into a cassette or vector, e.g., for expression in plants. A number of expression vectors suitable for stable transformation of plant cells or for the establishment of transgenic plants have been described including those described in Weissbach and Weissbach, (1989) *Methods for Plant Molecular Biology*, Academic Press, and Gelvin et al., (1990) *Plant Molecular Biology Manual*, Kluwer Academic Publishers. Specific examples include those derived from a Ti plasmid of *Agrobacterium tumefaciens*, as well as those disclosed by Herrera-Estrella et al. (1983) *Nature* 303: 209, Bevan (1984) *Nucl Acid Res.* 12: 8711-8721, Klee (1985) *Bio/Technology* 3: 637-642, for dicotyledonous plants.

Alternatively, non-Ti vectors can be used to transfer the DNA into monocotyledonous plants and cells by using free DNA delivery techniques. Such methods can involve, for example, the use of liposomes, electroporation, microprojectile bombardment, silicon carbide whiskers, and viruses. By using these methods transgenic plants such as wheat, rice (Christou (1991) *Bio/Technology* 9: 957-962) and corn (Gordon-Kamm (1990) *Plant Cell* 2: 603-618) can be produced. An immature embryo can also be a good target tissue for monocots for direct DNA delivery techniques by using the particle gun (Weeks et al. (1993) *Plant Physiol* 102: 1077-1084; Vasil (1993) *Bio/Technology* 10: 667-674; Wan and Lemeaux (1994) *Plant Physiol* 104: 37-48, and for *Agrobacterium*-mediated DNA transfer (Ishida et al. (1996) *Nature Biotech* 14: 745-750).

Typically, plant transformation vectors include one or more cloned plant coding sequence (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally- or developmentally-regulated, or cell- or tissue-specific expression), a transcription initiation start site, an RNA processing signal (such as intron splice sites), a transcription termination site, and/or a polyadenylation signal.

Examples of constitutive plant promoters which can be useful for expressing the TF sequence include: the cauliflower mosaic virus (CaMV) 35S promoter, which confers constitutive, high-level expression in most plant tissues (see, e.g., Odel et al. (1985) *Nature* 313: 810); the nopaline synthase promoter (An et al. (1988) *Plant Physiol* 88: 547); and the octopine synthase promoter (Fromm et al. (1989) *Plant Cell* 1: 977).

A variety of plant gene promoters that regulate gene expression in response to environmental, hormonal, chemical, developmental signals, and in a tissue-active manner can be used for expression of a TF sequence in plants. Choice of a promoter is based largely on the phenotype of interest and is determined by such factors as tissue (e.g., seed, fruit, root, pollen, vascular tissue, flower, carpel, etc.), inducibility (e.g., in response to wounding, heat, cold, drought, light, pathogens, etc.), timing, developmental stage, and the like. Numerous known promoters have been characterized and can favorable be employed to promote expression of a polynucleotide of the invention in a transgenic plant or cell of interest. For example, tissue specific promoters include: seed-specific promoters (such as the napin, phaseolin or DC3 promoter described in U.S. Pat. No. 5,773,697), fruit-specific promoters that are active during fruit ripening (such as the dru 1 promoter (U.S. Pat. No. 5,783,393), or the 2A11 promoter (U.S. Pat. No. 4,943,674) and the tomato polygalacturonase promoter (Bird et al. (1988) *Plant Mol Biol* 11: 651), root-specific promoters, such as those disclosed in U.S. Pat. Nos. 5,618,988, 5,837,848 and 5,905,186, pollen-active promoters such as PTA29, PTA26 and PTA13 (U.S. Pat. No. 5,792,929), promoters active in vascular tissue (Ringli and Keller (1998) *Plant Mol Biol* 37: 977-988), flower-specific (Kaiser et al, (1995) *Plant Mol Biol* 28: 231-243), pollen (Baerson et al. (1994) *Plant Mol Biol* 26: 1947-1959), carpels (Ohl et al. (1990) *Plant Cell* 2: 837-848), pollen and ovules (Baerson et al. (1993) *Plant Mol Biol* 22: 255-267), auxin-inducible promoters (such as that described in van der Kop et al. (1999) *Plant Mol Biol* 39: 979-990 or Baumann et al. (1999) *Plant Cell* 11: 323-334), cytokinin-inducible promoter (Guevara-Garcia (1998) *Plant Mol Biol* 38: 743-753), promoters responsive to gibberellin (Shi et al. (1998) *Plant Mol Biol* 38: 1053-1060, Willmott et al. (1998) 38: 817-825) and the like. Additional promoters are those that elicit expression in response to heat (Ainley et al. (1993) *Plant Mol Biol* 22: 13-23), light (e.g., the pea rbcS-3A promoter, Kuhlemeier et al. (1989) *Plant Cell* 1: 471, and the maize rbcS promoter, Schaffner and Sheen (1991) *Plant Cell* 3: 997); wounding (e.g., wunI, Siebertz et al. (1989) *Plant Cell* 1: 961); pathogens (such as the PR-1 promoter described in Buchel et al. (1999) *Plant Mol. Biol.* 40: 387-396, and the PDF1.2 promoter described in Manners et al. (1998) *Plant Mol. Biol.* 38: 1071-80), and chemicals such as methyl jasmonate or salicylic acid (Gatz et al. (1997) *Annu Rev Plant Physiol Plant Mol Biol* 48: 89-108). In addition, the timing of the expression can be controlled by using promoters such as those acting at senescence (Gan and Amasino (1995) *Science* 270: 1986-1988); or late seed development (Odell et al. (1994) *Plant Physiol* 106: 447-458).

Plant expression vectors can also include RNA processing signals that can be positioned within, upstream or downstream of the coding sequence. In addition, the expression vectors can include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Additional Expression Elements

Specific initiation signals can aid in efficient translation of coding sequences. These signals can include, e.g., the ATG initiation codon and adjacent sequences. In cases where a coding sequence, its initiation codon and upstream sequences are inserted into the appropriate expression vector, no additional translational control signals may be needed. However, in cases where only coding sequence (e.g., a mature protein coding sequence), or a portion thereof, is inserted, exogenous transcriptional control signals including the ATG initiation codon can be separately provided. The initiation codon is provided in the correct reading frame to facilitate transcription. Exogenous transcriptional elements and initiation codons can be of various origins, both natural and synthetic. The efficiency of expression can be enhanced by the inclusion of enhancers appropriate to the cell system in use.

Expression Hosts

The present invention also relates to host cells which are transduced with vectors of the invention, and the production of polypeptides of the invention (including fragments thereof) by recombinant techniques. Host cells are genetically engineered (i.e, nucleic acids are introduced, e.g., transduced, transformed or transfected) with the vectors of this invention, which may be, for example, a cloning vector or an expression vector comprising the relevant nucleic acids herein. The vector is optionally a plasmid, a viral particle, a phage, a naked nucleic acid, etc. The engineered host cells can be cultured in conventional nutrient media modified as appropriate for activating promoters, selecting transformants, or amplifying the relevant gene. The culture conditions, such as temperature, pH and the like, are those previously used with the host cell selected for expression, and will be apparent to those skilled in the art and in the references cited herein, including, Sambrook and Ausubel.

The host cell can be a eukaryotic cell, such as a yeast cell, or a plant cell, or the host cell can be a prokaryotic cell, such as a bacterial cell. Plant protoplasts are also suitable for some applications. For example, the DNA fragments are introduced into plant tissues, cultured plant cells or plant protoplasts by standard methods including electroporation (Fromm et al., (1985) *Proc. Natl. Acad. Sci. USA* 82, 5824, infection by viral vectors such as cauliflower mosaic virus (CaMV) (Hohn et al., (1982) *Molecular Biology of Plant Tumors*, (Academic Press, New York) pp. 549-560; U.S. Pat. No. 4,407,956), high velocity ballistic penetration by small particles with the nucleic acid either within the matrix of small beads or particles, or on the surface (Klein et al., (1987) *Nature* 327, 70-73), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233: 496-498; Fraley et al. (1983) *Proc. Natl. Acad. Sci. USA* 80, 4803).

The cell can include a nucleic acid of the invention which encodes a polypeptide, wherein the cells expresses a polypeptide of the invention. The cell can also include vector sequences, or the like. Furthermore, cells and transgenic plants which include any polypeptide or nucleic acid above or throughout this specification, e.g., produced by transduction of a vector of the invention, are an additional feature of the invention.

For long-term, high-yield production of recombinant proteins, stable expression can be used. Host cells transformed with a nucleotide sequence encoding a polypeptide of the invention are optionally cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding mature proteins of the invention can be designed with signal sequences which direct secretion of the mature polypeptides through a prokaryotic or eukaryotic cell membrane.

Modified Amino Acids

Polypeptides of the invention may contain one or more modified amino acids. The presence of modified amino acids may be advantageous in, for example, increasing polypeptide half-life, reducing polypeptide antigenicity or toxicity, increasing polypeptide storage stability, or the like. Amino acid(s) are modified, for example, co-translationally or post-translationally during recombinant production or modified by synthetic or chemical means.

Non-limiting examples of a modified amino acid include incorporation or other use of acetylated amino acids, glycosylated amino acids, sulfated amino acids, prenylated (e.g., farnesylated, geranylgeranylated) amino acids, PEG modified (e.g., "PEGylated") amino acids, biotinylated amino acids, carboxylated amino acids, phosphorylated amino acids, etc. References adequate to guide one of skill in the modification of amino acids are replete throughout the literature.

The modified amino acids may prevent or increase affinity of the polypeptide for another molecule, including, but not limited to, polynucleotide, proteins, carbohydrates, lipids and lipid derivatives, and other organic or synthetic compounds.

Identification of Additional Factors

A transcription factor provided by the present invention can also be used to identify additional endogenous or exogenous molecules that can affect a phenotoype or trait of interest. On the one hand, such molecules include organic (small or large molecules) and/or inorganic compounds that affect expression of (i.e., regulate) a particular transcription factor. Alternatively, such molecules include endogenous molecules that are acted upon either at a transcriptional level by a transcription factor of the invention to modify a phenotype as desired. For example, the transcription factors can be employed to identify one or more downstream gene with which is subject to a regulatory effect of the transcription factor. In one approach, a transcription factor or transcription factor homologue of the invention is expressed in a host cell, e.g, a transgenic plant cell, tissue or explant, and expression products, either RNA or protein, of likely or random targets are monitored, e.g., by hybridization to a microarray of nucleic acid probes corresponding to genes expressed in a tissue or cell type of interest, by two-dimensional gel electrophoresis of protein products, or by any other method known in the art for assessing expression of gene products at the level of RNA or protein. Alternatively, a transcription factor of the invention can be used to identify promoter sequences (i.e., binding sites) involved in the regulation of a downstream target. After identifying a promoter sequence, interactions between the transcription factor and the promoter sequence can be modified by changing specific nucleotides in the promoter sequence or specific amino acids in the transcription factor that interact with the promoter sequence to alter a plant trait. Typically, transcription factor DNA-binding sites are identified by gel shift assays. After identifying the promoter regions, the promoter region sequences can be employed in double-stranded DNA arrays to identify molecules that affect the interactions of the transcription factors with their promoters (Bulyk et al. (1999) *Nature Biotechnology* 17: 573-577). A test promoter region element of a transcription factor gene may also be screened using a phage-display analysis and a phage library which comprises polynucleotides encoding any transcription factor to identify a transcription factor so encoded which binds to the test promoter region element. Such phage-display methods are well known in the art.

The identified transcription factors are also useful to identify proteins that modify the activity of the transcription factor. Such modification can occur by covalent modification, such as by phosphorylation, or by protein-protein (homo or -heteropolymer) interactions. Any method suitable for detecting protein-protein interactions can be employed. Among the methods that can be employed are co-immunoprecipitation, cross-linking and co-purification through gradients or chromatographic columns, and the two-hybrid yeast system.

The two-hybrid system detects protein interactions in vivo and is described in Chien, et al., (1991), *Proc. Natl. Acad. Sci. USA* 88, 9578-9582 and is commercially available from Clontech (Palo Alto, Calif.). In such a system, plasmids are constructed that encode two hybrid proteins: one consists of the DNA-binding domain of a transcription activator protein fused to the TF polypeptide and the other consists of the transcription activator protein's activation domain fused to an unknown protein that is encoded by a cDNA that has been recombined into the plasmid as part of a cDNA library. The DNA-binding domain fusion plasmid and the cDNA library are transformed into a strain of the yeast *Saccharomyces cerevisiae* that contains a reporter gene (e.g., lacZ) whose regulatory region contains the transcription activator's binding site. Either hybrid protein alone cannot activate transcription of the reporter gene. Interaction of the two hybrid proteins reconstitutes the functional activator protein and results in expression of the reporter gene, which is detected by an assay for the reporter gene product. Then, the library plasmids responsible for reporter gene expression are isolated and sequenced to identify the proteins encoded by the library plasmids. After identifying proteins that interact with the transcription factors, assays for compounds that interfere with the TF protein-protein interactions can be preformed.

Identification of Modulators

In addition to the intracellular molecules described above, extracellular molecules that alter activity or expression of a transcription factor, either directly or indirectly, can be identified. For example, the methods can entail first placing a candidate molecule in contact with a plant or plant cell. The molecule can be introduced by topical administration, such as spraying or soaking of a plant, and then the molecule's effect on the expression or activity of the TF polypeptide or the expression of the polynucleotide monitored. Changes in the expression of the TF polypeptide can be monitored by use of polyclonal or monoclonal antibodies, gel electrophoresis or the like. Changes in the expression of the corresponding polynucleotide sequence can be detected by use of microarrays, Northerns, quantitative PCR, or any other technique for monitoring changes in mRNA expression. These techniques are exemplified in Ausubel et al. (eds) *Current Protocols in Molecular Biology*, John Wiley & Sons (1998, and supplements through 2001). Such changes in the expression levels can be correlated with modified plant traits and thus identified molecules can be useful for soaking or spraying on fruit, vegetable and grain crops to modify traits in plants.

Essentially any available composition can be tested for modulatory activity of expression or activity of any nucleic acid or polypeptide herein. Thus, available libraries of compounds such as chemicals, polypeptides, nucleic acids and the like can be tested for modulatory activity. Often, potential modulator compounds can be dissolved in aqueous or organic (e.g., DMSO-based) solutions for easy delivery to the cell or plant of interest in which the activity of the modulator is to be tested. Optionally, the assays are designed to screen large modulator composition libraries by automating the assay steps and providing compounds from any convenient source to assays, which are typically run in parallel (e.g., in microtitre formats on microtitre plates in robotic assays).

In one embodiment, high throughput screening methods involve providing a combinatorial library containing a large number of potential compounds (potential modulator compounds). Such "combinatorial chemical libraries" are then screened in one or more assays, as described herein, to identify those library members (particular chemical species or subclasses) that display a desired characteristic activity. The compounds thus identified can serve as target compounds.

A combinatorial chemical library can be, e.g., a collection of diverse chemical compounds generated by chemical synthesis or biological synthesis. For example, a combinatorial chemical library such as a polypeptide library is formed by combining a set of chemical building blocks (e.g., in one example, amino acids) in every possible way for a given compound length (i.e., the number of amino acids in a polypeptide compound of a set length). Exemplary libraries include peptide libraries, nucleic acid libraries, antibody libraries (see, e.g., Vaughn et al. (1996) *Nature Biotechnology*, 14(3): 309-314 and PCT/US96/10287), carbohydrate libraries (see, e.g., Liang et al. *Science* (1996) 274: 1520-1522 and U.S. Pat. No. 5,593,853), peptide nucleic acid libraries (see, e.g., U.S. Pat. No. 5,539,083), and small organic molecule libraries (see, e.g., benzodiazepines, Baum *C&EN* January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337) and the like.

Preparation and screening of combinatorial or other libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37: 487-493 (1991) and Houghton et al. *Nature* 354: 84-88 (1991)). Other chemistries for generating chemical diversity libraries can also be used.

In addition, as noted, compound screening equipment for high-throughput screening is generally available, e.g., using any of a number of well known robotic systems that have also been developed for solution phase chemistries useful in assay systems. These systems include automated workstations including an automated synthesis apparatus and robotic systems utilizing robotic arms. Any of the above devices are suitable for use with the present invention, e.g., for high-throughput screening of potential modulators. The nature and implementation of modifications to these devices (if any) so that they can operate as discussed herein will be apparent to persons skilled in the relevant art.

Indeed, entire high throughput screening systems are commercially available. These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. Similarly, microfluidic implementations of screening are also commercially available.

The manufacturers of such systems provide detailed protocols the various high throughput. Thus, for example, Zymark Corp. provides technical bulletins describing screening systems for detecting the modulation of gene transcription, ligand binding, and the like. The integrated systems herein, in addition to providing for sequence alignment and, optionally, synthesis of relevant nucleic acids, can include such screening apparatus to identify modulators that have an effect on one or more polynucleotides or polypeptides according to the present invention.

In some assays it is desirable to have positive controls to ensure that the components of the assays are working properly. At least two types of positive controls are appropriate. That is, known transcriptional activators or inhibitors can be incubated with cells/plants/etc. in one sample of the assay, and the resulting increase/decrease in transcription can be detected by measuring the resulting increase in RNA/protein expression, etc., according to the methods herein. It will be appreciated that modulators can also be combined with transcriptional activators or inhibitors to find modulators which inhibit transcriptional activation or transcriptional repression. Either expression of the nucleic acids and proteins herein or any additional nucleic acids or proteins activated by the nucleic acids or proteins herein, or both, can be monitored.

In an embodiment, the invention provides a method for identifying compositions that modulate the activity or expression of a polynucleotide or polypeptide of the invention. For example, a test compound, whether a small or large molecule, is placed in contact with a cell, plant (or plant tissue or explant), or composition comprising the polynucleotide or polypeptide of interest and a resulting effect on the cell, plant, (or tissue or explant) or composition is evaluated by monitoring, either directly or indirectly, one or more of: expression level of the polynucleotide or polypeptide, activity (or modulation of the activity) of the polynucleotide or polypeptide. In some cases, an alteration in a plant phenotype can be detected following contact of a plant (or plant cell, or tissue or explant) with the putative modulator, e.g., by modulation of expression or activity of a polynucleotide or polypeptide of the invention. Modulation of expression or activity of a polynucleotide or polypeptide of the invention may also be caused by molecular elements in a signal transduction second messenger pathway and such modulation can affect similar elements in the same or another signal transduction second messenger pathway.

Subsequences

Also contemplated are uses of polynucleotides, also referred to herein as oligonucleotides, typically having at least 12 bases, preferably at least 15, more preferably at least 20, 30, or 50 bases, which hybridize under at least highly stringent (or ultra-high stringent or ultra-ultra-high stringent conditions) conditions to a polynucleotide sequence described above. The polynucleotides may be used as probes, primers, sense and antisense agents, and the like, according to methods as noted supra.

Subsequences of the polynucleotides of the invention, including polynucleotide fragments and oligonucleotides are useful as nucleic acid probes and primers. An oligonucleotide suitable for use as a probe or primer is at least about 15 nucleotides in length, more often at least about 18 nucleotides, often at least about 21 nucleotides, frequently at least about 30 nucleotides, or about 40 nucleotides, or more in length. A nucleic acid probe is useful in hybridization protocols, e.g., to identify additional polypeptide homologues of the invention, including protocols for microarray experiments. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods. See Sambrook and Ausubel, supra.

In addition, the invention includes an isolated or recombinant polypeptide including a subsequence of at least about 15 contiguous amino acids encoded by the recombinant or isolated polynucleotides of the invention. For example, such polypeptides, or domains or fragments thereof, can be used as immunogens, e.g., to produce antibodies specific for the polypeptide sequence, or as probes for detecting a sequence of interest. A subsequence can range in size from about 15 amino acids in length up to and including the full length of the polypeptide.

Production of Transgenic Plants

Modification of Traits

The polynucleotides of the invention are favorably employed to produce transgenic plants with various traits, or characteristics, that have been modified in a desirable manner, e.g., to improve the seed characteristics of a plant. For example, alteration of expression levels or patterns (e.g., spatial or temporal expression patterns) of one or more of the transcription factors (or transcription factor homologues) of the invention, as compared with the levels of the same protein found in a wild type plant, can be used to modify a plant's traits. An illustrative example of trait modification, improved characteristics, by altering expression levels of a particular transcription factor is described further in the Examples and the Sequence Listing.

Antisense and Cosuppression Approaches

In addition to expression of the nucleic acids of the invention as gene replacement or plant phenotype modification nucleic acids, the nucleic acids are also useful for sense and anti-sense suppression of expression, e.g., to down-regulate expression of a nucleic acid of the invention, e.g., as a further mechanism for modulating plant phenotype. That is, the nucleic acids of the invention, or subsequences or anti-sense sequences thereof, can be used to block expression of naturally occurring homologous nucleic acids. A variety of sense and anti-sense technologies are known in the art, e.g., as set forth in Lichtenstein and Nellen (1997) *Antisense Technology: A Practical Approach* IRL Press at Oxford University, Oxford, England. In general, sense or anti-sense sequences are introduced into a cell, where they are optionally amplified, e.g., by transcription. Such sequences include both simple oligonucleotide sequences and catalytic sequences such as ribozymes.

For example, a reduction or elimination of expression (i.e., a "knock-out") of a transcription factor or transcription factor homologue polypeptide in a transgenic plant, e.g., to modify a plant trait, can be obtained by introducing an antisense construct corresponding to the polypeptide of interest as a cDNA. For antisense suppression, the transcription factor or homologue cDNA is arranged in reverse orientation (with respect to the coding sequence) relative to the promoter sequence in the expression vector. The introduced sequence need not be the full length cDNA or gene, and need not be identical to the cDNA or gene found in the plant type to be transformed. Typically, the antisense sequence need only be capable of hybridizing to the target gene or RNA of interest. Thus, where the introduced sequence is of shorter length, a higher degree of homology to the endogenous transcription factor sequence will be needed for effective antisense suppression. While antisense sequences of various lengths can be utilized, preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous transcription factor gene in the plant cell.

Suppression of endogenous transcription factor gene expression can also be achieved using a ribozyme. Ribozymes are RNA molecules that possess highly specific endoribonuclease activity. The production and use of ribozymes are disclosed in U.S. Pat. No. 4,987,071 and U.S. Pat. No. 5,543,508. Synthetic ribozyme sequences including antisense RNAs can be used to confer RNA cleaving activity on the antisense RNA, such that endogenous mRNA molecules that hybridize to the antisense RNA are cleaved, which in turn leads to an enhanced antisense inhibition of endogenous gene expression.

Vectors in which RNA encoded by a transcription factor or transcription factor homologue cDNA is over-expressed can also be used to obtain co-suppression of a corresponding endogenous gene, e.g., in the manner described in U.S. Pat. No. 5,231,020 to Jorgensen. Such co-suppression (also termed sense suppression) does not require that the entire transcription factor cDNA be introduced into the plant cells, nor does it require that the introduced sequence be exactly identical to the endogenous transcription factor gene of interest. However, as with antisense suppression, the suppressive efficiency will be enhanced as specificity of hybridization is increased, e.g., as the introduced sequence is lengthened, and/or as the sequence similarity between the introduced sequence and the endogenous transcription factor gene is increased.

Vectors expressing an untranslatable form of the transcription factor mRNA, e.g., sequences comprising one or more stop codon, or nonsense mutation) can also be used to suppress expression of an endogenous transcription factor, thereby reducing or eliminating it's activity and modifying one or more traits. Methods for producing such constructs are described in U.S. Pat. No. 5,583,021. Preferably, such constructs are made by introducing a premature stop codon into the transcription factor gene. Alternatively, a plant trait can be modified by gene silencing using double-strand RNA (Sharp (1999) *Genes and Development* 13: 139-141).

Another method for abolishing the expression of a gene is by insertion mutagenesis using the T-DNA of *Agrobacterium tumefaciens*. After generating the insertion mutants, the mutants can be screened to identify those containing the insertion in a transcription factor or transcription factor homologue gene. Plants containing a single transgene insertion event at the desired gene can be crossed to generate homozygous plants for the mutation (Koncz et al. (1992) *Methods in Arabidopsis Research*. World Scientific).

Alternatively, a plant phenotype can be altered by eliminating an endogenous gene, such as a transcription factor or transcription factor homologue, e.g., by homologous recombination (Kempin et al. (1997) *Nature* 389: 802).

A plant trait can also be modified by using the Cre-lox system (for example, as described in U.S. Pat. No. 5,658,772). A plant genome can be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

The polynucleotides and polypeptides of this invention can also be expressed in a plant in the absence of an expression cassette by manipulating the activity or expression level of the endogenous gene by other means. For example, by ectopically expressing a gene by T-DNA activation tagging (Ichikawa et al. (1997) *Nature* 390 698-701; Kakimoto et al. (1996) *Science* 274: 982-985). This method entails transforming a plant with a gene tag containing multiple transcriptional enhancers and once the tag has inserted into the genome, expression of a flanking gene coding sequence becomes deregulated. In another example, the transcriptional machinery in a plant can be modified so as to increase transcription levels of a polynucleotide of the invention (See, e.g., PCT Publications WO 96/06166 and WO 98/53057 which describe the modification of the DNA-binding specificity of zinc finger proteins by changing particular amino acids in the DNA-binding motif).

The transgenic plant can also include the machinery necessary for expressing or altering the activity of a polypeptide encoded by an endogenous gene, for example by altering the phosphorylation state of the polypeptide to maintain it in an activated state.

Transgenic plants (or plant cells, or plant explants, or plant tissues) incorporating the polynucleotides of the invention and/or expressing the polypeptides of the invention can be produced by a variety of well established techniques as described above. Following construction of a vector, most typically an expression cassette, including a polynucleotide, e.g., encoding a transcription factor or transcription factor homologue, of the invention, standard techniques can be used to introduce the polynucleotide into a plant, a plant cell, a plant explant or a plant tissue of interest. Optionally, the plant cell, explant or tissue can be regenerated to produce a transgenic plant.

The plant can be any higher plant, including gymnosperms, monocotyledonous and dicotyledenous plants. Suitable protocols are available for Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops. See protocols described in Ammirato et al. (1984) *Handbook of Plant Cell Culture—Crop Species*, Macmillan Publ. Co. Shimamoto et al. (1989) *Nature* 338: 274-276; Fromm et al. (1990) *Bio/Technology* 8: 833-839; and Vasil et al. (1990) *Bio/Technology* 8: 429-434.

Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* mediated transformation. Transformation means introducing a nucleotide sequence into a plant in a manner to cause stable or transient expression of the sequence.

Successful examples of the modification of plant characteristics by transformation with cloned sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants are preferably selected using a dominant selectable marker incorporated into the transformation vector. Typically, such a marker will confer antibiotic or herbicide resistance on the transformed plants, and selection of transformants can be accomplished by exposing the plants to appropriate concentrations of the antibiotic or herbicide.

After transformed plants are selected and grown to maturity, those plants showing a modified trait are identified. The modified trait can be any of those traits described above. Additionally, to confirm that the modified trait is due to changes in expression levels or activity of the polypeptide or polynucleotide of the invention can be determined by analyzing mRNA expression using Northern blots, RT-PCR or microarrays, or protein expression using immunoblots or Western blots or gel shift assays.

Integrated Systems—Sequence Identity

Additionally, the present invention may be an integrated system, computer or computer readable medium that comprises an instruction set for determining the identity of one or more sequences in a database. In addition, the instruction set can be used to generate or identify sequences that meet any specified criteria. Furthermore, the instruction set may be used to associate or link certain functional benefits, such improved characteristics, with one or more identified sequence.

For example, the instruction set can include, e.g., a sequence comparison or other alignment program, e.g., an available program such as, for example, the Wisconsin Package Version 10.0, such as BLAST, FASTA, PILEUP, FIND-PATTERNS or the like (GCG, Madison, Wis.). Public sequence databases such as GenBank, EMBL, Swiss-Prot and PIR or private sequence databases such as PhytoSeq (Incyte Pharmaceuticals, Palo Alto, Calif.) can be searched.

Alignment of sequences for comparison can be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. U.S.A.* 85: 2444, by computerized implementations of these algorithms. After alignment, sequence comparisons between two (or more) polynucleotides or polypeptides are typically performed by comparing sequences of the two sequences over a comparison window to identify and compare local regions of sequence similarity. The comparison window can be a segment of at least about 20 contiguous positions, usually about 50 to about 200, more usually about 100 to about 150 contiguous positions. A description of the method is provided in Ausubel et al., supra.

A variety of methods for determining sequence relationships can be used, including manual alignment and computer assisted sequence alignment and analysis. This later approach is a preferred approach in the present invention, due to the increased throughput afforded by computer assisted methods. As noted above, a variety of computer programs for performing sequence alignment are available, or can be produced by one of skill.

One example algorithm that is suitable for determining percent sequence identity and sequence similarity is the BLAST algorithm, which is described in Altschul et al. *J. Mol. Biol.* 215: 403-410 (1990). Software for performing BLAST analyses is publicly available, e.g., through the National Center for Biotechnology Information (www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89: 10915). Unless otherwise indicated, "sequence identity" here refers to the % sequence identity generated from a tblastx using the NCBI version of the algorithm at the default settings using gapped alignments with the filter "off" (www.ncbi.nlm.nih.gov/). Additionally, BLASTX and TBLASTX programs may be used.

In addition to calculating percent sequence identity, the BLAST algorithm also performs a statistical analysis of the similarity between two sequences (see, e.g., Karlin & Altschul (1993) *Proc. Natl. Acad. Sci. USA* 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, in this context, homologous) if the smallest sum probability in a comparison of the test nucleic acid to the reference nucleic acid is less than about 0.1, or less than about 0.01, and or even less than about 0.001. An additional example of a useful sequence alignment algorithm is PILEUP. PILEUP creates a multiple sequence alignment from a group of related sequences using progressive, pairwise alignments. The program can align, e.g., up to 300 sequences of a maximum length of 5,000 letters.

The integrated system, or computer typically includes a user input interface allowing a user to selectively view one or more sequence records corresponding to the one or more character strings, as well as an instruction set which aligns the one or more character strings with each other or with an additional character string to identify one or more region of sequence similarity. The system may include a link of one or more character strings with a particular phenotype or gene function. Typically, the system includes a user readable output element which displays an alignment produced by the alignment instruction set.

The methods of this invention can be implemented in a localized or distributed computing environment. In a distributed environment, the methods may implemented on a single computer comprising multiple processors or on a multiplicity of computers. The computers can be linked, e.g. through a common bus, but more preferably the computer(s) are nodes on a network. The network can be a generalized or a dedicated local or wide-area network and, in certain preferred embodiments, the computers may be components of an intra-net or an internet.

Thus, the invention provides methods for identifying a sequence similar or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an inter or intra net) and a query is made against the sequence database using the relevant sequences herein and associated plant phenotypes or gene functions.

Any sequence herein can be entered into the database, before or after querying the database. This provides for both expansion of the database and, if done before the querying step, for insertion of control sequences into the database. The control sequences can be detected by the query to ensure the general integrity of both the database and the query. As noted, the query can be performed using a web browser based interface. For example, the database can be a centralized public database such as those noted herein, and the querying can be done from a remote terminal or computer across an internet or intranet.

EXAMPLES

The following examples are intended to illustrate but not limit the present invention.

Example I

Full Length Gene Identification and Cloning

Putative transcription factor sequences (genomic or ESTs) related to known transcription factors were identified in the *Arabidopsis thaliana* GenBank database using the tblastn sequence analysis program using default parameters and a P-value cutoff threshold of −4 or −5 or lower, depending on the length of the query sequence. Putative transcription factor sequence hits were then screened to identify those containing particular sequence strings. If the sequence hits contained such sequence strings, the sequences were confirmed as transcription factors.

Alternatively, *Arabidopsis thaliana* cDNA libraries derived from different tissues or treatments, or genomic libraries were screened to identify novel members of a transcription family using a low stringency hybridization approach. Probes were synthesized using gene specific primers in a standard PCR reaction (annealing temperature 60° C.) and labeled with $^{32}$P dCTP using the High Prime DNA Labeling Kit (Boehringer Mannheim). Purified radiolabelled probes were added to filters immersed in Church hybridization medium (0.5 M NaPO$_4$ pH 7.0, 7% SDS, 1% w/v bovine serum albumin) and hybridized overnight at 60° C. with shaking. Filters were washed two times for 45 to 60 minutes with 1×SSC, 1% SDS at 60° C.

To identify additional sequence 5' or 3' of a partial cDNA sequence in a cDNA library, 5' and 3' rapid amplification of cDNA ends (RACE) was performed using the Marathon™ cDNA amplification kit (Clontech, Palo Alto, Calif.). Generally, the method entailed first isolating poly(A) mRNA, performing first and second strand cDNA synthesis to generate double stranded cDNA, blunting cDNA ends, followed by ligation of the Marathon™ Adaptor to the cDNA to form a library of adaptor-ligated ds cDNA.

Gene-specific primers were designed to be used along with adaptor specific primers for both 5' and 3' RACE reactions. Nested primers, rather than single primers, were used to increase PCR specificity. Using 5' and 3' RACE reactions, 5' and 3' RACE fragments were obtained, sequenced and cloned. The process can be repeated until 5' and 3' ends of the full-length gene were identified. Then the full-length cDNA was generated by PCR using primers specific to 5' and 3' ends of the gene by end-to-end PCR.

Example II

Construction of Expression Vectors

The sequence was amplified from a genomic or cDNA library using primers specific to sequences upstream and downstream of the coding region. The expression vector was pMEN20 or pMEN65, which are both derived from pMON316 (Sanders et al, (1987) *Nucleic Acids Research* 15: 1543-58) and contain the CaMV 35S promoter to express transgenes. To clone the sequence into the vector, both pMEN20 and the amplified DNA fragment were digested separately with SalI and NotI restriction enzymes at 37° C. for 2 hours. The digestion products were subject to electrophoresis in a 0.8% agarose gel and visualized by ethidium bromide staining. The DNA fragments containing the sequence and the linearized plasmid were excised and purified by using a Qiaquick gel extraction kit (Qiagen, CA). The fragments of interest were ligated at a ratio of 3:1 (vector to insert). Ligation reactions using T4 DNA ligase (New England Biolabs, MA) were carried out at 16° C. for 16 hours. The ligated DNAs were transformed into competent cells of the *E. coli* strain DH5alpha by using the heat shock method. The transformations were plated on LB plates containing 50 mg/l kanamycin (Sigma, MO).

Individual colonies were grown overnight in five milliliters of LB broth containing 50 mg/l kanamycin at 37° C. Plasmid DNA was purified by using Qiaquick Mini Prep kits (Qiagen, CA).

Example III

Transformation of *Agrobacterium* with the Expression Vector

After the plasmid vector containing the gene was constructed, the vector was used to transform *Agrobacterium tumefaciens* cells expressing the gene products. The stock of *Agrobacterium tumefaciens* cells for transformation were made as described by Nagel et al. (1990) *FEMS Microbiol Letts.* 67: 325-328. *Agrobacterium* strain ABI was grown in 250 ml LB medium (Sigma) overnight at 28° C. with shaking until an absorbance ($A_{600}$) of 0.5-1.0 was reached. Cells were harvested by centrifugation at 4,000×g for 15 min at 4° C. Cells were then resuspended in 250 µl chilled buffer (1 mM HEPES, pH adjusted to 7.0 with KOH). Cells were centrifuged again as described above and resuspended in 125 µl chilled buffer. Cells were then centrifuged and resuspended two more times in the same HEPES buffer as described above at a volume of 100 µl and 750 µl, respectively. Resuspended cells were then distributed into 40 µl aliquots, quickly frozen in liquid nitrogen, and stored at −80° C.

*Agrobacterium* cells were transformed with plasmids prepared as described above following the protocol described by Nagel et al. For each DNA construct to be transformed, 50-100 ng DNA (generally resuspended in 10 mM Tris-HCl, 1 mM EDTA, pH 8.0) was mixed with 40 µl of *Agrobacterium* cells. The DNA/cell mixture was then transferred to a chilled cuvette with a 2 mm electrode gap and subject to a 2.5 kV charge dissipated at 25 µF and 200 µF using a Gene Pulser II apparatus (Bio-Rad). After electroporation, cells were immediately resuspended in 1.0 ml LB and allowed to recover without antibiotic selection for 2-4 hours at 28° C. in a shaking incubator. After recovery, cells were plated onto selective medium of LB broth containing 100 µg/ml spectinomycin (Sigma) and incubated for 24-48 hours at 28° C. Single colonies were then picked and inoculated in fresh medium. The presence of the plasmid construct was verified by PCR amplification and sequence analysis.

Example IV

Transformation of *Arabidopsis* Plants with *Agrobacterium tumefaciens* with Expression Vector After transformation of *Agrobacterium tumefaciens* with plasmid vectors containing the gene, single *Agrobacterium* colonies were identified, propagated, and used to transform *Arabidopsis* plants. Briefly, 500 ml cultures of LB medium containing 50 mg/l kanamycin were inoculated with the colonies and grown at 28° C with shaking for 2 days until an absorbance ($A_{600}$) of >2.0 is reached. Cells were then harvested by centrifugation at 4,000×g for 10 min, and resuspended in infiltration medium (½× Murashige and Skoog salts (Sigma), 1× Gamborg's B-5 vitamins (Sigma), 5.0% (w/v) sucrose (Sigma), 0.044 µM benzylamino purine (Sigma), 200 µl/l Silwet L-77 (Lehle Seeds) until an absorbance ($A_{600}$) of 0.8 was reached.

Prior to transformation, *Arabidopsis thaliana* seeds (ecotype Columbia) were sown at a density of ~10 plants per 4" pot onto Pro-Mix BX potting medium (Hummert International) covered with fiberglass mesh (18 mm×16 mm). Plants were grown under continuous illumination (50-75 µE/m²/sec) at 22-23° C. with 65-70% relative humidity. After about 4 weeks, primary inflorescence stems (bolts) are cut off to encourage growth of multiple secondary bolts. After flowering of the mature secondary bolts, plants were prepared for transformation by removal of all siliques and opened flowers.

The pots were then immersed upside down in the mixture of *Agrobacterium* infiltration medium as described above for 30 sec, and placed on their sides to allow draining into a 1'×2' flat surface covered with plastic wrap. After 24 h, the plastic wrap was removed and pots are turned upright. The immersion procedure was repeated one week later, for a total of two immersions per pot. Seeds were then collected from each transformation pot and analyzed following the protocol described below.

Example V

Identification of *Arabidopsis* Primary Transformants

Seeds collected from the transformation pots were sterilized essentially as follows. Seeds were dispersed into in a solution containing 0.1% (v/v) Triton X-100 (Sigma) and sterile $H_2O$ and washed by shaking the suspension for 20 min. The wash solution was then drained and replaced with fresh wash solution to wash the seeds for 20 min with shaking. After removal of the second wash solution, a solution containing 0.1% (v/v) Triton X-100 and 70% ethanol (Equistar) was added to the seeds and the suspension was shaken for 5 min. After removal of the ethanol/detergent solution, a solution containing 0.1% (v/v) Triton X-100 and 30% (v/v) bleach (Clorox) was added to the seeds, and the suspension was shaken for 10 min. After removal of the bleach/detergent solution, seeds were then washed five times in sterile distilled $H_2O$. The seeds were stored in the last wash water at 4° C. for 2 days in the dark before being plated onto antibiotic selection medium (1× Murashige and Skoog salts (pH adjusted to 5.7 with 1M KOH), 1× Gamborg's B-5 vitamins, 0.9% phytagar (Life Technologies), and 50 mg/l kanamycin). Seeds were germinated under continuous illumination (50-75 µE/m²/sec) at 22-23° C. After 7-10 days of growth under these conditions, kanamycin resistant primary transformants ($T_1$ generation) were visible and obtained. These seedlings were transferred first to fresh selection plates where the seedlings continued to grow for 3-5 more days, and then to soil (Pro-Mix BX potting medium).

Primary transformants were crossed and progeny seeds ($T_2$) collected; kanamycin resistant seedlings were selected and analyzed. The expression levels of the recombinant polynucleotides in the transformants varies from about a 5% expression level increase to a least a 100% expression level increase. Similar observations are made with respect to polypeptide level expression.

Example VI

Identification of *Arabidopsis* Plants with Transcription Factor Gene Knockouts The screening of insertion mutagenized *Arabidopsis* collections for null mutants in a known target gene was essentially as described in Krysan et al (1999) *Plant Cell* 11: 2283-2290. Briefly, gene-specific primers, nested by 5-250 base pairs to each other, were designed from the 5' and 3' regions of a known target gene. Similarly, nested sets of primers were also created specific to each of the T-DNA or transposon ends (the "right" and "left" borders). All possible combinations of gene specific and T-DNA/transposon primers were used to detect by PCR an insertion event within or close to the target gene. The amplified DNA fragments were then sequenced which allows the precise determination of the T-DNA/transposon insertion point relative to the target gene. Insertion events within the coding or intervening sequence of the genes were deconvoluted from a pool comprising a plurality of insertion events to a single unique mutant plant for functional characterization. The method is described in more detail in Yu and Adam, U.S. application Ser. No. 09/177,733 filed Oct. 23, 1998.

Example VII

Identification of Modified Phenotypes in Overexpression or Gene Knockout Plants Experiments were performed to identify those transformants or knockouts that exhibited modified biochemical characteristics. Among the biochemicals that were assayed were insoluble sugars, such as arabinose, fucose, galactose, mannose, rhamnose or xylose or the like; prenyl lipids, such as lutein, beta-carotene, xanthophyll-1, xanthophyll-2, chlorophylls A or B, or alpha-, delta- or gamma-tocopherol or the like; fatty acids, such as 16:0 (palmitic acid), 16:1 (palmitoleic acid), 18:0 (stearic acid), 18:1 (oleic acid), 18:2 (linoleic acid), 20:0, 18:3 (linolenic acid), 20:1 (eicosenoic acid), 20:2, 22:1 (erucic acid) or the like; waxes, such as by altering the levels of C29, C31, or C33 alkanes; sterols, such as brassicasterol, campesterol, stigmasterol, sitosterol or stigmastanol or the like, glucosinolates, protein or oil levels.

Fatty acids were measured using two methods depending on whether the tissue was from leaves or seeds. For leaves, lipids were extracted and esterified with hot methanolic H2SO4 and partitioned into hexane from methanolic brine. For seed fatty acids, seeds were pulverized and extracted in methanol:heptane:toluene:2,2-dimethoxypropane:H2SO4 (39:34:20:5:2) for 90 minutes at 80° C. After cooling to room temperature the upper phase, containing the seed fatty acid esters, was subjected to GC analysis. Fatty acid esters from both seed and leaf tissues were analyzed with a Supelco SP-2330 column.

Glucosinolates were purified from seeds or leaves by first heating the tissue at 95° C. for 10 minutes. Preheated ethanol:water (50:50) is and after heating at 95° C. for a further 10 minutes, the extraction solvent is applied to a DEAE Sephadex column which had been previously equilibrated with 0.5 M pyridine acetate. Desulfoglucosinolates were eluted with 300 ul water and analyzed by reverse phase HPLC monitoring at 226 nm.

For wax alkanes, samples were extracted using an identical method as fatty acids and extracts were analyzed on a HP 5890 GC coupled with a 5973 MSD. Samples were chromatographed on a J&W DB35 mass spectrometer (J&W Scientific).

To measure prenyl lipids levels, seeds or leaves were pulverized with 1 to 2% pyrogallol as an antioxidant. For seeds, extracted samples were filtered and a portion removed for tocopherol and carotenoid/chlorophyll analysis by HPLC. The remaining material was saponified for sterol determination. For leaves, an aliquot was removed and diluted with methanol and chlorophyll A, chlorophyll B, and total carotenoids measured by spectrophotometry by determining absorbance at 665.2 nm, 652.5 nm, and 470 nm. An aliquot was removed for tocopherol and carotenoid/chlorophyll composition by HPLC using a Waters uBondapak C18 column (4.6 mm×150 mm). The remaining methanolic solution was saponified with 10% KOH at 80° C. for one hour. The samples were cooled and diluted with a mixture of methanol and water. A solution of 2% methylene chloride in hexane was mixed in and the samples were centrifuged. The aqueous methanol phase was again re-extracted 2% methylene chloride in hexane and, after centrifugation, the two upper phases were combined and evaporated. 2% methylene chloride in hexane was added to the tubes and the samples were then extracted with one ml of water. The upper phase was removed, dried, and resuspended in 400 ul of 2% methylene chloride in hexane and analyzed by gas chromatography using a 50 m DB-5 ms (0.25 mm ID, 0.25 um phase, J&W Scientific).

Insoluble sugar levels were measured by the method essentially described by Reiter et al., *Plant Journal* 12: 335-345. This method analyzes the neutral sugar composition of cell wall polymers found in *Arabidopsis* leaves. Soluble sugars were separated from sugar polymers by extracting leaves with hot 70% ethanol. The remaining residue containing the insoluble polysaccharides was then acid hydrolyzed with allose added as an internal standard. Sugar monomers generated by the hydrolysis were then reduced to the corresponding alditols by treatment with NaBH4, then were acetylated to generate the volatile alditol acetates which were then analyzed by GC-FID. Identity of the peaks was determined by comparing the retention times of known sugars converted to the corresponding alditol acetates with the retention times of peaks from wild-type plant extracts. Alditol acetates were analyzed on a Supelco SP-2330 capillary column (30 m×250 um×0.2 um) using a temperature program beginning at 180° C. for 2 minutes followed by an increase to 220° C. in 4 minutes. After holding at 220° C. for 10 minutes, the oven temperature is increased to 240° C. in 2 minutes and held at this temperature for 10 minutes and brought back to room temperature.

To identify plants with alterations in total seed oil or protein content, 150 mg of seeds from T2 progeny plants were subjected to analysis by Near Infrared Reflectance (NIR) using a Foss NirSystems Model 6500 with a spinning cup transport system.

Experiments were performed to identify those transformants or knockouts that exhibited an improved pathogen tolerance. For such studies, the transformants were exposed to biotropic fungal pathogens, such as *Erisyphe orontii*, and necrotropic fungal pathogens, such as *Fusarium oxysporum*. *Fusarium oxysporum* isolates cause vascular wilts and damping off of various annual vegetables, perennials and weeds (Mauch-Mani and Slusarenko (1994) *Molecular Plant-Microbe Interactions* 7: 378-383). For *Fusarium oxysporum* experiments, plants grown on petri dishes were sprayed with a fresh spore suspension of *F. oxysporum*. The spore suspension was prepared as follows: A plug of fungal hyphae from a plate culture was placed on a fresh potato dextrose agar plate and allowed to spread for one week. 5 ml sterile water was then added to the plate, swirled, and pipetted into 50 ml Armstrong *Fusarium* medium. Spores were grown overnight in *Fusarium* medium and then sprayed onto plants using a Preval paint sprayer. Plant tissue was harvested and frozen in liquid nitrogen 48 hours post infection.

*Erysiphe orontii* is a causal agent of powdery mildew. For *Erysiphe orontii* experiments, plants were grown approximately 4 weeks in a greenhouse under 12 hour light (20 C, ~30% relative humidity (rh)). Individual leaves were infected with *E. orontii* spores from infected plants using a camel's hair brush, and the plants were transferred to a Percival growth chamber (20 C, 80% rh.). Plant tissue was harvested and frozen in liquid nitrogen 7 days post infection.

*Botrytis cinerea* is a necrotrophic pathogen. *Botrytis cinerea* was grown on potato dextrose agar in the light. A spore culture was made by spreading 10 ml of sterile water on the fungus plate, swirling and transferring spores to 10 ml of sterile water. The spore inoculum (approx. 105 spores/ml) was used to spray 10 day-old seedlings grown under sterile conditions on MS (minus sucrose) media. Symptoms were evaluated every day up to approximately 1 week.

Infection with bacterial pathogens *Pseudomonas syringae* pv *maculicola* strain 4326 and pv *maculicola* strain 4326 was performed by hand inoculation at two doses. Two inoculation doses allows the differentiation between plants with enhanced susceptibility and plants with enhanced resistance to the pathogen. Plants were grown for 3 weeks in the greenhouse, then transferred to the growth chamber for the remainder of their growth. Psm ES4326 was hand inoculated with 1 ml syringe on 3 fully-expanded leaves per plant (4½ wk old), using at least 9 plants per overexpressing line at two inoculation doses, OD=0.005 and OD=0.0005. Disease scoring occured at day 3 post-inoculation with pictures of the plants and leaves taken in parallel.

In some instances, expression patterns of the pathogen-induced genes (such as defense genes) was monitored by microarray experiments. cDNAs were generated by PCR and resuspended at a final concentration of ~100 ng/ul in 3×SSC or 150 mM Na-phosphate (Eisen and Brown (1999) *Meth. in Enzymol.* 303: 179-205). The cDNAs were spotted on microscope glass slides coated with polylysine. The prepared cDNAs were aliquoted into 384 well plates and spotted on the slides using an x-y-z gantry (OmniGrid) purchased from GeneMachines (Menlo Park, Calif.) outfitted with quill type pins purchased from Telechem International (Sunnyvale, Calif.). After spotting, the arrays were cured for a minimum of one week at room temperature, rehydrated and blocked following the protocol recommended by Eisen and Brown (1999).

Sample total RNA (10 ug) samples were labeled using fluorescent Cy3 and Cy5 dyes. Labeled samples were resuspended in 4×SSC/0.03% SDS/4 ug salmon sperm DNA/2 ug tRNA/50 mM Na-pyrophosphate, heated for 95° C. for 2.5 minutes, spun down and placed on the array. The array was then covered with a glass coverslip and placed in a sealed chamber. The chamber was then kept in a water bath at 62° C. overnight. The arrays were washed as described in Eisen and Brown (1999) and scanned on a General Scanning 3000 laser scanner. The resulting files are subsequently quantified using Imagene a software purchased from BioDiscovery (Los Angeles, Calif.).

Experiments were performed to identify those transformants or knockouts that exhibited an improved environmental stress tolerance. For such studies, the transformants were exposed to a variety of environmental stresses. Plants were exposed to chilling stress (6 hour exposure to 4-8° C.), heat stress (6 hour exposure to 32-37° C.), high salt stress (6 hour exposure to 200 mM NaCl), drought stress (168 hours after removing water from trays), osmotic stress (6 hour exposure to 3 M mannitol), or nutrient limitation (nitrogen, phosphate, and potassium) (Nitrogen: all components of MS medium remained constant except N was reduced to 20 mg/l of NH4NO$_3$, or Phosphate: All components of MS medium except KH2PO4, which was replaced by K2SO4, Potassium: All components of MS medium except removal of KNO3 and KH2PO4, which were replaced by NaH4PO4).

Experiments were performed to identify those transformants or knockouts that exhibited a modified structure and development characteristics. For such studies, the transformants were observed by eye to identify novel structural or developmental characteristics associated with the ectopic expression of the polynucleotides or polypeptides of the invention.

Experiments were performed to identify those transformants or knockouts that exhibited modified sugar-sensing. For such studies, seeds from transformants were germinated on media containing 5% glucose or 9.4% sucrose which normally partially restrict hypocotyl elongation. Plants with altered sugar sensing may have either longer or shorter hypocotyls than normal plants when grown on this media. Additionally, other plant traits may be varied such as root mass.

Flowering time was measured by the number of rosette leaves present when a visible inflorescence of approximately 3 cm is apparent Rosette and total leaf number on the progeny stem are tightly correlated with the timing of flowering (Koornneef et al (1991) *Mol. Gen. Genet* 229: 57-66. The vernalization response was measured. For vernalization treatments, seeds were sown to MS agar plates, sealed with micropore tape, and placed in a 4° C. cold room with low light levels for 6-8 weeks. The plates were then transferred to the growth rooms alongside plates containing freshly sown non-vernalized controls. Rosette leaves were counted when a visible inflorescence of approximately 3 cm was apparent.

Modified phenotypes observed for particular overexpressor or knockout plants are provided in Table 4 and Table 5. For a particular overexpressor that shows a less beneficial characteristic, it may be more useful to select a plant with a decreased expression of the particular transcription factor. For a particular knockout that shows a less beneficial characteristic, it may be more useful to select a plant with an increased expression of the particular transcription factor.

The sequences of the Sequence Listing or those discloses here can be used to prepare transgenic plants and plants with altered traits. The specific transgenic plants listed below are produced from the sequences of the Sequence Listing, as noted. Table 4 and Table 5 provide exemplary polynucleotide and polypeptide sequences of the invention. Table 4 includes, from left to right for each sequence: the first column shows the polynucleotide SEQ ID NO; the second column shows the polypeptide SEQ ID NO encoded by the polynucleotide; the third column shows the Mendel Gene ID No., GID; the fourth column, CDS, shows the start and stop nucleotide positions of the encoded polypeptide, respectively, with respect to the polynucleotide co-ordinates; the fifth column shows the amino acid residue positions of the conserved domain in amino acid (AA) co-ordinates; and the sixth column shows if the polynucleotide was knocked out (KO) or overexpressed (OE) in a transgenic plant. Table 5 includes, from left to right for each sequence: the first column shows the nucleotide SEQ ID NO.; the second column shows the polypeptide SEQ ID NO encoded by the polynucleotide; the third column shows the Mendel Gene ID No., GID; the fourth column shows if the polynucleotide was knocked out (KO) or overexpressed (OE) in a transgenic plant; and the fifth column shows the trait resulting from the knock out or overexpression of the polynucleotide in the transgenic plant.

TABLE 4

| SEQ ID NO (polynucleotide) | SEQ ID NO (polypeptide) | GID | CDS | Conserved domain in AA coordinates | Knockout or overexpressor |
|---|---|---|---|---|---|
| 1 | 2 | G481 | 103 . . . 528 | 20-109 | OE |
| 3 | 4 | G1466 | 16 . . . 1278 | 154-420 | OE |

TABLE 5

| SEQ ID NO (polynucleotide) | SEQ ID NO (polypeptide) | GID | Observed phenotype or trait | Overexpressor or knockout |
|---|---|---|---|---|
| 1 | 2 | G481 | Germination assay: High sucrose, osmotic stress | OE |
| 3 | 4 | G1466 | Seed composition assay: High seed oil and protein content | OE |

G481: Better Germination on High Sucrose.

Seed of plants overexpressing sequence G481 (SEQ ID NOs:1 and 2) showed slightly better germination when grown on high sucrose medium (5% glucose or 9.4% sucrose). The plants showed longer radicle and more cotyledon expansion. In one line (line 8) analysis of leaf insoluble sugars showed a slight increase in decrease in Rhamnose levels (16.9% vs. approximately 11.4% in wild-type plants) and a decrease in Arabinose and Xylose levels (15.3% and 12.8% vs. approximately 19.0% and 21% in wild-type plants, respectively).

In wild-type plants, G481 was predominantly expressed in flower and silique, and to a lesser extent, in rosette, embryo, and germinating seed.

The potential utility of G481 includes a possible role in sugar sensing, a plant mechanism that has been shown to be involved in the following: 1) altering storage compound accumulation (oil and/or protein) in seeds which could impact yield and seed quality, and 2) altering photosynthetic rate which could also impact yield in vegetative tissues as well as seed. Sugars are key regulatory molecules that affect diverse processes in higher plants including germination, growth, flowering, senescence, sugar metabolism and photosynthesis. Sucrose is the major transport form of photosynthate and its flux through cells has been shown to affect gene expression and alter storage compound accumulation in seeds (source-sink relationships).

The enhanced germination phenotype of transgenic plants overexpressing G481 under a condition of osmotic stress (such as high concentrations of sucrose) suggests the gene could also be used to improve plant tolerance to water deficit related conditions such as drought stress, salt stress, and freezing stress. Thus G481 could be used to engineer plants with enhanced stress tolerance that could ultimately impact survivability and yield.

G1466: Increased Seed Oil; Decreased Protein Content.

Seed of plants overexpressing sequences G1466 (SEQ ID NOs:3 and 4) was subjected to NIR analysis and an increase in seed oil content compared with seed from wild-type plants was identified (39% vs. approximately 35% in wild-type plants). In addition, a slight decrease in seed protein content compared with seed from wild-type plants was identified (20.8% vs. approximately 23% in wild-type plants).

In wild-type plants, G1466 was expressed in all tissues examined.

Therefore, G1466 could be used to modify high value seed quality traits such protein, oil and carbohydrates content and composition in any plant in which the expression of this gene is altered. Altering the amount of seed oil, protein or carbohydrate could effectively increase the yield and quality. Altering the composition of seeds would improve feed quality by altering availability of energy and phosphorus, and to improve the amino acid balance of grain meal or to improve oil quality for human food and industrial uses. Altering seed composition with G1466 could also improved grain quality for the wet milling industry as well as provide a means for the production of novel polymers and chemicals.

Example VIII

Identification of Homologous Sequences

Homologous sequences from *Arabidopsis* and plant species other than *Arabidopsis* were identified using database sequence search tools, such as the Basic Local Alignment Search Tool (BLAST) (Altschul et al. (1990) *J. Mol. Biol.* 215: 403-410; and Altschul et al. (1997) *Nucl. Acid Res.* 25: 3389-3402). The tblastx sequence analysis programs were employed using the BLOSUM-62 scoring matrix (Henikoff, S. and Henikoff, J. G. (1992) *Proc. Natl. Acad. Sci.* 89: 10915-10919).

Identified orthologs and homologs of *Arabidopsis* sequences are provided in Tables 6 and 7. The percent sequence identity among these sequences can be as low as 47%, or even lower sequence identity. Additionally, the entire NCBI GenBank database was filtered for sequences from all plants except *Arabidopsis thaliana* by selecting all entries in the NCBI GenBank database associated with NCBI taxonomic ID 33090 (Viridiplantae; all plants) and excluding entries associated with taxonomic ID 3701 (*Arabidopsis thaliana*). These sequences are compared to sequences representing genes of SEQ IDs NOs:2 and 4 using the Washington University TBLASTX algorithm (version 2.0a19MP) at the default settings using gapped alignments with the filter "off". For each gene of SEQ IDs NOs:2 and 4 individual comparisons were ordered by probability score (P-value), where the score reflects the probability that a particular alignment occurred by chance. For example, a score of 3.6e-40 is $3.6 \times 10^{40}$. In addition to P-values, comparisons were also scored by percentage identity. Percentage identity reflects the degree to which two segments of DNA or protein are identical over a particular length. The identified homologous polynucleotide and polypeptide sequences and homologues of the *Arabidopsis* polynucleotides and polypeptides may be orthologs of the *Arabidopsis* polynucleotides and polypeptides.

As shown in Table 6, polynucleotide and polypeptide sequences which were identified as orthologous and homologous of SEQ ID NOs:1 and 2 were found in *Gossypium arboreum, Glycine max, Zea mays, Gossypium hirsutum, Medicago truncatula, Lycopersicon esculentum, Solanum tuberosum, Triticum aestivum, Hordeum vulgare, Triticum monococcum, Oryza sativa, Vernonia galamensis, Argemone mexicana,* and *Triticum aestivum.*

As shown in Table 6, polynucleotide and polypeptide sequences which were identified as orthologous and homologous of SEQ ID NOs:3 and 4 were found in *Brassica oleracea, Lycopersicon esculentum, Lycopersicon pennellii, Lotus japonicus, Oryza sativa, Solanum tuberosum, Medicago truncatula, Glycine max, Euphorbia esula, Gossypium arboreum, Antirrhinum hispanicum, Oryza sativa (japonica* cultivar-group), and *Triticum aestivum*. Additional orthologous and homologous polynucleotides and polypeptide sequences from other plant species are shown in Table 7.

All references, publications, patent documents, web pages, and other documents cited or mentioned herein are hereby incorporated by reference in their entirety for all purposes. Although the invention has been described with reference to specific embodiments and examples, it should be understood that one of ordinary skill can make various modifications without departing from the spirit of the invention. The scope of the invention is not limited to the specific embodiments and examples provided.

TABLE 6

| SEQ ID NO | Gene ID | Test Sequence ID | Smallest Sum Probability | Test Sequence Species | Test Sequence GenBank Annotation |
|---|---|---|---|---|---|
| 1 | G481 | BG440251 | 9.00E−42 | [*Gossypium arboreum*] | GA_Ea0006K20f *Gossypium arboreum* 7-10 d |
| 1 | G481 | BM887558 | 3.90E−41 | [*Glycine max*] | sam40c09.y1 Gm-c1068 *Glycine max* cDNA clone SOY |
| 1 | G481 | ZMNFYB | 1.70E−40 | [*Zea mays*] | Z.mays mRNA for CAAT-box DNA binding protein subun |
| 1 | G481 | AI728916 | 2.40E−40 | [*Gossypium hirsutum*] | BNLGHi12022 Six-day Cotton fiber *Gossypi* |
| 1 | G481 | AW775623 | 3.80E−40 | [*Medicago truncatula*] | EST334688 DSIL *Medicago truncatula* cDNA |
| 1 | G481 | AW738727 | 9.80E−40 | [*Lycopersicon esculentum*] | EST340154 tomato flower buds, anthe |
| 1 | G481 | BG599785 | 1.70E−38 | [*Solanum tuberosum*] | EST504680 cSTS *Solanum tuberosum* cDNA clo |
| 1 | G481 | BE413647 | 2.50E−38 | [*Triticum aestivum*] | SCU001.E10.R990714 ITEC SCU Wheat Endospe |
| 1 | G481 | BF065056 | 5.80E−38 | [*Hordeum vulgare*] | HV_CEb0022M01f *Hordeum vulgare* seedling gre |
| 1 | G481 | BG314203 | 1.00E−37 | [*Triticum monococcum*] | WHE2460_ E10 _I20ZS *Triticum monococcum* i |
| 1 | G481 | gi22380 | 1.10E−45 | [*Zea mays*] | CAAT-box DNA binding protein subunit B (NF-YB). |
| 1 | G481 | gi15408794 | 2.60E−30 | [*Oryza sativa*] | putative CCAAT-binding transcription factor |
| 1 | G481 | gi16902054 | 1.00E−28 | [*Vernonia galamensis*] | CCAAT-box binding factor HAP3 B domai |
| 1 | G481 | gi16902050 | 2.70E−28 | [*Glycine max*] | CCAAT-box binding factor HAP3 B domain. |
| 1 | G481 | gi16902056 | 4.30E−28 | [*Argemone mexicana*] | CCAAT-box binding factor HAP3 B domain. |
| 1 | G481 | gi16902058 | 1.50E−23 | [*Triticum aestivum*] | CCAAT-box binding factor HAP3 B domain. |
| 3 | G1466 | BH596941 | 1.40E−65 | [*Brassica oleracea*] | BOHFG41TR BOHF *Brassica oleracea* genomic |
| 3 | G1466 | BE462774 | 0.00014 | [*Lycopersicon esculentum*] | EST325108 tomato flower buds 0-3 mm |
| 3 | G1466 | AW399721 | 0.00049 | [*Lycopersicon pennellii*] | EST310221 *L. pennellii* trichome, Cor |
| 3 | G1466 | AV413010 | 0.00054 | [*Lotus japonicus*] | AV413010 *Lotus japonicus* young plants (two- |
| 3 | G1466 | OSJN00182 | 0.0029 | [*Oryza sativa*] | chromosome 4 clone OSJNBa0086O06, *** SEQUENC |
| 3 | G1466 | BG599234 | 0.0047 | [*Solanum tuberosum*] | EST504134 cSTS *Solanum tuberosum* cDNA clo |
| 3 | G1466 | BG580068 | 0.0095 | [*Medicago truncatula*] | EST481790 GVN *Medicago truncatula* cDNA |
| 3 | G1466 | BI316339 | 0.026 | [*Glycine max*] | saf02a08.y1 Gm-c1065 *Glycine max* cDNA clone GEN |
| 3 | G1466 | BG409415 | 0.026 | [*Euphorbia esula*] | 00787 leafy spurge Lambda HybriZAP 2.1 two- |
| 3 | G1466 | BF278686 | 0.11 | [*Gossypium arboreum*] | GA_Eb0035E21f *Gossypium arboreum* 7-10 d |
| 3 | G1466 | gi8096405 | 2.30E−12 | [*Oryza sativa*] | Similar to *Arabidopsis thaliana* chromosome 1 |
| 3 | G1466 | gi13161526 | 3.40E−08 | [*Antirrhinum hispanicum*] | S locus F-box (SLF)-S2 protein. |
| 3 | G1466 | gi18844804 | 0.083 | [*Oryza sativa (japonica* cultivar-group)] | contains ESTs D151 |
| 3 | G1466 | gi9858770 | 0.83 | [*Lycopersicon esculentum*] | BAC19.2. |
| 3 | G1466 | gi6505722 | 1 | [*Triticum aestivum*] | ribosomal RNA apurinic site specific ly |

TABLE 7

| SEQ ID NO | Gene ID | Test Sequence ID | Test Sequence GenBank Annotation | Reading Frame | High Score | Smallest Sum Probability | N |
|---|---|---|---|---|---|---|---|
| 1 | G481 | BG440251 | BG440251 GA_Ea0006K20f *Gossypium arboreum* 7 . . . | 3 | 263 | 9.00E−42 | 2 |
| 1 | G481 | BM887558 | BM887558 sam40c09.y1 Gm-c1068 *Glycine max* cD . . . | 3 | 268 | 3.90E−41 | 2 |
| 1 | G481 | BG362898 | BG362898 sac13e07.y1 Gm-c1040 *Glycine max* cD . . . | 3 | 263 | 4.90E−41 | 2 |
| 1 | G481 | AW395227 | AW395227 sh45e04.y1 Gm-c1017 *Glycine max* cDN . . . | 1 | 264 | 9.10E−41 | 2 |
| 1 | G481 | BM525962 | BM525962 sak74b11.y1 Gm-c1036 *Glycine max* cD . . . | 3 | 264 | 9.20E−41 | 2 |
| 1 | G481 | BI972318 | BI972318 sag90a01.y1 Gm-c1084 *Glycine max* cD . . . | 3 | 264 | 9.70E−41 | 2 |
| 1 | G481 | BG363233 | BG363233 sac11h11.y1 Gm-c1040 *Glycine max* cD . . . | 3 | 264 | 9.90E−41 | 2 |
| 1 | G481 | BE021941 | BE021941 sm64d05.y1 Gm-c1028 *Glycine max* cDN . . . | 1 | 264 | 1.00E−40 | 2 |
| 1 | G481 | BI316766 | BI316766 saf73a12.y1 Gm-c1078 *Glycine max* cD . . . | 3 | 264 | 1.10E−40 | 2 |
| 1 | G481 | BE803572 | BE803572 sr60e11.y1 Gm-c1052 *Glycine max* cDN . . . | 2 | 264 | 1.10E−40 | 2 |
| 1 | G481 | ZMNFYB | X59714 Z.mays mRNA for CAAT-box DNA binding . . . | 2 | 262 | 1.70E−40 | 2 |
| 1 | G481 | BF071234 | BF071234 st06h05.y1 Gm-c1065 *Glycine max* cDN . . . | 3 | 258 | 2.00E−40 | 2 |
| 1 | G481 | AI728916 | AI728916 BNLGHi12022 Six-day Cotton fiber Go . . . | 3 | 261 | 2.40E−40 | 2 |
| 1 | G481 | BF597252 | BF597252 su96c06.y1 Gm-c1056 *Glycine max* cDN . . . | 2 | 264 | 2.90E−40 | 2 |
| 1 | G481 | AW597630 | AW597630 sj96g06.y1 Gm-c1023 *Glycine max* cDN . . . | 2 | 259 | 3.40E−40 | 2 |
| 1 | G481 | AW775623 | AW775623 EST334688 DSIL *Medicago truncatula* . . . | 2 | 259 | 3.80E−40 | 2 |
| 1 | G481 | AW733618 | AW733618 sk75h06.y1 Gm-c1016 *Glycine max* cDN . . . | 3 | 257 | 6.00E−40 | 2 |
| 1 | G481 | AW738727 | AW738727 EST340154 tomato flower buds, anthe . . . | 1 | 249 | 9.80E−40 | 2 |
| 1 | G481 | BG642751 | BG642751 EST510945 tomato shoot/meristem *Lyc* . . . | 1 | 249 | 9.90E−40 | 2 |
| 1 | G481 | BE441135 | BE441135 EST408405 tomato developing/immatur . . . | 1 | 249 | 9.90E−40 | 2 |
| 1 | G481 | AW621652 | AW621652 EST312450 tomato root during/after . . . | 1 | 249 | 1.10E−39 | 2 |
| 1 | G481 | AI900024 | AI900024 sb97g11.y1 Gm-c1012 *Glycine max* cDN . . . | 1 | 264 | 3.20E−39 | 2 |

TABLE 7-continued

| SEQ ID NO | Gene ID | Test Sequence ID | Test Sequence GenBank Annotation | Reading Frame | High Score | Smallest Sum Probability | N |
|---|---|---|---|---|---|---|---|
| 1 | G481 | BG445358 | BG445358 GA_Ea0027N18f *Gossypium arboreum* 7 . . . | 2 | 243 | 1.40E-38 | 2 |
| 1 | G481 | BG599785 | BG599785 EST504680 cSTS *Solanum tuberosum* cD . . . | 2 | 254 | 1.70E-38 | 2 |
| 1 | G481 | BG350430 | BG350430 091D09 Mature tuber lambda ZAP *Sola* . . . | 3 | 254 | 1.70E-38 | 2 |
| 1 | G481 | BE413647 | BE413647 SCU001.E10.R990714 ITEC SCU Wheat E . . . | 3 | 248 | 2.50E-38 | 2 |
| 1 | G481 | BE516510 | BE516510 WHE611_D10_H19ZA Wheat ABA-treated . . . | 2 | 248 | 3.00E-38 | 2 |
| 1 | G481 | BF065056 | BF065056 HV_CEb0022M01f *Hordeum vulgare* seed . . . | 3 | 247 | 5.80E-38 | 2 |
| 1 | G481 | BG314203 | BG314203 WHE2460_E10_I20ZS *Triticum monococc* . . . | 1 | 243 | 1.00E-37 | 2 |
| 1 | G481 | AI725612 | AI725612 BNLGHi12445 Six-day Cotton fiber Go . . . | 2 | 247 | 1.20E-37 | 2 |
| 1 | G481 | AL387357 | AL387357 MtBC42A04F1 MtBC *Medicago truncatul* . . . | 3 | 231 | 2.00E-37 | 2 |
| 1 | G481 | AW907348 | AW907348 EST343471 potato stolon, Cornell Un . . . | 2 | 246 | 2.40E-37 | 2 |
| 1 | G481 | BG274786 | BG274786 WHE2234_C03_E06ZS *Aegilops speltoid* . . . | 1 | 248 | 2.50E-37 | 2 |
| 1 | G481 | AW459387 | AW459387 sh23f03.y1 Gm-c1016 *Glycine max* cDN . . . | 2 | 233 | 3.40E-37 | 2 |
| 1 | G481 | BE804236 | BE804236 sr77b04.y1 Gm-c1052 *Glycine max* cDN . . . | 2 | 254 | 4.30E-37 | 2 |
| 1 | G481 | BE210041 | BE210041 so38b01.y1 Gm-c1039 *Glycine max* cDN . . . | 3 | 231 | 5.70E-37 | 2 |
| 1 | G481 | AW980494 | AW980494 EST391647 GVN *Medicago truncatula* c . . . | 1 | 229 | 6.30E-37 | 2 |
| 1 | G481 | BG263362 | BG263362 WHE2341_B02_C03ZS Wheat pre-anthesi . . . | 1 | 238 | 7.10E-37 | 2 |
| 1 | G481 | BH532457 | BH532457 BOGLV08TR BOGL *Brassica oleracea* ge . . . | 2 | 225 | 8.00E-37 | 2 |
| 1 | G481 | BG847452 | BG847452 1024017D03.y1 *C. reinhardtii* CC-169 . . . | 2 | 236 | 8.20E-37 | 2 |
| 1 | G481 | BG857007 | BG857007 1024049D01.y1 *C. reinhardtii* CC-169 . . . | 3 | 236 | 9.30E-37 | 2 |
| 1 | G481 | BG858372 | BG858372 1024057C11.y1 *C. reinhardtii* CC-169 . . . | 3 | 236 | 9.50E-37 | 2 |
| 1 | G481 | BG850689 | BG850689 1024029A11.y2 *C. reinhardtii* CC-169 . . . | 2 | 236 | 9.50E-37 | 2 |
| 1 | G481 | BI718232 | BI718232 1031024F10.y1 *C. reinhardtii* CC-169 . . . | 3 | 236 | 9.70E-37 | 2 |
| 1 | G481 | BI719728 | BI719728 1031045D08.y1 *C. reinhardtii* CC-169 . . . | 3 | 236 | 9.80E-37 | 2 |
| 1 | G481 | BI875221 | BI875221 963122G10.y1 *C. reinhardtii* CC-1690 . . . | 3 | 236 | 9.90E-37 | 2 |
| 1 | G481 | BE496857 | BE496857 WHE0761_D09_H17ZS Wheat heat-stress . . . | 1 | 238 | 1.00E-36 | 2 |
| 1 | G481 | BF651151 | BF651151 NF101H10EC1F1090 Elicited cell cult . . . | 3 | 227 | 1.10E-36 | 2 |
| 1 | G481 | BE441739 | BE441739 925009A11.x1 *C. reinhardtii* CC-2290 . . . | 2 | 236 | 1.30E-36 | 2 |
| 1 | G481 | BG846124 | BG846124 1024012C11.y1 *C. reinhardtii* CC-169 . . . | 1 | 234 | 1.50E-36 | 2 |
| 1 | G481 | AX288144 | AX288144 Sequence 15 from Patent WO0177311 . . . | 2 | 231 | 2.90E-36 | 2 |
| 1 | G481 | AW570530 | AW570530 sj63c01.y1 Gm-c1033 *Glycine max* cDN . . . | 2 | 263 | 2.90E-36 | 2 |
| 1 | G481 | AX180950 | AX180950 Sequence 1 from Patent WO0145493. 8 . . . | 2 | 231 | 3.30E-36 | 2 |
| 1 | G481 | BF585526 | BF585526 FM1_23_E09.gl_A003 Floral-Induced M . . . | 1 | 224 | 3.50E-36 | 2 |
| 1 | G481 | BI271802 | BI271802 NF013D06FL1F1057 Developing flower . . . | 1 | 226 | 5.40E-36 | 2 |
| 1 | G481 | BF270944 | BF270944 GA_Eb0010B11f *Gossypium arboreum* 7 . . . | 1 | 240 | 5.60E-36 | 2 |
| 1 | G481 | AI731275 | AI731275 BNLGHi9078 Six-day Cotton fiber Gos . . . | 2 | 221 | 1.30E-35 | 2 |
| 1 | G481 | BI967397 | BI967397 GM830001B20E03 Gm-r1083 *Glycine max* . . . | -3 | 226 | 1.40E-35 | 2 |
| 1 | G481 | BF585616 | BF585616 FM1_23_E09.bl_A003 Floral-Induced M . . . | 1 | 265 | 1.80E-35 | 2 |
| 1 | G481 | BF263449 | BF263449 HV_CEa0006M10f *Hordeum vulgare* seed . . . | 1 | 230 | 2.70E-35 | 2 |
| 1 | G481 | BF263455 | BF263455 HV_CEa0006M16f *Hordeum vulgare* seed . . . | 1 | 230 | 2.70E-35 | 2 |
| 1 | G481 | BF459554 | BF459554 061A04 Mature tuber lambda ZAP *Sola* . . . | 2 | 227 | 2.90E-35 | 2 |
| 1 | G481 | BF460267 | BF460267 073E08 Mature tuber lambda ZAP *Sola* . . . | 2 | 209 | 3.00E-35 | 3 |
| 1 | G481 | BG594268 | BG594268 EST492946 cSTS *Solanum tuberosum* cD . . . | 3 | 236 | 5.10E-35 | 2 |
| 1 | G481 | BI469382 | BI469382 sai11b10.y1 Gm-c1053 *Glycine max* cD . . . | 1 | 225 | 5.50E-35 | 2 |
| 1 | G481 | AI731250 | AI731250 BNLGH19010 Six-day Cotton fiber Gos . . . | 3 | 236 | 6.40E-35 | 2 |
| 1 | G481 | BG850688 | BG850688 1024029A1141 *C. reinhardtii* CC-169 . . . | 2 | 236 | 7.50E-35 | 2 |
| 1 | G481 | AW132359 | AW132359 se03b02.y1 Gm-c1013 *Glycine max* cDN . . . | 1 | 264 | 8.10E-35 | 2 |
| 1 | G481 | BM269434 | BM269434 MEST409-G11.univ ISUM5-RN *Zea mays* . . . | -2 | 216 | 8.70E-35 | 2 |
| 1 | G481 | AW035570 | AW035570 EST281308 tomato callus, TAMU *Lycop* . . . | 3 | 249 | 9.30E-35 | 2 |
| 1 | G481 | BE418716 | BE418716 SCL074.B01R990724 ITEC SCL Wheat Le . . . | 1 | 227 | 1.20E-34 | 2 |
| 1 | G481 | AW648378 | AW648378 EST326832 tomato germinating seedli . . . | 1 | 223 | 1.20E-34 | 2 |
| 1 | G481 | AV424305 | AV424305 AV424305 *Lotus japonicus* young plan . . . | -3 | 219 | 1.50E-34 | 2 |
| 1 | G481 | BF715909 | BF715909 saa11e08.y1 Gm-c1058 *Glycine max* cD . . . | 3 | 222 | 2.20E-34 | 2 |
| 1 | G481 | BI423967 | BI423967 sah64c11.y1 Gm-c1049 *Glycine max* cD . . . | 1 | 215 | 2.30E-34 | 2 |
| 1 | G481 | BG890447 | BG890447 EST516298 cSTD *Solanum tuberosum* cD . . . | 2 | 220 | 3.00E-34 | 2 |
| 1 | G481 | AI495007 | AI495007 sa89f03.y1 Gm-c1004 *Glycine max* cDN . . . | 3 | 220 | 5.70E-34 | 2 |
| 1 | G481 | AW760103 | AW760103 sl58b03.y1 Gm-cl 027 *Glycine max* cDN . . . | 3 | 225 | 7.40E-34 | 2 |
| 1 | G481 | BF517889 | BF517889 NXSI_029_D01_F NXSI (Nsf Xylem Side . . . | 3 | 222 | 1.70E-33 | 2 |
| 1 | G481 | BE060015 | BE060015 sn39tT06.y-1 Gm-c1027 *Glycine max* cDN . . . | 2 | 219 | 1.90E-33 | 2 |
| 1 | G481 | AW625817 | AW625817 EST319724 tomato radicle, 5 d post- . . . | 3 | 211 | 2.90E-33 | 2 |
| 1 | G481 | AW397727 | AW397727 sg83f04.y1 Gm-cl 026 *Glycine max* cDN . . . | 3 | 210 | 3.10E-33 | 2 |
| 1 | G481 | BI207873 | BI207873 EST525913 cTOS *Lycopersicon esculen* . . . | 2 | 227 | 3.20E-33 | 2 |
| 1 | G481 | AV632945 | AV632945 AV632945 *Chlamydomonas reinhardtii* . . . | 3 | 236 | 3.40E-33 | 2 |
| 1 | G481 | AW931634 | AW931634 EST357477 tomato fruit mature green . . . | 1 | 223 | 4.90E-33 | 2 |
| 1 | G481 | BM888735 | BM888735 952068E04.y1 952 - BMS tissue from . . . | 2 | 214 | 5.10E-33 | 2 |
| 1 | G481 | AI486503 | AI486503 EST244824 tomato ovary, TAMU *Lycope* . . . | 3 | 223 | 5.40E-33 | 2 |
| 1 | G481 | BE641101 | BE641101 Cri2_2_ E11_SP6 *Ceratopteris* Spore L . . . | 3 | 224 | 8.60E-33 | 2 |
| 1 | G481 | BI953657 | BI953657 HVSMEm0013M03f *Hordeum vulgare* gree . . . | 1 | 230 | 9.80E-33 | 2 |
| 1 | G481 | BM341536 | BM341536 MEST336-C11.T3 ISUM5-RN *Zea mays* cD . . . | -1 | 214 | 1.80E-32 | 2 |
| 1 | G481 | AX180957 | AX180957 Sequence 8 from Patent WO0145493. 8 . . . | 2 | 231 | 2.70E-32 | 2 |
| 1 | G481 | AW201996 | AW201996 sf09g11.y1 Gm-c1027 *Glycine max* cDN . . . | 1 | 207 | 2.90E-32 | 2 |
| 1 | G481 | BG135204 | BG135204 EST468096 tomato crown gall *Lycoper* . . . | 3 | 230 | 3.20E-32 | 2 |
| 1 | G481 | BI406257 | BI406257 158C12 Mature tuber lambda ZAP *Sola* . . . | 2 | 201 | 1.20E-31 | 2 |
| 1 | G481 | BM341107 | BM341107 MEST330-D11.T3 ISUM5-RN *Zea mays* cD . . . | -1 | 214 | 1.30E-31 | 2 |
| 1 | G481 | AI782351 | AI782351 EST263230 tomato susceptible, Corne . . . | 2 | 208 | 2.50E-31 | 2 |
| 1 | G481 | BM331836 | BM331836 MEST171-B11.T3 ISUM5-RN *Zea mays* cD . . . | -3 | 214 | 3.30E-31 | 2 |
| 1 | G481 | BM268414 | BM268414 MEST395-C12.univ ISUM5-RN *Zea mays* . . . | -2 | 214 | 3.40E-31 | 2 |

TABLE 7-continued

| SEQ ID NO | Gene ID | Test Sequence ID | Test Sequence GenBank Annotation | Reading Frame | High Score | Smallest Sum Probability | N |
|---|---|---|---|---|---|---|---|
| 1 | G481 | BM337630 | BM337630 MEST215-B12.T3 ISUM5-RN *Zea mays* cD... | −2 | 214 | 3.40E-31 | 2 |
| 1 | G481 | BM349646 | BM349646 MEST253-D11.T3 ISUM5-RN *Zea mays* cD... | −2 | 214 | 3.40E-31 | 2 |
| 1 | G481 | BE356560 | BE356560 DG1 126 D05.bl_A002 Dark Grown 1 (D... | 3 | 265 | 3.70E-31 | 2 |
| 1 | G481 | AV632044 | AV632044 AV632044 *Chlamydomonas reinhardtii*... | 2 | 236 | 4.50E-31 | 2 |
| 1 | G481 | BE054369 | BE054369 GA_Ea0002A05f *Gossypium arboreum* 7... | 1 | 263 | 5.80E-31 | 2 |
| 1 | G481 | AC108500 | AC108500 *Oryza sativa* chromosome 5 clone OJ1... | −3 | 230 | 6.20E-31 | 2 |
| 1 | G481 | BI129814 | BI129814 G095P88Y *Populus* cambium cDNA libra... | 1 | 266 | 6.90E-31 | 2 |
| 1 | G481 | BG318871 | BG318871 NXPV_020_H08_F NXPV (Nsf Xylem Plan... | 1 | 216 | 7.60E-31 | 2 |
| 1 | G481 | AV420653 | AV420653 AV420653 *Lotus japonicus* young plan... | 1 | 256 | 1.70E-30 | 2 |
| 1 | G481 | AW348165 | AW348165 GM210001A21D7 Gm-r1021 *Glycine max*... | −3 | 196 | 4.60E-30 | 2 |
| 1 | G481 | AI442376 | AI442376 sa26b07.y1 Gm-c1004 *Glycine max* cDN... | 2 | 197 | 5.10E-30 | 2 |
| 1 | G481 | AI442765 | AI442765 sa26b07.x1 Gm-c1004 *Glycine max* cDN... | −1 | 192 | 1.70E-29 | 2 |
| 1 | G481 | BE604847 | BE604847 WHE1713-1716_D19_D19ZS Wheat heat s... | 3 | 241 | 1.90E-29 | 2 |
| 1 | G481 | AW043377 | AW043377 ST32F09 Pine TriplEx shoot tip libr... | 1 | 233 | 3.90E-29 | 2 |
| 1 | G481 | AP003271 | AP003271 *Oryza sativa* genomic DNA, chromosom... | −2 | 240 | 7.60E-29 | 2 |
| 1 | G481 | BG832836 | BG832836 NXPV_081_C10_F NXPV (Nsf Xylem Plan... | 1 | 222 | 9.10E-29 | 2 |
| 1 | G481 | AP004366 | AP004366 *Oryza sativa* chromosome 1 clone P04... | −3 | 240 | 9.30E-29 | 2 |
| 1 | G481 | BE603222 | BE603222 HVSMEh0102J16f *Hordeum vulgare* 5-45... | 2 | 204 | 3.50E-28 | 2 |
| 1 | G481 | AW754604 | AW754604 PC04B12 Pine TriplEx pollen cone li... | 2 | 197 | 3.70E-28 | 2 |
| 1 | G481 | AW756413 | AW756413 sl21a12.y1 Gm-c1036 *Glycine max* cDN... | 1 | 201 | 4.00E-28 | 2 |
| 1 | G481 | AW432980 | AW432980 siO3a01.y1 Gm-c1029 *Glycine max* cDN... | 3 | 201 | 4.40E-28 | 2 |
| 1 | G481 | BG551755 | BG551755 sad42f11.y1 Gm-c1075 *Glycine max* cD... | 3 | 201 | 4.80E-28 | 2 |
| 1 | G481 | BF595304 | BF595304 su76f03.y1 Gm-c1055 *Glycine max* cDN... | 2 | 201 | 5.10E-28 | 2 |
| 1 | G481 | BM308208 | BM308208 sak43a12.y1 Gm-c1036 *Glycine max* cD... | 2 | 200 | 5.20E-28 | 2 |
| 1 | G481 | AC104284 | AC104284 *Oryza sativa* chromosome 5 clone OJ1... | −3 | 224 | 5.70E-28 | 2 |
| 1 | G481 | BM528842 | BM528842 sak69b03.y1 Gm-c1036 *Glycine max* cD... | 2 | 200 | 5.70E-28 | 2 |
| 1 | G481 | BI268123 | BI268123 NF116D11IN1F1094 Insect herbivory M... | 3 | 224 | 9.10E-28 | 2 |
| 1 | G481 | AW981720 | AW981720 PC15H07 Pine TriplEx pollen cone li... | 3 | 204 | 9.10E-28 | 2 |
| 1 | G481 | AA660543 | AA660543 00429 MtRHE *Medicago truncatula* cDN... | 3 | 187 | 1.30E-27 | 2 |
| 1 | G481 | BE726750 | BE726750 894093C12.y3 *C. reinhardtii* CC-1690... | 2 | 236 | 1.90E-27 | 2 |
| 1 | G481 | BI309186 | BI309186 EST530596 GPOD *Medicago truncatula*... | 2 | 224 | 4.00E-27 | 2 |
| 1 | G481 | AW931376 | AW931376 EST357219 tomato fruit mature green... | 2 | 244 | 7.10E-27 | 2 |
| 1 | G481 | BF636140 | BF636140 NF060H09DT1F1079 Drought *Medicago* t... | 3 | 224 | 1.70E-26 | 2 |
| 1 | G481 | BG526135 | BG526135 57-6 Stevia field grown leaf cDNA S... | −1 | 228 | 2.50E-26 | 2 |
| 1 | G481 | BI311277 | BI311277 EST5313027 GESD *Medicago truncatula*... | −2 | 192 | 2.60E-26 | 2 |
| 1 | G481 | BI721770 | BI721770 1031057H04.y1 *C. reinhardtii* CC-169... | 2 | 212 | 2.90E-26 | 2 |
| 1 | G481 | AW200790 | AW200790 se93e11.y1 Gm-c1027 *Glycine max* cDN... | 2 | 225 | 3.50E-26 | 2 |
| 1 | G481 | AY058919 | AY058919 *Vernonia galamensis* CCAAT-box bindi... | 1 | 187 | 3.80E-26 | 2 |
| 1 | G481 | BM109471 | BM109471 EST557007 potato roots *Solanum tube*... | 3 | 220 | 4.20E-26 | 2 |
| 1 | G481 | AY058917 | AY058917 *Glycine max* clone se2.11d12 CCAAT-b... | 1 | 188 | 1.00E-25 | 2 |
| 1 | G481 | AY058920 | AY058920 *Argemone mexicana* CCAAT-box binding... | 1 | 189 | 1.30E-25 | 2 |
| 1 | G481 | AU088581 | AU088581 Rice callus *Oryza sativa* c... | 2 | 178 | 1.40E-25 | 2 |
| 1 | G481 | AW720671 | AW720671 LjNEST6a3rc *Lotus japonicus* nodule... | 2 | 192 | 2.10E-25 | 2 |
| 1 | G481 | BI419749 | BI419749 LjNEST14e12r*Lotus japonicus* nodule... | 1 | 192 | 2.10E-25 | 2 |
| 1 | G481 | AW719547 | AW719547 LjNEST6a3r *Lotus japonicus* nodule I... | 2 | 192 | 2.20E-25 | 2 |
| 1 | G481 | BM134935 | BM134935 WHE0460_A02_A03ZS Wheat Fusarium gr... | 2 | 211 | 2.60E-25 | 2 |
| 1 | G481 | AI965590 | AI965590 sc74b05.y1 Gm-c1018 *Glycine max* cDN... | 2 | 208 | 4.00E-25 | 2 |
| 1 | G481 | BI875522 | BI875522 963125B06.y1 *C. reinhardtii* CC-1690... | 3 | 212 | 5.70E-25 | 2 |
| 1 | G481 | BI531782 | BI531782 1024116E03.y1 *C. reinhardtii* CC-169... | 3 | 212 | 5.90E-25 | 2 |
| 1 | G481 | AW688588 | AW688588 NF009C11ST1F1000 Developing stem Me... | 2 | 218 | 8.00E-25 | 2 |
| 1 | G481 | BG368375 | BG368375 HVSMEi0018C01f *Hordeum vulgare* 20 D... | 1 | 214 | 8.20E-25 | 2 |
| 1 | G481 | BF270164 | BF270164 GA_Eb0007A21f *Gossypium arboreum* 7... | 2 | 206 | 1.70E-24 | 2 |
| 1 | G481 | BH472297 | BH472297 BOGJF90TF BOGJ *Brassica oleracea* ge... | 1 | 187 | 1.70E-24 | 2 |
| 1 | G481 | AY058918 | AY058918 *Glycine max* clone ses2w.pk0015.a4 C... | 1 | 178 | 1.10E-23 | 2 |
| 1 | G481 | BF291752 | BF291752 WHE2205_F04_K07ZS *Aegilops speltoid*... | 3 | 205 | 1.10E-23 | 2 |
| 1 | G481 | BF169598 | BF169598 NXCI_125_B04_F NXCI (Nsf Xylem Comp... | 2 | 210 | 8.30E-23 | 2 |
| 1 | G481 | BH470962 | BH470962 BOGNF35TF BOGN *Brassica oleracea* ge... | 3 | 185 | 1.00E-22 | 2 |
| 1 | G481 | BI952722 | BI952722 HVSMEm0007I19f *Hordeum vulgare* gree... | 1 | 230 | 2.20E-22 | 2 |
| 1 | G481 | AL506199 | AL506199 AL506199 *Hordeum vulgare* Barke ... | 1 | 179 | 2.30E-22 | 2 |
| 1 | G481 | BH659234 | BH659234 BOMDK68TR BO_2_3_KB *Brassica olerac*... | 3 | 179 | 4.00E-22 | 2 |
| 1 | G481 | BE802539 | BE802539 sr32f02.y1 Gm-c1050 *Glycine max* cDN... | 2 | 221 | 1.40E-21 | 2 |
| 1 | G481 | BE196056 | BE196056 HVSMEh0091D23f *Hordeum vulgare* 5-45... | 3 | 211 | 1.60E-21 | 2 |
| 1 | G481 | AL509098 | AL509098 AL509098 *Hordeum vulgare* Barke deve... | 3 | 179 | 2.70E-21 | 2 |
| 1 | G481 | AP003266 | AP003266 *Oryza sativa* genomic DNA, chromosom... | −3 | 194 | 3.00E-21 | 2 |
| 1 | G481 | AF410176 | AF410176 *Zea mays* leafy cotyledon) (Lec1) mR... | 3 | 179 | 3.30E-21 | 2 |
| 1 | G481 | AX365282 | AX365282 Sequence 18 from Patent WO0206499... | 3 | 179 | 3.30E-21 | 2 |
| 1 | G481 | AY058921 | AY058921 *Triticum aestivum* CCAAT-box binding... | 1 | 175 | 5.70E-21 | 2 |
| 1 | G481 | BG662094 | BG662094 Ljirnpest38-110-g8 Ljirnp Lambda Hy... | 1 | 266 | 8.90E-20 | 1 |
| 1 | G481 | BH645253 | BH645253 BOMFL56TR BO_2_3_KB *Brassica olerac*... | 3 | 166 | 2.70E-19 | 2 |
| 1 | G481 | AP004179 | AP004179 *Oryza sativa* chromosome 2 clone OJ1... | 3 | 180 | 4.60E-19 | 2 |
| 1 | G481 | BM500534 | BM500534 PAC000000000627 Pioneer AF-1 array... | 1 | 179 | 8.20E-19 | 2 |
| 1 | G481 | BH701005 | BH701005 BOMMD16TR BO_2_3_KB *Brassica olerac*... | 2 | 248 | 5.60E-18 | 1 |
| 1 | G481 | BH678940 | BH678940 BOMIF09TF BO_23_KB *Brassica olerac*... | −1 | 244 | 1.10E-17 | 1 |
| 1 | G481 | AP004791 | AP004791 *Oryza sativa* (japonica cultivar-gro... | −1 | 183 | 9.20E-17 | 2 |
| 1 | G481 | BE121888 | BE121888 894015G05.y1 *C. reinhardtii* CC-1690... | 1 | 236 | 1.30E-16 | 1 |
| 1 | G481 | AX288136 | AX288136 Sequence 7 from Patent WO0177311. 1... | 3 | 231 | 3.90E-16 | 1 |

TABLE 7-continued

| SEQ ID NO | Gene ID | Test Sequence ID | Test Sequence GenBank Annotation | Reading Frame | High Score | Smallest Sum Probability | N |
|---|---|---|---|---|---|---|---|
| 1 | G481 | AV411210 | AV411210 AV411210 *Lotus japonicus* young plan . . . | 2 | 228 | 1.10E-15 | 1 |
| 1 | G481 | AV425835 | AV425835 AV425835 *Lotus japonicus* young plan . . . | 2 | 228 | 1.10E-15 | 1 |
| 1 | G481 | BI206716 | BI206716 EST524756 cTOS Lycopersicon esculen . . . | 3 | 227 | 1.10E-15 | 1 |
| 1 | G481 | BF645376 | BF645376 NF040B05EC1F1044 Elicited cell cult . . . | 2 | 224 | 1.90E-15 | 1 |
| 1 | G481 | BM347760 | BM347760 MEST281-G09.T3 ISUM5-RN *Zea mays* cD . . . | -3 | 219 | 6.10E-15 | 1 |
| 1 | G481 | AW648379 | AW648379 EST326833 tomato germinating seedli . . . | 1 | 218 | 1.40E-14 | 1 |
| 1 | G481 | BI176409 | BI176409 EST521199 P. infestans-challenged I . . . | 2 | 142 | 1.90E-14 | 2 |
| 1 | G481 | BM109406 | BM109406 EST556942 potato roots *Solanum tube* . . . | 1 | 214 | 1.90E-14 | 1 |
| 1 | G481 | BM348480 | BM348480 MEST291-E08.T3 ISUM5-RN *Zea mays* cD . . . | -3 | 214 | 2.30E-14 | 1 |
| 1 | G481 | BI531808 | BI531808 1024116G03.y1 C. reinhardtii CC-169 . . . | 3 | 122 | 2.70E-14 | 2 |
| 1 | G481 | BM158109 | BM158109 NXLV_029_E11_F NXLV (Nsf Xylem Late . . . | 3 | 212 | 4.40E-14 | 1 |
| 1 | G481 | AI966550 | AI966550 sc51h01.y1 Gm-c1015 *Glycine max* cDN . . . | 2 | 212 | 5.90E-14 | 1 |
| 1 | G481 | BM341073 | BM341073 MEST329-H08.T3 ISUM5-RN *Zea mays* cD . . . | -2 | 210 | 6.00E-14 | 1 |
| 1 | G481 | BM335521 | BM335521 MEST162-H08.T3 ISUM5-RN *Zea mays* cD . . . | -2 | 210 | 6.60E-14 | 1 |
| 1 | G481 | AV422691 | AV422691 AV422691 *Lotus japonicus* young plan . . . | 2 | 138 | 2.20E-13 | 2 |
| 1 | G481 | BG039303 | BG039303 NXSI_097_E11_F NXSI (Nsf Xylem Side . . . | 3 | 205 | 2.70E-13 | 1 |
| 1 | G481 | BF068031 | BF068031 st86h12.y1 Gm-c1054 *Glycine max* cDN . . . | 1 | 205 | 3.50E-13 | 1 |
| 1 | G481 | BF777951 | BF777951 NXSI_079_C03_F NXSI (Nsf Xylem Side . . . | 2 | 205 | 4.80E-13 | 1 |
| 1 | G481 | BI720257 | BI720257 1031048F06.y1 C. reinhardtii CC-169 . . . | 3 | 204 | 4.90E-13 | 1 |
| 1 | G481 | BM441686 | BM441686 EBed07_SQ001_E05_R IGF Barley EBed0 . . . | 2 | 115 | 1.70E-12 | 2 |
| 1 | G481 | AX365284 | AX365284 Sequence 20 from Patent WO0206499 . . . | 3 | 124 | 4.10E-12 | 2 |
| 1 | G481 | BH153040 | BH153040 Gm_ISb001_083_P16R ISU Soybean BAC . . . | -1 | 185 | 2.90E-11 | 1 |
| 1 | G481 | BG589029 | BG589029 EST490838 MHRP- *Medicago truncatula* . . . | 2 | 187 | 3.30E-11 | 1 |
| 1 | G481 | BG350792 | BG350792 098C07 Mature tuber lambda ZAP *Sola* . . . | 1 | 185 | 1.90E-10 | 1 |
| 1 | G481 | BM094268 | BM094268 sah27d01.y1 Gm-c1036 *Glycine max* cD . . . | 3 | 167 | 3.20E-09 | 1 |
| 1 | G481 | BM271333 | BM271333 sak08b06.y1 Gm-c1075 *Glycine max* cD . . . | 1 | 156 | 5.10E-08 | 1 |
| 1 | G481 | AW693654 | AW693654 NF066H08ST1F1000 Developing stem Me . . . | 3 | 161 | 6.30E-08 | 1 |
| 1 | G481 | C19290 | C19290 C19290 Rice panicle at ripening stage . . . | 1 | 153 | 1.40E-07 | 1 |
| 1 | G481 | AL388746 | AL388746 MtBC50E04F1 MtBC *Medicago truncatul* . . . | -2 | 145 | 8.90E-07 | 1 |
| 1 | G481 | BI068503 | BI068503 C022P78U *Populus* strain T89 leaves . . . | 1 | 142 | 2.70E-06 | 1 |
| 1 | G481 | BH591716 | BH591716 BOGTY51TR BOGT *Brassica oleracea* ge . . . | -2 | 139 | 3.50E-06 | 1 |
| 1 | G481 | BM333505 | BM333505 MEST156-F03.T3 ISUM5-RN *Zea mays* cD . . . | -2 | 138 | 4.40E-06 | 1 |
| 1 | G481 | BH645120 | BH645120 BOHZMO9TF BO_2_3_KB *Brassica olerac* . . . | 3 | 149 | 5.50E-06 | 1 |
| 1 | G481 | BM112643 | BM112643 EST560179 potato roots*Solanum tube* . . . | 2 | 143 | 9.40E-06 | 1 |
| 1 | G481 | BE356637 | BE356637 DG1_126_D05.g1_A002 Dark Grown 1 (D . . . | 1 | 133 | 1.80E-05 | 1 |
| 1 | G481 | BH580896 | BH580896 BOGLY95TR BOGL *Brassica oleracea* ge . . . | -2 | 146 | 2.20E-05 | 1 |
| 1 | G481 | BE400220 | BE400220 AWB001.E09F000328 ITEC AWB Wheat Me . . . | 3 | 132 | 2.20E-05 | 1 |
| 1 | G481 | AW981721 | AW981721 PC15H08 Pine TriplEx pollen cone li . . . | 2 | 129 | 4.40E-05 | 1 |
| 1 | G481 | BI325183 | BI325183 baa05b02.x1 Cassava EYC library1 Ma . . . | -1 | 124 | 0.00029 | 1 |
| 1 | G481 | BE822946 | BE822946 GM700019A20C12 Gm-r1070 *Glycine max* . . . | -3 | 130 | 0.00055 | 1 |
| 1 | G481 | BI271659 | BI271659 NF026A03FL1F1020 Developing flower . . . | 1 | 121 | 0.00076 | 1 |
| 1 | G481 | AMTAM4 | X59057 *A.majus* transposable element Tam4 DNA . . . | 2 | 134 | 0.0019 | 1 |
| 1 | G481 | BG653330 | BG653330 sad87a07.y1 Gm-c1055 *Glycine max* cD . . . | 3 | 114 | 0.0023 | 1 |
| 1 | G481 | BG644353 | BG644353 EST505972 KV3 *Medicago truncatula* c . . . | 2 | 126 | 0.004 | 1 |
| 1 | G481 | BG650027 | BG650027 sad90h01.y1 Gm-c1055 *Glycine max* cD . . . | 1 | 110 | 0.0056 | 1 |
| 1 | G481 | AW734322 | AW734322 sk81f11.y1 Gm-c1016 *Glycine max* cDN . . . | 3 | 110 | 0.0057 | 1 |
| 1 | G481 | BG046421 | BG046421 saa63e06.y1 Gm-c1060 *Glycine max* cD . . . | 2 | 110 | 0.0059 | 1 |
| 1 | G481 | BG726061 | BG726061 sae06d09.y1 Gm-c1055 *Glycine max* cD . . . | 3 | 110 | 0.0062 | 1 |
| 1 | G481 | BF070629 | BF070629 st23b12.y1 Gm-c1065 *Glycine max* cDN . . . | 1 | 110 | 0.0062 | 1 |
| 1 | G481 | AI443631 | AI443631 sa42e05.y1 Gm-c1004 *Glycine max* cD . . . | 2 | 110 | 0.0065 | 1 |
| 1 | G481 | 6F009637 | BF009637 sss81h09.y1 Gm-c1064 *Glycine max* cDN . . . | 1 | 109 | 0.0076 | 1 |
| 1 | G481 | BF627138 | BF627138 HVSMEb0004A20f *Hordeum vulgare* seed . . . | 1 | 125 | 0.008 | 1 |
| 1 | G481 | AV420244 | AV420244 AV420244 *Lotus japonicus* young plan . . . | 3 | 109 | 0.0085 | 1 |
| 1 | G481 | BH637694 | BH637694 1008018B12.2EL_x1 1008 - RescueMu G . . . | -2 | 111 | 0.0097 | 1 |
| 1 | G481 | AI967494 | AI967494 Ljirnpest03-196-b3 Ljirnp Lambda Hy . . . | 2 | 109 | 0.01 | 1 |
| 1 | G481 | AV416827 | AV416827 AV416827 *Lotus japonicus* young plan . . . | 1 | 109 | 0.011 | 1 |
| 1 | G481 | BG131195 | BG131195 EST464087 tomato crown gall *Lycoper* . . . | 3 | 107 | 0.012 | 1 |
| 1 | G481 | BF052943 | BF052943 EST438173 potato leaves and petiole . . . | 1 | 107 | 0.012 | 1 |
| 1 | G481 | AV409183 | AV409183 AV409183 *Lotus japonicus* young plan . . . | 3 | 108 | 0.015 | 1 |
| 1 | G481 | AW776198 | AW776198 EST335263 DSIL *Medicago truncatula* . . . | 1 | 105 | 0.022 | 1 |
| 1 | G481 | AL368819 | AL368819 MtBA27A03F1 MtBA *Medicago truncatul* . . . | 3 | 105 | 0.026 | 1 |
| 1 | G481 | C99407 | C99407 C99407 Rice panicle at ripening stage . . . | -3 | 105 | 0.026 | 1 |
| 1 | G481 | BH448006 | BH448006 BOGBH37TR BOGB *Brassica oleracea* ge . . . | -1 | 113 | 0.049 | 1 |
| 1 | G481 | AW185273 | AW185273 se89c10.y1 Gm-c1023 *Glycine max* cDN . . . | 3 | 110 | 0.061 | 1 |
| 1 | G481 | AW423569 | AW423569 sh68f08.y1 Gm-c1015 *Glycine max* cDN . . . | 3 | 110 | 0.065 | 1 |
| 1 | G481 | BG507868 | BG507868 sac82d02.y1 Gm-c1072 *Glycine max* cD . . . | 3 | 110 | 0.083 | 1 |
| 1 | G481 | C19737 | C19737 C19737 Rice panicle at ripening stage . . . | 3 | 100 | 0.089 | 1 |
| 1 | G481 | AW719575 | AW719575 LjNEST6a11r *Lotus japonicus* nodule . . . | 1 | 109 | 0.095 | 1 |
| 1 | G481 | AW706867 | AW706867 sk07d05.y1 Gm-c1023 *Glycine max* cDN . . . | 3 | 110 | 0.099 | 1 |
| 1 | G481 | A1460665 | A1460665 sa71g05.y1 Gm-c1004 *Glycine max* cDN . . . | 2 | 110 | 0.11 | 1 |
| 1 | G481 | AW759521 | AW759521 s144d11.y1 Gm-c1027 *Glycine max* cDN . . . | 2 | 110 | 0.11 | 1 |
| 1 | G481 | BF595796 | BF595796 sv04f12.y1 Gm-c1056 *Glycine max* cDN . . . | 2 | 110 | 0.11 | 1 |
| 1 | G481 | BM178052 | BM178052 saj68e01.y1 Gm-c1072 *Glycine max* cD . . . | 3 | 109 | 0.16 | 1 |
| 1 | G481 | BI424397 | BI424397 saf34c08.y4 Gm-c1077 *Glycine max* cD . . . | 1 | 110 | 0.16 | 1 |
| 1 | G481 | BG044257 | BG044257 saa25h07.y1 Gm-c1059 *Glycine max* cD . . . | 2 | 110 | 0.17 | 1 |
| 1 | G481 | AW234956 | AW234956 sf21b08.y1 Gm-c1028 *Glycine max* cDN . . . | 1 | 110 | 0.17 | 1 |

TABLE 7-continued

| SEQ ID NO | Gene ID | Test Sequence ID | Test Sequence GenBank Annotation | Reading Frame | High Score | Smallest Sum Probability | N |
|---|---|---|---|---|---|---|---|
| 1 | G481 | AW759820 | AW759820 s154e01.y1 Gm-c1027 *Glycine max* cDN . . . | 3 | 110 | 0.18 | 1 |
| 1 | G481 | AI959799 | AI959799 sc94d03.y1 Gm-c1019 *Glycine max* cDN . . . | 1 | 110 | 0.18 | 1 |
| 1 | G481 | AW201988 | AW201988 sf09f10.y1 Gm-c1027 *Glycine max* cDN . . . | 3 | 109 | 0.2 | 1 |
| 1 | G481 | AW164642 | AW164642 se74f06.y1 Gm-c1023 *Glycine max* cDN . . . | 3 | 110 | 0.2 | 1 |
| 1 | G481 | AT002114 | AT002114 AT002114 Flower bud cDNA *Brassica r* . . . | 2 | 98 | 0.23 | 1 |
| 1 | G481 | BF113032 | BF113032 EST440542 tomato breaker fruit *Lyco* . . . | 1 | 107 | 0.25 | 1 |
| 1 | G481 | BE659989 | BE659989 1010 GmaxSC *Glycine max* cDNA, mRNA . . . | 2 | 110 | 0.26 | 1 |
| 1 | G481 | OSA300218 | AJ300218 *Oryza sativa* nf-yb1 gene and nf-YB1 . . . | 2 | 111 | 0.27 | 1 |
| 1 | G481 | BG597547 | BG597547 EST496225 cSTS *Solanum tuberosum* cD . . . | 1 | 107 | 0.32 | 1 |
| 1 | G481 | BF644204 | BF644204 NF060B12EC1F1101 Elicited cell cult . . . | 2 | 105 | 0.33 | 1 |
| 1 | G481 | AF464906 | AF464906 *Glycine max* repressor protein (Dr1) . . . | 1 | 110 | 0.34 | 1 |
| 1 | G481 | BE436801 | BE436801 EST407919 tomato breaker fruit, TIG . . . | 2 | 107 | 0.36 | 1 |
| 1 | G481 | BE659987 | BE659987 7-F12 GmaxSC *Glycine max* cDNA, mRNA . . . | 1 | 109 | 0.36 | 1 |
| 1 | G481 | BG451060 | BG451060 NF098C04DT1F1024 Drought *Medicago t* . . . | 3 | 105 | 0.42 | 1 |
| 1 | G481 | BM436739 | BM436739 VVA009B06_53061 An expressed sequen . . . | 3 | 107 | 0.45 | 1 |
| 1 | G481 | BF273545 | BF273545 GA_Eb0018J12f *Gossypium arboreum* 7 . . . | 1 | 104 | 0.5 | 1 |
| 1 | G481 | BM411335 | BM411335 EST585662 tomato breaker fruit *Lyco* . . . | 3 | 107 | 0.5 | 1 |
| 1 | G481 | AW830697 | AW830697 sm06h11.y1 Gm-c1027 *Glycine max* cDN . . . | 2 | 91 | 0.54 | 1 |
| 1 | G481 | BE202566 | BE202566 EST392975 KV1 *Medicago truncatula* c . . . | 2 | 105 | 0.55 | 1 |
| 1 | G481 | BG240158 | BG240158 OV1_18_F02.b1_A002 Ovary 1 (OV1) So . . . | 3 | 101 | 0.56 | 1 |
| 1 | G481 | BM817060 | BM817060 HC01C02_T3.ab1 HC *Hordeum vulgare* c . . . | 1 | 103 | 0.58 | 1 |
| 1 | G481 | BE998485 | BE998485 EST430208 GVSN *Medicago truncatula* . . . | 3 | 105 | 0.58 | 1 |
| 1 | G481 | BE022456 | BE022456 sm74b08.y1 Gm-c1015 *Glycine max* cDN . . . | 2 | 103 | 0.6 | 1 |
| 1 | G481 | BF647976 | BF647976 NF013H04EC1F1042 Elicited cell cult . . . | 1 | 105 | 0.63 | 1 |
| 1 | G481 | BG102166 | BG102166 RHIZ2_21_F06.b1_A003 Rhizome2 (RHIZ . . . | 3 | 101 | 0.63 | 1 |
| 1 | G481 | AU084707 | AU084707 AU084707 *Cryptomeria japonica* inner . . . | 1 | 101 | 0.68 | 1 |
| 1 | G481 | BG648823 | BG648823 EST510442 HOGA *Medicago truncatula* . . . | 1 | 105 | 0.7 | 1 |
| 1 | G481 | BG648909 | BG648909 EST510528 HOGA *Medicago truncatula* . . . | 2 | 105 | 0.72 | 1 |
| 1 | G481 | BM380524 | BM380524 MEST521-B07.univ ISUM6 *Zea mays* cDN . . . | -3 | 103 | 0.75 | 1 |
| 1 | G481 | BG593107 | BG593107 EST491785 cSTS *Solanum tuberosum* cD . . . | 3 | 103 | 0.81 | 1 |
| 1 | G481 | BG052069 | BG052069 RHIZ2_5_F11.b1_A003 Rhizome2 (RHIZ2 . . . | 3 | 101 | 0.9 | 1 |
| 1 | G481 | BE497740 | BE497740 WHE0956_G06_M12ZS Wheat pre-anthesi . . . | 2 | 100 | 0.92 | 1 |
| 1 | G481 | BG873649 | BG873649 MEST8-E10.T7-1 ISUM3-TL *Zea mays* cD . . . | 3 | 101 | 0.94 | 1 |
| 1 | G481 | AW432997 | AW432997 siO3b08.y1 Gm-c1029 *Glycine max* cDN . . . | 2 | 88 | 0.96 | 1 |
| 1 | G481 | AW064635 | AW064635 ST33H06 Pine TriplEx shoot tip libr . . . | 2 | 100 | 0.96 | 1 |
| 1 | G481 | AX365283 | AX365283 Sequence 19 from Patent WO0206499. . . . | 1 | 101 | 0.97 | 1 |
| 1 | G481 | BG648613 | BG648613 EST510232 HOGA *Medicago truncatula* . . . | 3 | 99 | 0.993 | 1 |
| 1 | G481 | BE640725 | BE640725 Cri2_1_E07_SP6 *Ceratopteris* Spore L . . . | 2 | 100 | 0.995 | 1 |
| 1 | G481 | AF464902 | AF464902 *Oryza sativa* repressor protein (Dr1 . . . | 2 | 101 | 0.996 | 1 |
| 1 | G481 | AF464903 | AF464903 *Triticum aestivum* repressor protein . . . | 2 | 100 | 0.999 | 1 |
| 1 | G481 | BE449790 | BE449790 EST361228 tomato root, plants pre-a . . . | 3 | 97 | 0.9991 | 1 |
| 1 | G481 | B1206380 | B1206380 EST524420 cTOS *Lycopersicon esculen* . . . | 1 | 97 | 0.9996 | 1 |
| 1 | G481 | GI-22380 | CAAT-box DNA binding protein subunit B (N . . . | 1 | 262 | 1.10E-45 | 3 |
| 1 | G481 | GI-115840 | CBFA_MAIZE CCAAT-BINDING TRANSCRIPTION FAC . . . | 1 | 262 | 1.10E-45 | 3 |
| 1 | G481 | GI-7443522 | S22820 transcription factor NF-Y, CCAAT-bi . . . | 1 | 262 | 1.10E-45 | 3 |
| 1 | G481 | GI-15408794 | putative CCAAT-binding transcription facto . . . | 1 | 194 | 2.60E-30 | 2 |
| 1 | G481 | GI-16902054 | CCAAT-box binding factor HAP3 B domain [Ve . . . | 1 | 187 | 1.00E-28 | 2 |
| 1 | G481 | GI-16902050 | CCAAT-box binding factor HAP3 B domain [GI . . . | 1 | 188 | 2.70E-28 | 2 |
| 1 | G481 | GI-16902056 | CCAAT-box binding factor HAP3 B domain [Ar . . . | 1 | 189 | 4.30E-28 | 2 |
| 1 | G481 | GI-15321716 | AF410176_1 leafy cotyledon1 [*Zea mays*] | 1 | 179 | 1.20E-26 | 3 |
| 1 | G481 | GI-16902052 | CCAAT-box binding factor HAP3 B domain [GI . . . | 1 | 178 | 2.90E-26 | 2 |
| 1 | G481 | GI-15408793 | hypothetical protein-similar to CCAAT-bind . . . | 1 | 180 | 2.70E-24 | 2 |
| 1 | G481 | GI-16902058 | CCAAT-box binding factor HAP3 B domain [Tr . . . | 1 | 175 | 1.50E-23 | 2 |
| 1 | G481 | GI-18481628 | AF464906_1 repressor protein [*Glycine max*] | 1 | 110 | 2.10E-09 | 2 |
| 1 | G481 | GI-13928060 | NF-YB1 protein [*Oryza sativa*] | 1 | 111 | 0.00069 | 1 |
| 1 | G481 | GI-18481620 | AF464902_1 repressor protein [*Oryza sativa*] | 1 | 101 | 0.037 | 1 |
| 1 | G481 | GI-18481622 | AF464903_1 repressor protein [*Triticum aes* . . . | 1 | 100 | 0.052 | 1 |
| 3 | G1466 | BH596941 | BH596941 BOHFG41TR BOHF *Brassica oleracea* ge . . . | 1 | 557 | 1.40E-65 | 2 |
| 3 | G1466 | BH497171 | BH497171 BOHKV94TF BOHK *Brassica oleracea* ge . . . | -1 | 531 | 7.70E-49 | 1 |
| 3 | G1466 | BH515525 | BH515525 BOGZE84TR BOGZ *Brassica oleracea* ge . . . | -1 | 518 | 1.60E-47 | 1 |
| 3 | G1466 | BH685857 | BH685857 BOHWL93TF BO_2_3_KB *Brassica olerac* . . . | 1 | 409 | 6.90E-36 | 1 |
| 3 | G1466 | BH556937 | BH556937 BOHCT42TF BOHC *Brassica oleracea* ge . . . | 3 | 374 | 3.20E-32 | 1 |
| 3 | G1466 | BH716964 | BH716964 BOMNM26TR BO_2_3_KB *Brassica olerac* . . . | -2 | 371 | 6.40E-32 | 1 |
| 3 | G1466 | BH556945 | BH556945 BOHCT42TR BOHC *Brassica oleracea* ge . . . | -3 | 205 | 3.40E-24 | 2 |
| 3 | G1466 | BH586673 | BH586673 BOHPK25TF BOHP *Brassica oleracea* ge . . . | -1 | 293 | 1.80E-23 | 1 |
| 3 | G1466 | BH479514 | BH479514 BOHEU46TF BOHE *Brassica oleracea* ge . . . | -3 | 293 | 2.50E-23 | 1 |
| 3 | G1466 | BH442040 | BH442040 BOHJW94TF BOHJ *Brassica oleracea* ge . . . | 2 | 284 | 2.00E-22 | 1 |
| 3 | G1466 | BH468201 | BH468201 BOHAWO5TF BOHA *Brassica oleracea* ge . . . | 3 | 263 | 6.80E-20 | 1 |
| 3 | G1466 | BH554599 | BH554599 BOHES28TF BOHE *Brassica oleracea* ge . . . | -2 | 126 | 4.40E-17 | 3 |
| 3 | G1466 | BH443975 | BH443975 BOGYY14TR BOGY *Brassica oleracea* ge . . . | -1 | 220 | 7.20E-15 | 1 |
| 3 | G1466 | BH478506 | BH478506 BOGJO28TR BOGJ *Brassica oleracea* ge . . . | 2 | 184 | 3.10E-11 | 1 |
| 3 | G1466 | BH248066 | BH248066 BOGAU25TR BOGA *Brassica oleracea* ge . . . | 2 | 164 | 7.00E-08 | 1 |
| 3 | G1466 | BH455609 | BH455609 BOHPV23TF BOHP *Brassica oleracea* ge . . . | -1 | 160 | 6.60E-07 | 1 |
| 3 | G1466 | BH453095 | BH453095 BOGVR55TF BOGV *Brassica oleracea* ge . . . | 2 | 141 | 8.30E-05 | 1 |
| 3 | G1466 | BH536461 | BH536461 BOHMJ41TR BOHM *Brassica oleracea* ge . . . | 2 | 139 | 8.90E-05 | 1 |
| 3 | G1466 | BE462774 | BE462774 EST325108 tomato flower buds 0-3 mm . . . | 1 | 129 | 0.00014 | 1 |

TABLE 7-continued

| SEQ ID NO | Gene ID | Test Sequence ID | Test Sequence GenBank Annotation | Reading Frame | High Score | Smallest Sum Probability | N |
|---|---|---|---|---|---|---|---|
| 3 | G1466 | AW399721 | AW399721 EST310221 *L. pennellii* trichome, Co . . . | 3 | 124 | 0.00049 | 1 |
| 3 | G1466 | AV413010 | AV413010 AV413010 *Lotus japonicus* young plan . . . | 3 | 119 | 0.00054 | 1 |
| 3 | G1466 | AW032605 | AW032605 EST276164 tomato callus, TAMU *Lycop* . . . | 3 | 114 | 0.0021 | 1 |
| 3 | G1466 | BI927221 | 6I927221 EST547110 tomato flower, 3 - 8mm b . . . | 2 | 121 | 0.0023 | 1 |
| 3 | G1466 | OSJNO0182 | AL662981 *Oryza sativa* chromosome 4 clone OSJ . . . | 3 | 132 | 0.0029 | |
| 3 | G1466 | BG662160 | BG662160 Ljirnpest39-183-g3 Ljirnp Lambda Hy . . . | 2 | 111 | 0.0037 | 1 |
| 3 | G1466 | BG599234 | BG599234 EST504134 cSTS *Solanum tuberosum* cD . . . | 3 | 125 | 0.0047 | 1 |
| 3 | G1466 | BG133465 | BG133465 EST466357 tomato crown gall*Lycoper* . . . | 3 | 110 | 0.0059 | 1 |
| 3 | G1466 | BG596415 | BG596415 EST495093 cSTS *Solanum tuberosum* cD . . . | 3 | 109 | 0.0061 | 1 |
| 3 | G1466 | 61922297 | 61922297 EST542201 tomato callus *Lycopersico* . . . | 3 | 114 | 0.0065 | 1 |
| 3 | G1466 | BG097828 | BG097828 EST462347 potato leaves and petiole . . . | 1 | 122 | 0.0081 | 1 |
| 3 | G1466 | BI178485 | BI178485 EST519430 cSTE *Solanum tuberosum* cD . . . | 1 | 120 | 0.0095 | 1 |
| 3 | G1466 | BG580068 | BG580068 EST481790 GVN *Medicago truncatula* c . . . | 3 | 114 | 0.0095 | 1 |
| 3 | G1466 | AW932502 | AW932502 EST358345 tomato fruit mature green . . . | 3 | 118 | 0.011 | 1 |
| 3 | G1466 | BH700517 | BH700517 BOMEG26TR BO_2_3_KB *Brassica olerac* . . . | 1 | 106 | 0.013 | 1 |
| 3 | G1466 | AV414925 | AV414925 AV414925 *Lotus japonicus* young plan . . . | 1 | 106 | 0.014 | 1 |
| 3 | G1466 | BG887252 | BG887252 EST513103 cSTD *Solanum tuberosum* cD . . . | 3 | 121 | 0.015 | 1 |
| 3 | G1466 | BH649717 | BH649717 BOHTZ83TF BO_2_3_KB *Brassica olerac* . . . | −2 | 121 | 0.016 | 1 |
| 3 | G1466 | AW691672 | AW691672 NF047G1OST1F1000 Developing stem Me . . . | 3 | 105 | 0.02 | 1 |
| 3 | G1466 | BI316339 | BI316339 saf02a08.y1 Gm-c1065 *Glycine max* cD . . . | 1 | 115 | 0.026 | 1 |
| 3 | G1466 | BG409415 | BG409415 00787 leafy spurge Lambda HybriZAP . . . | 2 | 115 | 0.026 | 1 |
| 3 | G1466 | AP003837 | AP003837 *Oryza sativa* chromosome 7 clone OJ1 . . . | −2 | 123 | 0.027 | 1 |
| 3 | G1466 | AW928976 | AW928976 EST337860 tomato flower buds 8 mm t . . . | 2 | 115 | 0.03 | 1 |
| 3 | G1466 | OSJNO0167 | AL662965 Oryza sativa chromosome 4 clone OSJ . . . | −2 | 122 | 0.034 | 1 |
| 3 | G1466 | BH660321 | BH660321 BOMGE76TR BO_2_3_KB *Brassica olerac* . . . | −3 | 116 | 0.036 | 1 |
| 3 | G1466 | AW395660 | AW395660 sg73f12.y1 Gm-c1007 *Glycine max* cDN . . . | 3 | 102 | 0.037 | 1 |
| 3 | G1466 | BE459691 | BE459691 EST414983 tomato developing/immatur . . . | 2 | 102 | 0.038 | 1 |
| 3 | G1466 | BH558685 | BH558685 BOGEH17TR BOGE *Brassica olerace* ge . . . | 1 | 116 | 0.05 | 1 |
| 3 | G1466 | BH486360 | BH486360 BOHLY92TF BOHL *Brassica olerace* ge . . . | 3 | 116 | 0.056 | 1 |
| 3 | G1466 | AW218077 | AW218077 EST296792 tomato flower buds, anthe . . . | 1 | 114 | 0.078 | 1 |
| 3 | G1466 | AW650052 | AW650052 EST328506 tomato germinating seedli . . . | 1 | 112 | 0.08 | 1 |
| 3 | G1466 | BH698615 | BH698615 BOHUQ33TR BO_2_3_KB *Brassica olerac* . . . | 3 | 113 | 0.081 | 1 |
| 3 | G1466 | BG596140 | BG596140 EST494818 cSTS *Solanum tuberosum* cD . . . | 1 | 114 | 0.093 | 1 |
| 3 | G1466 | BE205043 | BE205043 EST397719 KVO *Medicago truncatula* c . . . | 2 | 112 | 0.097 | 1 |
| 3 | G1466 | BE919377 | BE919377 EST423230 potato leaves and petiole . . . | 3 | 111 | 0.097 | 1 |
| 3 | G1466 | BH437084 | BH437084 BOHKZ27TF BOHK *Brassica olerace* ge . . . | −3 | 99 | 0.1 | 1 |
| 3 | G1466 | BF278686 | BF278686 GA_Eb0035E2lf *Gossypium arboreum* 7 . . . | 3 | 111 | 0.11 | 1 |
| 3 | G1466 | BI933949 | BI933949 EST553838 tomato flower, anthesis L . . . | 3 | 113 | 0.12 | 1 |
| 3 | G1466 | BF096307 | BF096307 EST360356 tomato nutrient deficient . . . | 2 | 109 | 0.13 | 1 |
| 3 | G1466 | BH737844 | BH737844 BOMAX76TF BO_2_3_KB *Brassica olerac* . . . | −1 | 109 | 0.14 | 1 |
| 3 | G1466 | BI929823 | BI929823 EST549712 tomato flower, 3-8 mm b . . . | 3 | 104 | 0.17 | 1 |
| 3 | G1466 | BH513097 | BH513097 BOGEX21TR BOGE *Brassica olerace* ge . . . | −1 | 112 | 0.17 | 1 |
| 3 | G1466 | BE203214 | BE203214 EST403236 KV1 *Medicago truncatula* c . . . | 1 | 110 | 0.18 | 1 |
| 3 | G1466 | BE202448 | BE202448 EST392897 KV1 *Medicago truncatula* c . . . | 2 | 104 | 0.19 | 1 |
| 3 | G1466 | BF644564 | BF644564 NF016D06EC1F1057 Elicited cell cult . . . | 1 | 110 | 0.19 | 1 |
| 3 | G1466 | BI420528 | BI420528 LjNEST58c1Or *Lotus japonicus* nodule . . . | 3 | 96 | 0.2 | 1 |
| 3 | G1466 | BF010496 | BF010496 NXCI_084_G01_F NXCI (Nsf Xylem Comp . . . | 2 | 95 | 0.2 | 1 |
| 3 | G1466 | 81308763 | B1308763 EST530173 GPOD *Medicago truncatula* . . . | 3 | 107 | 0.21 | 1 |
| 3 | G1466 | BH469525 | BH469525 BOGSA70TF BOGS *Brassica olerace* ge . . . | 2 | 111 | 0.22 | 1 |
| 3 | G1466 | BE442810 | BE442810 WHE1106_C02_E04ZS Wheat etiolated s . . . | 1 | 110 | 0.23 | 1 |
| 3 | G1466 | BH569775 | BH569775 BOGMV91TF BOGM *Brassica olerace* ge . . . | −3 | 109 | 0.23 | 1 |
| 3 | G1466 | BH723965 | BH723965 BOMHF56TF BO_2_3_KB *Brassica olerac* . . . | −2 | 110 | 0.25 | 1 |
| 3 | G1466 | BH475440 | BH475440 BOHNA92TF BOHN *Brassica olerace* ge . . . | −2 | 109 | 0.26 | 1 |
| 3 | G1466 | BH730453 | BH730453 BOHVD24TR BO_2_3_KB *Brassica olerac* . . . | 1 | 110 | 0.27 | 1 |
| 3 | G1466 | AC082644 | AC082644 Oryza sativa chromosome 3 BAC OSJNB . . . | −2 | 113 | 0.28 | 1 |
| 3 | G1466 | AZ124264 | AZ124264 T223049b *Medicago truncatula* BAC li . . . | −3 | 93 | 0.31 | 1 |
| 3 | G1466 | BI922762 | BI922762 EST542666 tomato callus *Lycopersico* . . . | 3 | 104 | 0.34 | 1 |
| 3 | G1466 | AI443156 | AI443156 sa50f01.y1 Gm-c1004 *Glycine max* cDN . . . | 3 | 105 | 0.34 | 1 |
| 3 | G1466 | BE249557 | BE249557 NF022C06LF1F1049 Developing leaf Me . . . | 1 | 94 | 0.34 | 1 |
| 3 | G1466 | AL379504 | AL379504 MtBB45G03F1 MtBB *Medicago truncatul* . . . | 1 | 102 | 0.35 | 1 |
| 3 | G1466 | BF646352 | BF646352 NF068G05EC1F1039 Elicited cell cult . . . | 1 | 106 | 0.47 | 1 |
| 3 | G1466 | BH498652 | BH498652 BOGZR84TR BOGZ *Brassica olerace* ge . . . | −2 | 107 | 0.48 | 1 |
| 3 | G1466 | BM442042 | BM442042 EBan01_SQ002_A06_R IGF Barley EBanO . . . | 2 | 96 | 0.49 | 1 |
| 3 | G1466 | BG447666 | BG447666 NF019E03ST1F1000 Developing stem Me . . . | 1 | 106 | 0.49 | 1 |
| 3 | G1466 | AV427033 | AV427033 AV427033 *Lotus japonicus* young plan . . . | 1 | 98 | 0.5 | 1 |
| 3 | G1466 | AW216996 | AW216996 EST295710 tomato callus, TAMU Lycop . . . | 2 | 92 | 0.53 | 1 |
| 3 | G1466 | AW648500 | AW648500 EST326954 tomato germinating seedli . . . | 3 | 102 | 0.55 | 1 |
| 3 | G1466 | AW649521 | AW649521 EST327975 tomato germinating seedli . . . | 1 | 102 | 0.59 | 1 |
| 3 | G1466 | BF187212 | BF187212 EST443499 potato stolon, Cornell Un . . . | 3 | 102 | 0.62 | 1 |
| 3 | G1466 | BE202443 | BE202443 EST392892 KV1 *Medicago truncatula* c . . . | 3 | 104 | 0.65 | 1 |
| 3 | G1466 | BE344294 | BE344294 EST409456 potato stolon, Cornell Un . . . | 3 | 102 | 0.66 | 1 |
| 3 | G1466 | C72509 | C72509 C72509 Rice panicle at flowering stag . . . | 2 | 89 | 0.67 | 1 |
| 3 | G1466 | BH743977 | BH743977 gt29g06.b1 BoBuds01 *Brassica olerac* . . . | 2 | 101 | 0.68 | 1 |
| 3 | G1466 | AI967453 | AI967453 Ljirnpest02-129-d2 Ljirnp Lambda Hy . . . | 1 | 99 | 0.7 | 1 |
| 3 | G1466 | BI419994 | BI419994 LjNEST42f9r *Lotus japonicus* nodule . . . | 2 | 102 | 0.7 | 1 |
| 3 | G1466 | BG646874 | BG646874 EST508493 HOGA *Medicago truncatula* . . . | 2 | 104 | 0.7 | 1 |

TABLE 7-continued

| SEQ ID NO | Gene ID | Test Sequence ID | Test Sequence GenBank Annotation | Reading Frame | High Score | Smallest Sum Probability | N |
|---|---|---|---|---|---|---|---|
| 3 | G1466 | AW694435 | AW694435 NF076B06ST1F1048 Developing stem Me . . . | 1 | 102 | 0.75 | 1 |
| 3 | G1466 | AP004055 | AP004055 Oryza sativa chromosome 2 clone OJ1 . . . | 1 | 107 | 0.77 | 1 |
| 3 | G1466 | AP004144 | AP004144 Oryza sativa chromosome 2 clone OJ1 . . . | −3 | 107 | 0.77 | 1 |
| 3 | G1466 | OSJNO0115 | AL606997 Oryza sativa chromosome 4 clone OSJ . . . | −1 | 107 | 0.77 | 1 |
| 3 | G1466 | AP002071 | AP002071 Oryza sativa genomic DNA, chromosom . . . | −1 | 107 | 0.77 | 1 |
| 3 | G1466 | BE095245 | BE095245 00306 leafy spurge Lambda HybriZAP . . . | 1 | 88 | 0.79 | 1 |
| 3 | G1466 | BM526605 | BM526605 sa143e01.y1 Gm-c1059 Glycine max cD . . . | 2 | 100 | 0.8 | 1 |
| 3 | G1466 | BI933721 | BI933721 EST553610 tomato flower, anthesis L . . . | 3 | 102 | 0.86 | 1 |
| 3 | G1466 | BI272408 | BI272408 NFO2OHO9FL1F1079 Developing flower . . . | 3 | 102 | 0.87 | 1 |
| 3 | G1466 | BI933639 | BI933639 EST553528 tomato flower, anthesis L . . . | 3 | 102 | 0.89 | 1 |
| 3 | G1466 | BM108916 | BM108916 EST556452 potato roots Solanum tube . . . | 1 | 102 | 0.89 | 1 |
| 3 | G1466 | BH581102 | BH581102 BOHKD5OTF BOHK Brassica oleracea ge . . . | 3 | 95 | 0.9 | 1 |
| 3 | G1466 | BH692394 | BH692394 BOMKE64TF BO_2_3_KB Brassica olerac . . . | 3 | 99 | 0.92 | 1 |
| 3 | G1466 | BG131783 | BG131783 EST464675 tomato crown gall Lycoper . . . | 3 | 97 | 0.93 | 1 |
| 3 | G1466 | AI896339 | AI896339 EST265782 tomato callus, TAMU Lycop . . . | 2 | 94 | 0.93 | 1 |
| 3 | G1466 | BG404995 | BG404995 sac46g02.y1 Gm-c1062 Glycine max cD . . . | 1 | 97 | 0.95 | 1 |
| 3 | G1466 | AP004042 | AP004042 Oryza sativa chromosome 8 clone OJ1 . . . | 1 | 104 | 0.95 | 1 |
| 3 | G1466 | AP004708 | AP004708 Oryza sativa chromosome 8 clone P07 . . . | −3 | 104 | 0.95 | 1 |
| 3 | G1466 | AP004274 | AP004274 Oryza sativa chromosome 7 clone P04 . . . | −1 | 104 | 0.95 | 1 |
| 3 | G1466 | BE919578 | BE919578 EST423347 potato leaves and petiole . . . | 1 | 100 | 0.95 | 1 |
| 3 | G1466 | BF634570 | BF634570 NF061B09DT1F1076 Drought Medicago t . . . | 3 | 100 | 0.96 | 1 |
| 3 | G1466 | BI420155 | BI420155 LjNEST53f7r Lotus japonicus nodule . . . | 3 | 96 | 0.97 | 1 |
| 3 | G1466 | AQ917137 | AQ917137 T233170b Medicago truncatula BAC li . . . | −1 | 99 | 0.97 | 1 |
| 3 | G1466 | AW720029 | AW720029 LjNEST15c9rLotus japonicus nodule . . . | 2 | 96 | 0.98 | 1 |
| 3 | G1466 | AW568479 | AW568479 si59c09.y1 Gm-rl030 Glycine max cDN . . . | 3 | 97 | 0.98 | 1 |
| 3 | G1466 | B1420626 | B1420626 LjNEST59e5r Lotus japonicus nodule . . . | 3 | 96 | 0.99 | 1 |
| 3 | G1466 | BE433506 | BE433506 EST400035 tomato breaker fruit, TIG . . . | 2 | 97 | 0.99 | 1 |
| 3 | G1466 | BI785473 | BI785473 sai41d06.y1 Gm-c1065 Glycine max cD . . . | 3 | 97 | 0.991 | 1 |
| 3 | G1466 | BH737087 | BH737087 BOMGM48TR BO_2_3_KB Brassica olerac . . . | 3 | 98 | 0.991 | 1 |
| 3 | G1466 | BM324672 | BM324672 PIC1_34_B01.b1_A002 Pathogen-infect . . . | 3 | 98 | 0.992 | 1 |
| 3 | G1466 | BH425892 | BH425892 BOGDN33TF BOGD Brassica oleracea ge . . . | −3 | 98 | 0.994 | 1 |
| 3 | G1466 | BH645340 | BH645340 BOHWO42TF BO_2_3_KBBrassica olerac . . . | −3 | 97 | 0.995 | 1 |
| 3 | G1466 | AW687534 | AW687534 NF010F07RT1F1062 Developing root Me . . . | 3 | 96 | 0.997 | 1 |
| 3 | G1466 | BF176934 | BF176934 EM1_4_E11.b1_A002 Embryo 1 (EM1) So . . . | 3 | 96 | 0.997 | 1 |
| 3 | G1466 | BI419241 | BI419241 LjNEST44a5r Lotus japonicus nodule . . . | 3 | 96 | 0.998 | 1 |
| 3 | G1466 | AL380183 | AL380183 MtBB5OHO9F1 MtBB Medicago truncatul . . . | 1 | 94 | 0.998 | 1 |
| 3 | G1466 | AC079128 | AC079128 Oryza sativa chromosome 10 clone OS . . . | 3 | 101 | 0.998 | 1 |
| 3 | G1466 | BF070938 | BF070938 st85e05.y1 Gm-c1054 Glycine max cDN . . . | 3 | 95 | 0.999 | 1 |
| 3 | G1466 | AW928966 | AW928966 EST337850 tomato flower buds 8 mm t . . . | 3 | 86 | 0.9995 | 1 |
| 3 | G1466 | BH429646 | BH429646 BOGSF37TF BOGS Brassica oleracea ge . . . | −3 | 97 | 0.9997 | 1 |
| 3 | G1466 | BH560749 | BH560749 BOGPCO1TR BOGP Brassica oleracea ge . . . | −1 | 97 | 0.9997 | 1 |
| 3 | G1466 | AP004150 | AP004150 Oryza sativa chromosome 2 clone OJ1 . . . | −1 | 100 | 0.9998 | 1 |
| 3 | G1466 | AP004077 | AP004077 Oryza sativa chromosome 2 clone OJ1 . . . | 1 | 100 | 0.9998 | 1 |
| 3 | G1466 | BG130763 | BG130763 EST463655 tomato crown gall Lycoper . . . | 3 | 96 | 0.9998 | 1 |
| 3 | G1466 | BH484808 | BH484808 BOGQC69TR BOGQ Brassica oleracea ge . . . | 1 | 97 | 0.9998 | 1 |
| 3 | G1466 | BF651138 | BF651138 NF101G05EC1F1038 Elicited cell cult . . . | 1 | 96 | 0.9999 | 1 |
| 3 | G1466 | BF650226 | BF650226 NF090F1OEC1F1089 Elicited cell cult . . . | 3 | 96 | 0.9999 | 1 |
| 3 | G1466 | BF647598 | BF647598 NF012A06EC1F1039 Elicited cell cult . . . | 3 | 96 | 0.9999 | 1 |
| 3 | G1466 | BG447988 | BG447988 NF103H1OEC1F1090 Elicited cell cult . . . | 3 | 96 | 0.9999 | 1 |
| 3 | G1466 | BH480188 | BH480188 BOGZW54TR BOGZ Brassica oleraceage . . . | 3 | 97 | 0.99991 | 1 |
| 3 | G1466 | BF519054 | BF519054 EST456514 DSIL Medicago truncatula . . . | 3 | 96 | 0.99994 | 1 |
| 3 | G1466 | GI-8096405 | Similar to Arabidopsis thaliana chromosome . . . | −3 | 137 | 2.30E−12 | 2 |
| 3 | G1466 | GI-8096413 | hypothetical protein [Oryza sativa] | −3 | 135 | 2.20E−11 | 2 |
| 3 | G1466 | GI-8096416 | hypothetical protein [Oryza sativa] | −3 | 111 | 9.40E−09 | 3 |
| 3 | G1466 | GI-13161526 | S locus F-box (SLF)-S2 protein [Antirrhinu . . . | −3 | 92 | 3.40E−08 | 3 |
| 3 | G1466 | GI-13161540 | SLF-S2 protein [Antirrhinum hispanicum] | −3 | 92 | 3.40E−08 | 3 |
| 3 | G1466 | GI-13161528S | locus F-box (SLF)-S2-like protein [Antir . . . | −1 | 87 | 1.20E−07 | 3 |
| 3 | G1466 | GI-8096415 | hypothetical protein [Oryza sativa] | −1 | 102 | 3.60E−07 | 2 |
| 3 | G1466 | AC0875995 | unknown protein [Oryza sativa] | −1 | 90 | 1.10E−05 | 3 |
| 3 | G1466 | GI-14028986 | AC079128_10 Unknown protein [Oryza sativa] | −1 | 101 | 4.60E−05 | 2 |
| 3 | G1466 | GI-18854992 | AC087599_3 putative transposase [Oryza sat . . . | −3 | 93 | 0.0014 | 3 |
| 3 | G1466 | GI-12039340 | AC082644_9 hypothetical protein [Oryza sat . . . | −1 | 113 | 0.0029 | 1 |
| 3 | G1466 | GI-14018043 | AC079936_2 Hypothetical protein [Oryza sat . . . | −1 | 87 | 0.012 | 2 |
| 3 | G1466 | GI-15451623 | AC091734_4 Hypothetical protein [Oryza sat . . . | −1 | 87 | 0.012 | 2 |
| 3 | G1466 | GI-15528755 | hypothetical protein [Oryza sativa] | −1 | 96 | 0.012 | 2 |
| 3 | G1466 | GI-8096406 | hypothetical protein [Oryza sativa] | −3 | 98 | 0.013 | 2 |
| 3 | G1466 | GI-8096410 | hypothetical protein [Oryza sativa] | −1 | 103 | 0.022 | 1 |
| 3 | G1466 | GI-18844804 | contains ESTs D15126(C0122), C97919(C0122)~ . . . | −1 | 99 | 0.083 | 1 |
| 3 | G1466 | GI-18449949 | AC099733_6 Unknown protein [Oryza sativa] | −1 | 81 | 0.099 | 2 |
| 3 | G1466 | GI-18464016 | AC090873_9 Hypothetical protein [Oryza sat . . . | −3 | 69 | 0.23 | 2 |
| 3 | G1466 | GI-19224986 | AC077693_1 putative transposase protein, 5 . . . | −3 | 93 | 0.24 | 2 |
| 3 | G1466 | GI-12039332 | AC082644_1 hypothetical protein [Oryza sat . . . | −1 | 91 | 0.5 | 1 |
| 3 | G1466 | GI-18461280 | similar to Oryza sativa chromosome 1, P045 . . . | −3 | 72 | 0.61 | 2 |
| 3 | G1466 | GI-9858770 | AF273333_2 BAC19.2 [Lycopersicon esculentum] | −1 | 70 | 0.83 | 2 |
| 3 | G1466 | GI-12039337 | AC082644_6 hypothetical protein [Oryza sat . . . | −1 | 87 | 0.85 | 1 |
| 3 | G1466 | GI-18642684 | AC074283_6 Hypothetical protein [Oryza sat . . . | −1 | 79 | 0.9 | 2 |

TABLE 7-continued

| SEQ ID NO | Gene ID | Test Sequence ID | Test Sequence GenBank Annotation | Reading Frame | High Score | Smallest Sum Probability | N |
|---|---|---|---|---|---|---|---|
| 3 | G1466 | GI-18642688 | AC074283_7 Unknown protein [*Oryza sativa*] | −1 | 75 | 0.97 | 1 |
| 3 | G1466 | GI-18087878 | AC087182_15 hypothetical protein [*Oryza sa . . .* ] | −1 | 87 | 0.98 | 1 |
| 3 | G1466 | GI-18873858 | AC079874_27 hypothetical protein [*Oryza sa . . .* ] | −3 | 81 | 0.994 | 1 |
| 3 | G1466 | GI-6505722 | ribosomal RNA apurinic site specific lyase | −1 | 81 | 0.99993 | 1 |
| 3 | G1466 | GI-6513849 | ribosomal RNA apurinic site specific lyase | −1 | 81 | 0.99993 | 1 |

What is claimed is:

1. A method for producing and selecting a plant having an altered trait relative to a wild-type plant of the same species, wherein the altered trait is greater yield than the wild-type plant, the method steps comprising:
   (a) providing a polynucleotide encoding a polypeptide with at least 95% amino acid sequence identity to SEQ ID NO: 2;
   (b) inserting the polynucleotide into a DNA construct;
   (c) introducing the DNA construct into the plant to produce a transgenic plant;
      wherein the polypeptide is overexpressed in the transgenic plant, and as a result of said overexpression the polypeptide confers to the transgenic plant the greater yield; and
   (d) selecting one or more of the transgenic plants exhibiting greater yield than the wild-type plant.

2. The method of claim 1, wherein the polypeptide has an amino acid sequence that is at least 98% identical to the amino acid sequence of SEQ ID NO: 2.

3. The method of claim 1, wherein the polypeptide comprises SEQ ID NO: 2.

4. The method of claim 1, wherein the polynucleotide comprises SEQ ID NO: 1.

5. The method of claim 1, wherein the plant is monocotyledonous.

6. The method of claim 1, wherein the transgenic plant is derived from a transformed seed comprising the polynucleotide.

7. A method for producing and selecting a plant having an altered trait relative to a wild-type plant of the same species, wherein the altered trait is darker green color than the wild-type plant, the method steps comprising:
   (a) providing a polynucleotide encoding a polypeptide with at least 95% amino acid sequence identity to SEQ ID NO: 2;
   (b) inserting the polynucleotide into a DNA construct;
   (c) introducing the DNA construct into the plant to produce a transgenic plant;
      wherein the polypeptide is overexpressed in the transgenic plant, and as a result of said overexpression the polypeptide confers to the transgenic plant the darker green color; and
   (d) selecting one or more of the transgenic plants exhibiting darker green color than the wild-type plant.

8. The method of claim 7, wherein the polypeptide has an amino acid sequence that is at least 98% identical to the amino acid sequence of SEQ ID NO: 2.

9. The method of claim 7, wherein the polypeptide comprises SEQ ID NO: 2.

10. The method of claim 7, wherein the polynucleotide comprises SEQ ID NO: 1.

11. The method of claim 7, wherein the plant is monocotyledonous.

12. The method of claim 7, wherein the transgenic plant is derived from a transformed seed comprising the polynucleotide.

13. A method for producing and selecting a plant having an altered trait relative to a wild-type plant of the same species, wherein the altered trait is a higher photosynthetic rate than the wild-type plant, the method steps comprising:
   (a) providing a polynucleotide encoding a polypeptide with at least 95% amino acid sequence identity to SEQ ID NO: 2;
   (b) inserting the polynucleotide into a DNA construct;
   (c) introducing the DNA construct into the plant to produce a transgenic plant;
      wherein the polypeptide is overexpressed in the transgenic plant, and as a result of said overexpression the polypeptide confers to the transgenic plant the higher photosynthetic rate; and
   (d) selecting one or more of the transgenic plants exhibiting a higher photosynthetic rate than the wild-type plant.

14. The method of claim 13, wherein the polypeptide has an amino acid sequence that is at least 98% identical to the amino acid sequence of SEQ ID NO: 2.

15. The method of claim 13, wherein the polypeptide comprises SEQ ID NO: 2.

16. The method of claim 13, wherein the polynucleotide comprises SEQ ID NO: 1.

17. The method of claim 13, wherein the plant is monocotyledonous.

18. The method of claim 13, wherein the transgenic plant is derived from a transformed seed comprising the polynucleotide.

* * * * *

SEQUENCE LISTING

<160> NUMBER OF SEQ ID NOS: 4

<210> SEQ ID NO 1
<211> LENGTH: 832
<212> TYPE: DNA
<213> ORGANISM: Arabidopsis thaliana
<220> FEATURE:
<223> OTHER INFORMATION: G481

<400> SEQUENCE: 1

```
gagcgtttcg tagaaaaatt cgatttctct aaagccctaa aactaaaacg actatcccca      60
attccaagtt ctagggtttc catcttcccc aatctagtat aaatggcgga tacgccttcg     120
agcccagctg gagatggcgg agaaagcggc ggttccgtta gggagcagga tcgatacctt     180
cctatagcta atatcagcag gatcatgaag aaagcgttgc ctcctaatgg taagattgga     240
aaagatgcta aggatacagt tcaggaatgc gtctctgagt tcatcagctt catcactagc     300
gaggccagtg ataagtgtca aaaagagaaa aggaaaactg tgaatggtga tgatttgttg     360
tgggcaatgg caacattagg atttgaggat tacctggaac ctctaaagat ataccctagcg     420
aggtacaggg agttggaggg tgataataag ggatcaggaa agagtggaga tggatcaaat     480
agagatgctg gtggcggtgt ttctggtgaa gaaatgccga gctggtaaaa gaagttgcaa     540
gtagtgatta agaacaatcg ccaaatgatc aagggaaatt agagatcagt gagttgttta     600
tagttgagct gatcgacaac tatttcgggt ttactctcaa tttcggttat gttagtttga     660
acgtttggtt tattgtttcc ggtttagttg gttgtattta aagatttctc tgttagatgt     720
tgagaacact tgaatgaagg aaaaatttgt ccacatcctg ttgttatttt cgattcactt     780
tcggaatttc atagctaatt tattctcatt taataccaaa tccttaaatt aa              832
```

<210> SEQ ID NO 2
<211> LENGTH: 141
<212> TYPE: PRT
<213> ORGANISM: Arabidopsis thaliana
<220> FEATURE:
<223> OTHER INFORMATION: G481 polypeptide

<400> SEQUENCE: 2

```
Met Ala Asp Thr Pro Ser Ser Pro Ala Gly Asp Gly Gly Glu Ser Gly
1               5                   10                  15

Gly Ser Val Arg Glu Gln Asp Arg Tyr Leu Pro Ile Ala Asn Ile Ser
            20                  25                  30

Arg Ile Met Lys Lys Ala Leu Pro Pro Asn Gly Lys Ile Gly Lys Asp
        35                  40                  45

Ala Lys Asp Thr Val Gln Glu Cys Val Ser Glu Phe Ile Ser Phe Ile
    50                  55                  60
```

| | | | | | | | | | | | | | | | |
|---|---|---|---|---|---|---|---|---|---|---|---|---|---|---|---|
| Thr | Ser | Glu | Ala | Ser | Asp | Lys | Cys | Gln | Lys | Glu | Lys | Arg | Lys | Thr | Val |
| 65 | | | | 70 | | | | | 75 | | | | | 80 | |

| | | | | | | | | | | | | | | |
|---|---|---|---|---|---|---|---|---|---|---|---|---|---|---|
| Asn | Gly | Asp | Asp | Leu | Leu | Trp | Ala | Met | Ala | Thr | Leu | Gly | Phe | Glu | Asp |
| | | | 85 | | | | | 90 | | | | | 95 | | |

| | | | | | | | | | | | | |
|---|---|---|---|---|---|---|---|---|---|---|---|---|
| Tyr | Leu | Glu | Pro | Leu | Lys | Ile | Tyr | Leu | Ala | Arg | Tyr | Arg | Glu | Leu | Glu |
| | | | 100 | | | | | 105 | | | | | 110 | | |

| | | | | | | | | | | | | |
|---|---|---|---|---|---|---|---|---|---|---|---|---|
| Gly | Asp | Asn | Lys | Gly | Ser | Gly | Lys | Ser | Gly | Asp | Gly | Ser | Asn | Arg | Asp |
| | | 115 | | | | | 120 | | | | | 125 | | | |

| | | | | | | | | | |
|---|---|---|---|---|---|---|---|---|---|
| Ala | Gly | Gly | Gly | Val | Ser | Gly | Glu | Glu | Met | Pro | Ser | Trp |
| | 130 | | | | | 135 | | | | | 140 | |

```
<210> SEQ ID NO 3
<211> LENGTH: 1342
<212> TYPE: DNA
<213> ORGANISM: Arabidopsis thaliana
<220> FEATURE:
<223> OTHER INFORMATION: G1466

<400> SEQUENCE: 3
caacaagctt caaaaatggg ggaagaagaa gagaacccta attcgatcga cattcttccc        60
gagctacttg aagaagttct ccttagattg cccacgaaat cgatcctcaa atgcagaatc       120
gtctcaaaac aatggaggtc actcctggaa tcgagtaggt tcgcggagag gcatatgagt       180
cttcaaaaca gccgccggag aatcttagct gcttacaact gcgactgcgg cggacggagg       240
aagctcctac ccgagtcacg gtttgaaggg gacgaagaga ttgtctatct gcactgcgac       300
gcctcacgac cctcgatgac ttgccaaggt gtgatctgct cccccagca agattggatc       360
atcgttttga acccatcgac tagccaactt cggcgattcc cttccggctt gaaccataac       420
tgcagattta gaattggatt atggaagact ttctctccgg gaaactgggt aatgggtttt       480
ggtagagaca aagtgaatgg gaggtataaa gtggtgagga tgtcttttgc tttctggaga       540
gttaggcaag aggagcctgt ggtggaatgt ggtgttcttg atgttgatac tggtgaatgg       600
cggaagctga gtccacctcc ttatgtggtc aatgtgggaa gcaaatcggt atgcgtgaat       660
ggatctatct actggttaca cattcagacg gtttacagaa tactagcctt ggatcttcac       720
aaacaagagt ttcataaagt cccagtgccg cctacgcaga tcactgtgga cactcagatg       780
gtgaaccttg aggaccgtct cgtacttgct ataaccagag ttagccctga atggatacta       840
gaggtatggg gcatggatac atacaaagaa aaatggagca agacttactc cataagtttg       900
gatcatagag ttgtttcctg gcgaaggcag aaaaggtggt tcacgcccgt ggcagtttct       960
aagcaagcga atcttgtctt ctatgacaat aagaagaggc tattcaaata ttatccagtg      1020
aaagatgaga ttcgttgtct ctccttagac atttgtgttc tgtctcctta cgtggaaaac      1080
ttggtccctc ttccgttaaa gccaagccat ccgcatccta ctccgaaaaa ttcagatttt      1140
gaaatgagga tatcaagatg ccgcttgttt tcgacgccag gttcttggat atccaaaatt      1200
ttgaaatgga atgttatgac tctagagatt ttgtttacct ctctagcaat agttggttat      1260
atatgcttac ctctctagga gttatttatc ttgtttcaaa atattagttg gttatatatg      1320
ctttcgagat ctttctgata aa                                                1342

<210> SEQ ID NO 4
<211> LENGTH: 420
<212> TYPE: PRT
<213> ORGANISM: Arabidopsis thaliana
<220> FEATURE:
<223> OTHER INFORMATION: G1466 polypeptide

<400> SEQUENCE: 4
```

-continued

```
Met Gly Glu Glu Glu Asn Pro Asn Ser Ile Asp Ile Leu Pro Glu
1               5                   10                  15

Leu Leu Glu Glu Val Leu Leu Arg Leu Pro Thr Lys Ser Ile Leu Lys
            20                  25                  30

Cys Arg Ile Val Ser Lys Gln Trp Arg Ser Leu Leu Glu Ser Ser Arg
            35                  40                  45

Phe Ala Glu Arg His Met Ser Leu Gln Asn Ser Arg Arg Ile Leu
50                  55                  60

Ala Ala Tyr Asn Cys Asp Cys Gly Arg Arg Lys Leu Leu Pro Glu
65                  70                  75                  80

Ser Arg Phe Glu Gly Asp Glu Glu Ile Val Tyr Leu His Cys Asp Ala
                85                  90                  95

Ser Arg Pro Ser Met Thr Cys Gln Gly Val Ile Cys Phe Pro Glu Gln
                100                 105                 110

Asp Trp Ile Ile Val Leu Asn Pro Ser Thr Ser Gln Leu Arg Arg Phe
            115                 120                 125

Pro Ser Gly Leu Asn His Asn Cys Arg Phe Arg Ile Gly Leu Trp Lys
    130                 135                 140

Thr Phe Ser Pro Gly Asn Trp Val Met Gly Phe Gly Arg Asp Lys Val
145                 150                 155                 160

Asn Gly Arg Tyr Lys Val Val Arg Met Ser Phe Ala Phe Trp Arg Val
                165                 170                 175

Arg Gln Glu Glu Pro Val Val Glu Cys Gly Val Leu Asp Val Asp Thr
            180                 185                 190

Gly Glu Trp Arg Lys Leu Ser Pro Pro Tyr Val Val Asn Val Gly
            195                 200                 205

Ser Lys Ser Val Cys Val Asn Gly Ser Ile Tyr Trp Leu His Ile Gln
210                 215                 220

Thr Val Tyr Arg Ile Leu Ala Leu Asp Leu His Lys Gln Glu Phe His
225                 230                 235                 240

Lys Val Pro Val Pro Pro Thr Gln Ile Thr Val Asp Thr Gln Met Val
                245                 250                 255

Asn Leu Glu Asp Arg Leu Val Leu Ala Ile Thr Arg Val Ser Pro Glu
                260                 265                 270

Trp Ile Leu Glu Val Trp Gly Met Asp Thr Tyr Lys Glu Lys Trp Ser
            275                 280                 285

Lys Thr Tyr Ser Ile Ser Leu Asp His Arg Val Val Ser Trp Arg Arg
            290                 295                 300

Gln Lys Arg Trp Phe Thr Pro Val Ala Val Ser Lys Gln Ala Asn Leu
305                 310                 315                 320

Val Phe Tyr Asp Asn Lys Lys Arg Leu Phe Lys Tyr Tyr Pro Val Lys
                325                 330                 335

Asp Glu Ile Arg Cys Leu Ser Leu Asp Ile Cys Val Leu Ser Pro Tyr
                340                 345                 350

Val Glu Asn Leu Val Pro Leu Pro Leu Lys Pro Ser His Pro His Pro
            355                 360                 365

Thr Pro Lys Asn Ser Asp Phe Glu Met Arg Ile Ser Arg Cys Arg Leu
    370                 375                 380

Phe Ser Thr Pro Gly Ser Trp Ile Ser Lys Ile Leu Lys Trp Asn Val
385                 390                 395                 400

Met Thr Leu Glu Ile Leu Phe Thr Ser Leu Ala Ile Val Gly Tyr Ile
                405                 410                 415

Cys Leu Pro Leu
            420
```